United States Patent
Zhang et al.

(10) Patent No.: US 10,517,862 B2
(45) Date of Patent: Dec. 31, 2019

(54) FUSED HETEROCYCLIC COMPOUND DERIVATIVE AND APPLICATION THEREOF

(71) Applicants: NHWA PHARMA. CORPORATION, Xuzhou, Jiangsu (CN); WUHAN JIAYU TECHNOLOGY CO., LTD., Wuhan, Hubei (CN)

(72) Inventors: Guisen Zhang, Xuzhou (CN); Xudong Cao, Xuzhou (CN); Yin Chen, Xuzhou (CN); Yifang Zhang, Hubei (CN); Minquan Yu, Xuzhou (CN); Yinli Qiu, Xuzhou (CN); Xiangqing Xu, Xuzhou (CN); Tan Zhang, Xuzhou (CN); Bifeng Liu, Hubei (CN); Xin Liu, Hubei (CN)

(73) Assignees: NHWA PHARMA. CORPORATION, Xuzhou (CN); WUHAN JIAYU TECHNOLOGY CO., LTD., Wuhan (CN)

( * ) Notice: Subject to any disclaimer, the term of this patent is extended or adjusted under 35 U.S.C. 154(b) by 0 days.

(21) Appl. No.: 15/771,225

(22) PCT Filed: Oct. 26, 2016

(86) PCT No.: PCT/CN2016/103329
§ 371 (c)(1),
(2) Date: Apr. 26, 2018

(87) PCT Pub. No.: WO2017/071576
PCT Pub. Date: May 4, 2017

(65) Prior Publication Data
US 2018/0318286 A1 Nov. 8, 2018

(30) Foreign Application Priority Data

Oct. 26, 2015 (CN) .......................... 2015 1 0702848

(51) Int. Cl.
| | | |
|---|---|---|
| A61K 31/4745 | (2006.01) | |
| A61K 31/496 | (2006.01) | |
| C07D 455/04 | (2006.01) | |
| C07D 471/06 | (2006.01) | |
| A61P 25/18 | (2006.01) | |
| A61K 31/506 | (2006.01) | |

(52) U.S. Cl.
CPC ........ *A61K 31/4745* (2013.01); *A61K 31/496* (2013.01); *A61K 31/506* (2013.01); *A61P 25/18* (2018.01); *C07D 455/04* (2013.01); *C07D 471/06* (2013.01)

(58) Field of Classification Search
CPC ............................ C07D 455/04; C07D 471/06
See application file for complete search history.

(56) References Cited

U.S. PATENT DOCUMENTS

2004/0138230 A1* 7/2004 Andreana ............ C07D 401/12
514/253.07

FOREIGN PATENT DOCUMENTS

| EP | 0367141 A2 | 5/1990 |
| GB | 2071094 A | 9/1981 |
| JP | 56125370 | 10/1981 |
| JP | 56164186 A | 12/1981 |
| JP | 02191256 | 7/1990 |
| WO | WO-2004026864 A1 | 4/2004 |
| WO | WO-2006090273 A2 | 8/2006 |
| WO | WO 2008/015516 * | 2/2008 |
| WO | WO-2008015516 A1 | 2/2008 |

OTHER PUBLICATIONS

"European Application Serial No. 16859011.5, Extended European Search Report dated Mar. 25, 2019", (dated Mar. 25, 2019), 7 pgs.
Hecker, Scott J., et al., "Prodrugs of phosphates and phosphonates", Journal of medicinal chemistry 51.8, (2008), 2328-2345.
Higuchi, Takeru, et al., "Pro-drugs as novel drug delivery systems", American Chemical Society, (1975), 249 pgs.
Rautio, Jarkko, et al., "Prodrugs: design and clinical applications", Nature Reviews Drug Discovery 7.3, (2008), 255-270.
Roche, Edward B., "Bioreversible Carriers in Drug Design, American Pharmaceutical Association and Pergamon Press, 1987", (1987), 3 pgs.
"International Application No. PCT/CN2016/103329, International Search Report dated Jan. 23, 2017", w/ English Translation, (dated Jan. 23, 2017), 5 pgs.
"International Application No. PCT/CN2016/103329, Written Opinion dated Jan. 23, 2017", (dated Jan. 23, 2017), 3 pgs.
"Japanese Appliccation Serial No. 2018-522505, Notification of Refusal dated May 21, 2019", w/ English Translation, (dated May 21, 2019), 6 pgs.

* cited by examiner

Primary Examiner — Valerie Rodriguez-Garcia
(74) Attorney, Agent, or Firm — Schwegman Lundberg & Woessner, P.A.

(57) ABSTRACT

The present invention relates to the field of pharmaceutical chemistry, and specifically relates to a fused heterocyclic compound derivative and an application thereof. The fused heterocyclic compound derivative has the structure of general formula (I), and can be used to treat neuropsychiatric diseases.

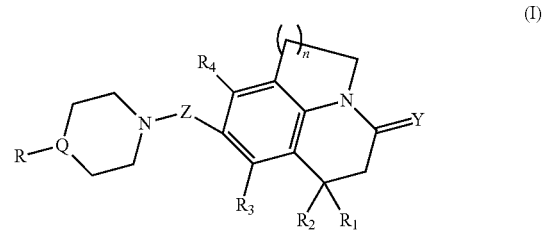

(I)

11 Claims, No Drawings

FUSED HETEROCYCLIC COMPOUND DERIVATIVE AND APPLICATION THEREOF

PRIORITY APPLICATIONS

This application is a U.S. National Stage Filing under 35 U.S.C. 371 from International Application No. PCT/CN2016/103329, filed on Oct. 26, 2016, and published as WO2017/071576 on May 4, 2017, which claims the benefit of priority to Chinese Application No. 201510702848.3, filed on Oct. 26, 2015; the benefit of priority of each of which is hereby claimed herein, and which applications and publication are hereby incorporated herein by reference in their entirety.

TECHNICAL FIELD

The invention belongs to the pharmaceutical chemistry field and particularly relates to the synthesis of a fused heterocyclic compound derivative and use thereof. More particularly, the invention relates to a fused heterocyclic compound derivative, a pharmaceutical composition comprising the same, and use of the pharmaceutical composition and the fused heterocyclic compound derivative in the manufacture of a medicament for the prevention or treatment of neuropsychical disease.

BACKGROUND

Schizophrenia is a type of disease characterized in severely schizophrenic cognition and emotion, presenting as the influence on the basic behavior of a human, such as language, thinking, feeling, self-perception or the like. This disease encompasses a large variety of disorders, such as those involved in psyche, e.g. delusion, paranoia, illusion or the like. Schizophrenia is the most serious mental disease. About 1% of the people all over the world suffer from schizophrenia, and only 5% of them can be cured after treatments. In addition, schizophrenia is always accompanied with various complications, e.g. anxiety, depression, psychic drug abuse or the like. It was shown in a study by Datamonitor that over ⅓ of the patients with schizophrenia suffer from one or more complicated psychoses or cognitive disorders.

The anti-psychosis drug exerting its pharmacological action by blocking dopamine $D_2$ receptor is conventionally known as the $1^{st}$ generation anti-psychosis drug, i.e. the "typical" anti-psychosis drug (e.g. haloperidol). This drug is effective for positive symptoms of schizophrenia, but not effective for negative symptoms and cognitive disorders. Furthermore, the typical anti-psychosis drug generally has serious EPS (extrapyramidal system) side effects and is not effective for ⅓ of the patients with schizophrenia.

A series of new anti-psychosis drugs have been developed since 1960s, including ziprasidone, risperidone or the like, which are considered as the $2^{nd}$ generation anti-psychosis drugs (the novel anti-psychosis drug). Although these drugs have different pharmacological actions, they share the same pharmacological properties, i.e. the affinities for 5-hydroxytryptamine (5-HT) receptor (5-HT1A, 2A, 2C) and noradrenalin (NA) receptor ($α_1$, $α_2$) are much higher than those for $D_2$ receptor, resulting in the decrease of the ratio of $D_2$/5-$HT_{2A}$. Their clinical effects are more advantageous over those of the $1^{st}$ generation anti-psychosis drugs, since they are effective for the positive symptoms like the conventional anti-psychosis drug, and are effective for the negative symptoms and cognitive defect symptoms and have broader application spectrum. However, these drugs have the side effects of extended QT interval, hyperprolactinemia, weight gain or the like. Therefore, it is needed to find a new drug, which is effective for schizophrenia positive and negative symptoms and cognitive disorders, and has less side effects.

Aripiprazole belongs to a butyl benzene prazosin compound, which was approved by FDA in November, 2002. This drug has a particular action mechanism as having high affinities with dopamine $D_2$, $D_3$, 5-$HT_{1A}$ and 5-$HT_{2A}$ receptors, and medium affinities with $D_4$, 5-$HT_{2C}$, 5-$HT_7$, $α_1$, $H_1$ receptors and 5-HT reuptake site. Aripiprazole exerts its effect against schizophrenia through its partial agonistic action for $D_2$ and 5-$HT_{1A}$ receptors and antagonistic action for 5-$HT_{2A}$ receptor, and has the effect of stabilizing dopamine systemic activity. Clinical trials have shown that aripiprazole is effective for both the positive and negative symptoms of schizophrenia, and its long-term application can reduce the reoccurrence of schizophrenia, and improve disorders of emotion and cognitive function. Moreover, its EPS side effects and the effect of increasing serum prolactin level are less than those of the conventional anti-psychosis drug or the above non-typical anti-psychosis drug.

5-hydroxytryptamine system plays an important role in modulating the function of prefrontal cortex (PFC), including emotion control, cognitive behavior and working memory. The pyramidal neurons and GABA interneurons of PFC contain several 5-hydroxytryptamine receptor subtypes 5-$HT_{1A}$ and 5-$HT_{2A}$ with high density. It has been shown recently that PFC and NMDA receptor pathway are the targets of 5-HT1AR, and these two receptors modulate the excitatory neuron of cerebral cortex, thereby affecting the cognitive function. In fact, various preclinical data have shown that 5-HT1AR may be the new target of the development of anti-psychosis drug. The high affinity of non-typical anti-psychosis drug (e.g. olanzapine, aripiprazole or the like) to 5-HT1AR and its low EPS side effects indicate that 5-hydroxytryptamine system plays an important role in modulating the function of prefrontal cortex (PFC), including emotion control, cognitive behavior and working memory. Pyramidal neurons of PFC and GABA interneurons contain several subtypes of 5-hydroxytryptamine receptors including 5-$HT_{1A}$ and 5-$HT_{2A}$ with especially high density. It has been shown recently that 5-$HT_{1A}$ agonist is associated with non-typical anti-psychosis drug therapy, which can improve negative symptoms and cognitive disorders. In the treatment of schizophrenia with the non-typical anti-psychosis drug clozapine, it was found that 5-$HT_{2A}$ plays an important role in various aspects, including cognition, emotion regulation and motion control. The blocking of 5-$HT_{2A}$ receptor can normalize the release of dopamine, exerting the effect of anti-psychosis. In addition, 5-$HT_{2C}$ receptor is closely related with weight gain.

The distribution of $D_3$ receptor in brain mainly locates specifically at limbic system and there are two major DA neural pathways in brain: one is nigrostriatal pathway regulating the motion function, while the other is mesencephalic ventral tegmental area-accumbens nucleus-prefrontal cortex DA pathway, which is closely associated with learning cognition and emotion behavior, and its disorder will lead to schizophrenia. This DA pathway is the main pathway of reward effect in brain. D3R is distributed in both of the DA neural pathways, and has complex interaction with other DA receptor subtypes, and thus may be the target of anti-psychosis drug therapy. Antagonism of selective $D_3$ receptor can reduce the negative and cognitive symptoms of schizophrenia, which can additionally prevent extrapyramidal system side effects, including tardive dyskinesia, Parkinson's disease or the like.

Therefore, it is important for clinical treatment to find novel anti-schizophrenia drug which can bind to multiple receptors and has less side effects.

SUMMARY

In a first aspect, provided is a compound of Formula (I) or a pharmaceutically acceptable salt or prodrug thereof,

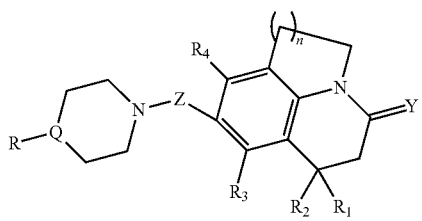

(I)

wherein,

Z is —$(CH_2)_m$—, which is unsubstituted or substituted by one or more substituents selected from the group consisting of hydroxy, carbonyl and $C_{1-5}$ alkyl (e.g. methyl), m is an integer of 2~5;

Y is O or S;
Q is N or CH;
n=1, 2 or 3;
$R_1$, $R_2$, $R_3$ or $R_4$ is each independently hydrogen, halogen, $C_{1-5}$ alkyl, wherein the $C_{1-5}$ alkyl is unsubstituted or substituted by one or more substituents selected from the group consisting of halogen, amino and hydroxy;
R is phenyl, or a group of Formula (II), Formula (III) or Formula (IV), wherein the above groups are unsubstituted or substituted by one or more substituents selected from the group consisting of halogen, cyano, $C_{1-5}$ alkyl, $C_{1-5}$ alkoxyl (e.g. methoxyl) and hydroxy;

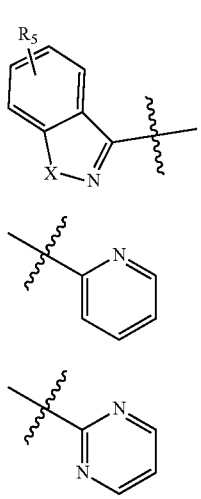

(II)

(III)

(IV)

wherein, X in Formula (II) is O or S; $R_5$ is H or halogen.

In a preferable embodiment, Z in Formula (I) is —$(CH_2)_m$—, which is unsubstituted or substituted by one or more substituents selected from the group consisting of hydroxy, carbonyl and methyl, m is an integer of 2~5.

In another preferable embodiment, halogen is fluorine, chlorine, bromine or iodine.

In another preferable embodiment, R in Formula (I) is a group of Formula (II), wherein, when X is O, $R_5$ is selected from the group consisting of fluorine, chlorine, bromine and iodine; when X is S, $R_5$ is hydrogen.

In another preferable embodiment, R in Formula (I) is phenyl, which is substituted by one or more substituents selected from the group consisting of methoxyl, methyl, ethyl, fluoroethyl, fluorine, chlorine, bromine, iodine and cyano.

In another preferable embodiment, $R_1$, $R_2$, $R_3$ or $R_4$ in Formula (I) is each independently hydrogen, phenyl, halogenated phenyl, $C_{1-5}$ alkyl, halogenated $C_{1-5}$ alkyl or $C_{1-5}$ hydroxyalkyl; preferably, $R_1$, $R_2$, $R_3$ or $R_4$ is each independently hydrogen, fluorine, phenyl, methyl, ethyl, propyl, trifluoromethyl or hydroxymethyl.

In another preferable embodiment, Z in Formula (I) is —$(CH_2)_m$—, which is unsubstituted or substituted by one or more substituents selected from the group consisting of hydroxy and carbonyl, m is an integer of 2~5.

In a further preferable embodiment, in Formula (I),
Y is O or S;
Q is N or CH;
n=1, 2 or 3;
$R_1$, $R_2$, $R_3$ or $R_4$ is each independently hydrogen, fluorine, phenyl, methyl, ethyl or propyl;
R is phenyl, a group of Formula (III) or a group of Formula (IV); or
R is a group of Formula (II), wherein, when X is O, $R_5$ is selected from the group consisting of fluorine and chlorine, or when X is S, $R_5$ is hydrogen; or
R is phenyl, which is substituted by one or more substituents selected from the group consisting of methoxyl, methyl, ethyl, fluoroethyl, fluorine, chlorine, bromine and cyano.

Particularly, provided is at least one of the following compounds, or the stereisomer, tautomer, nitrogen oxide, solvate, metabolite, pharmaceutically acceptable salt or prodrug thereof:

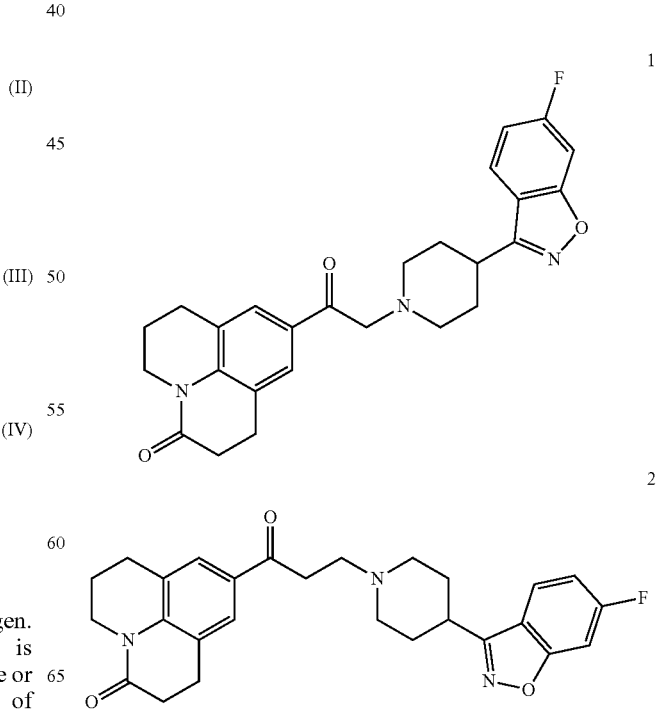

3
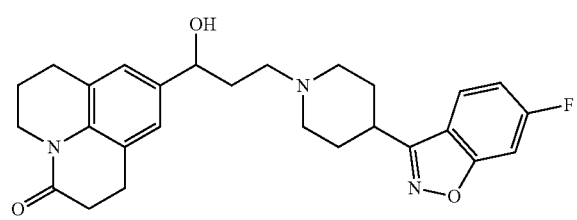
4
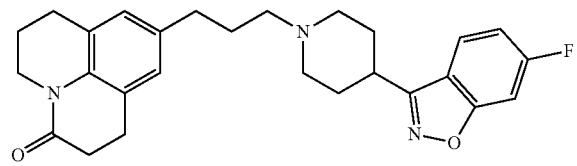
5
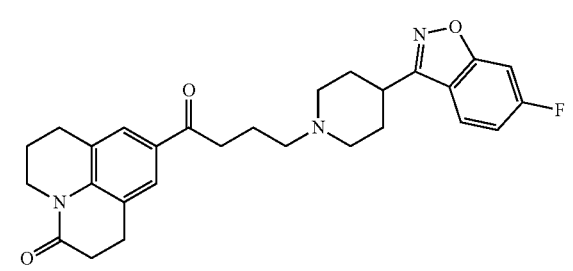 [SMILES: O=C(CCCN1CCC(c2noc3cc(F)ccc23)CC1)c1cc2c3c(c1)CCC(=O)N3CCC2]
6
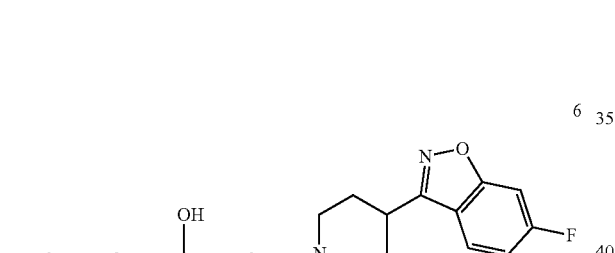
7
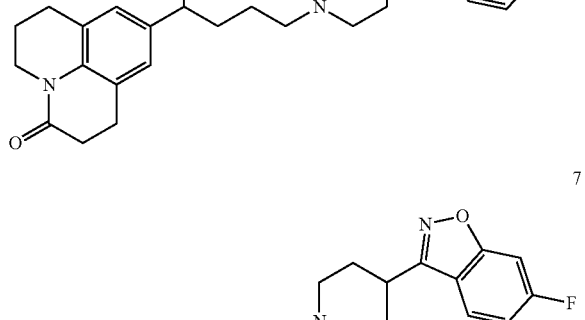
8
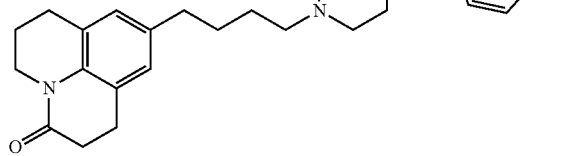
9
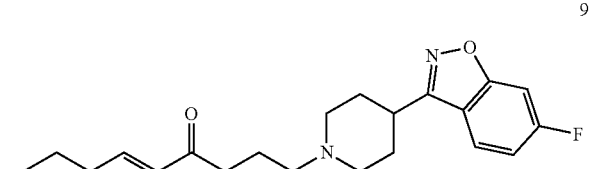
10
11
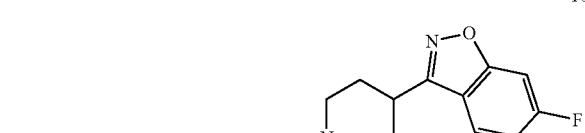
12
13
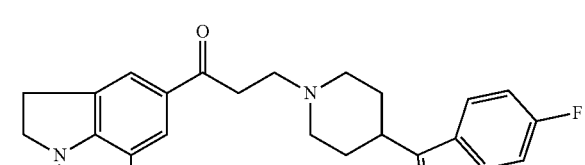
14
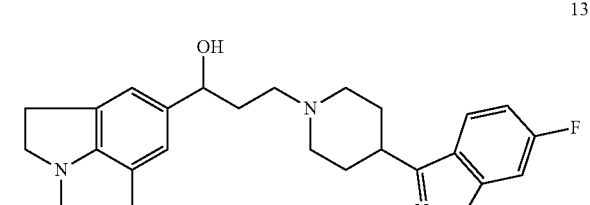

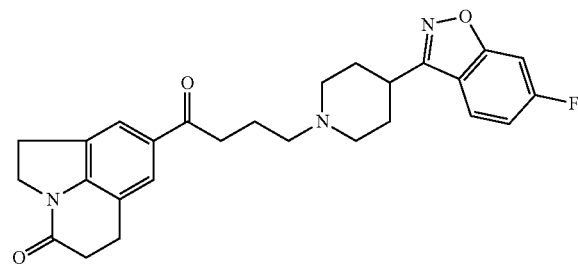
15
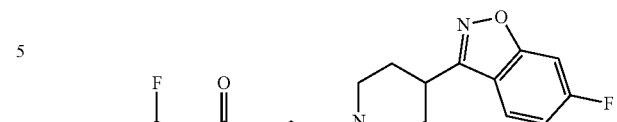
21
16
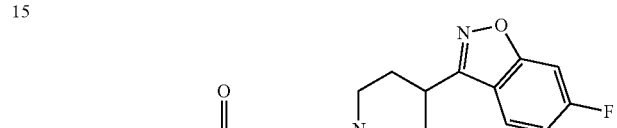
22
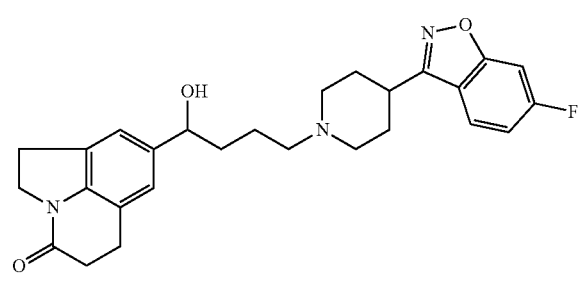
17
23
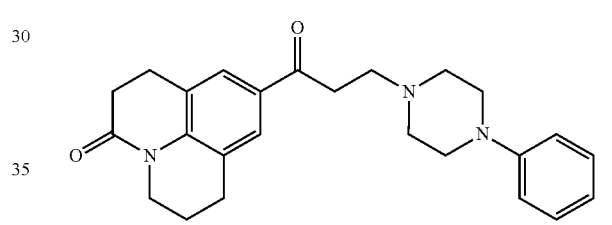
18
24
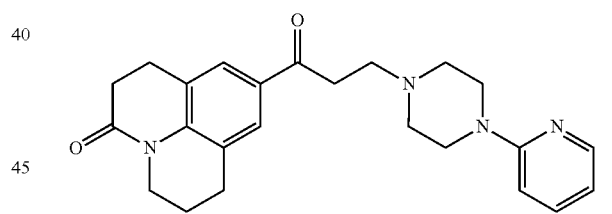
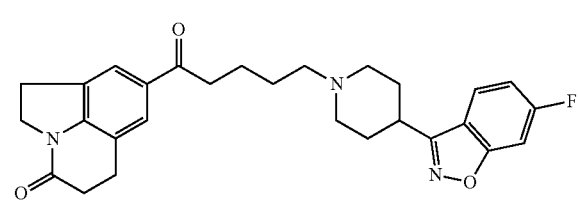
25
19
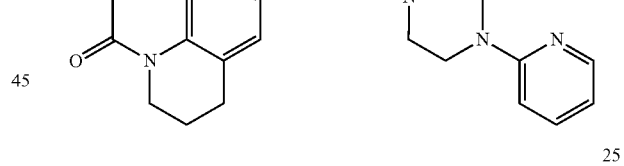
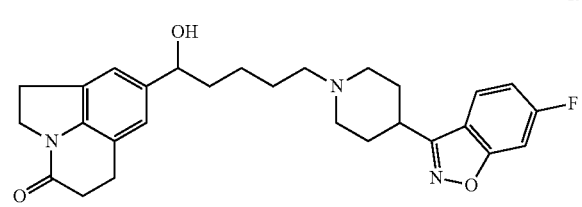
26
20
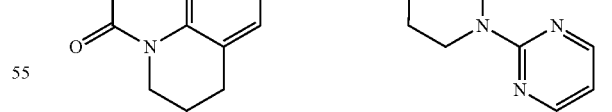
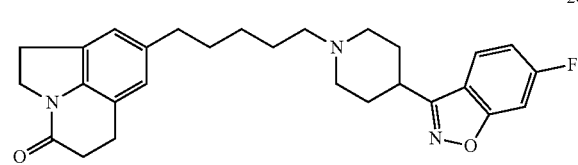
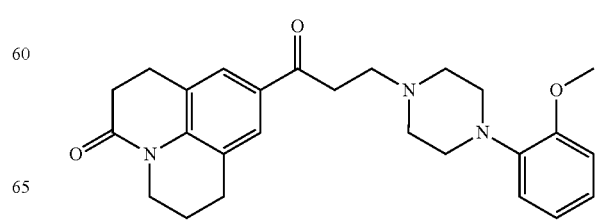

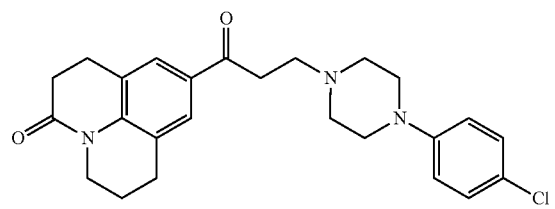

38
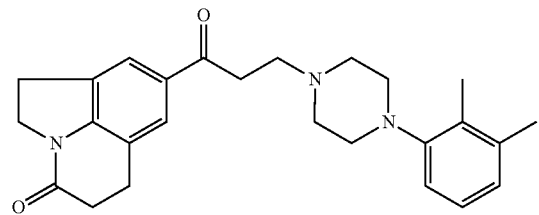
39
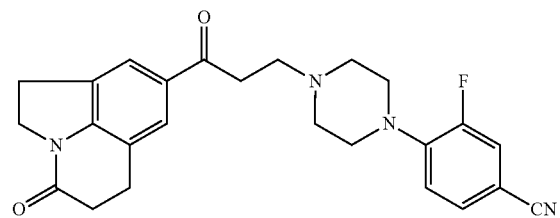
40
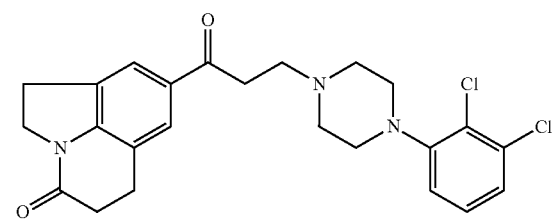
41
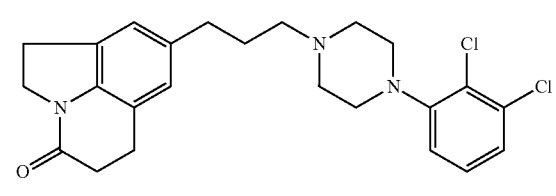
42
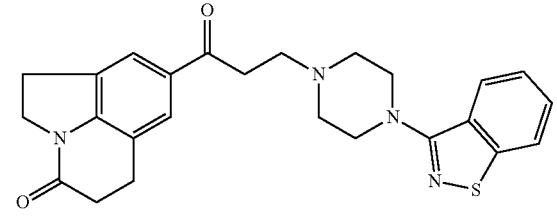
43
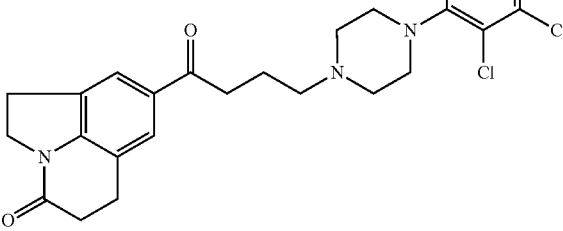
44
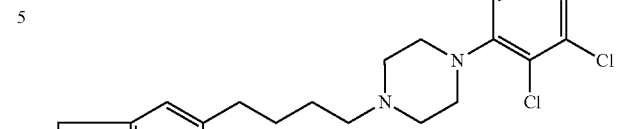
45
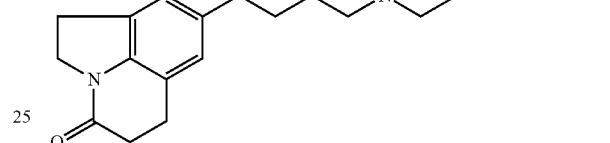
46
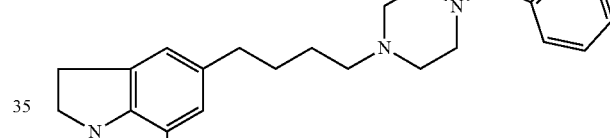
47
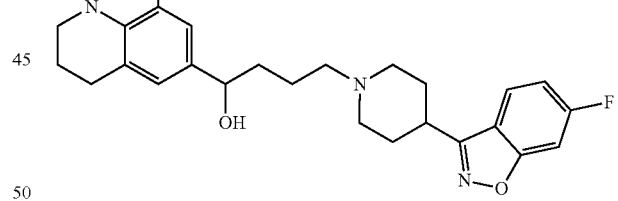
48
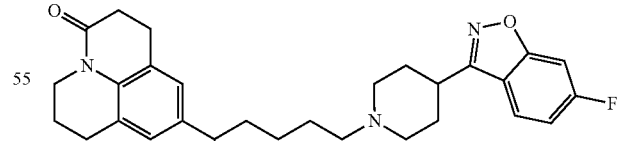
49
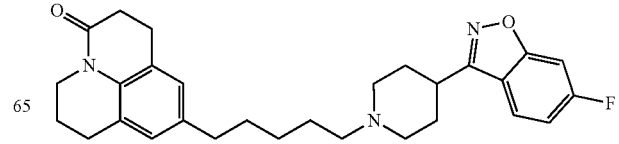

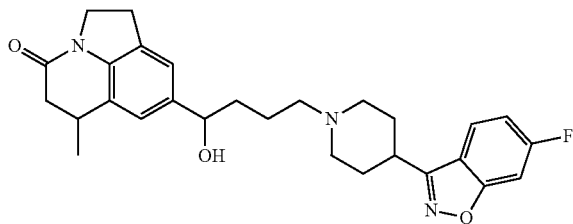

50

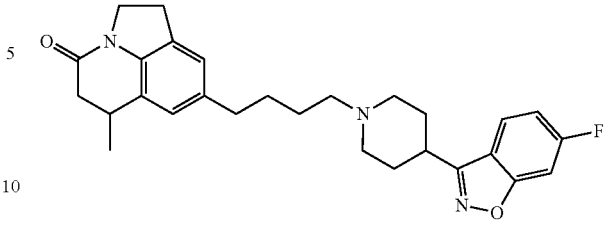

56

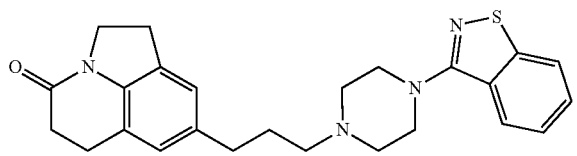

51

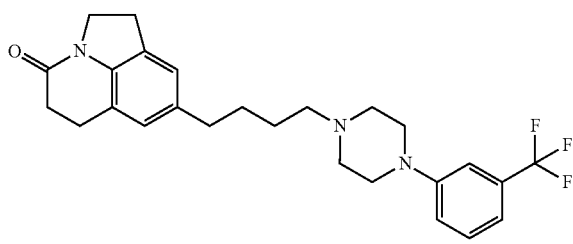

52

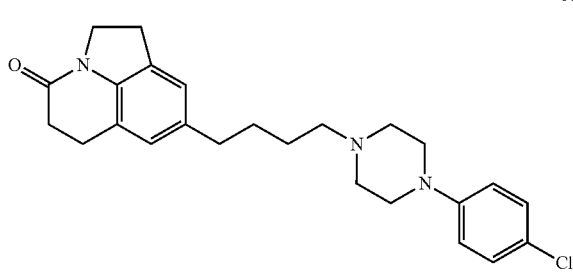

53

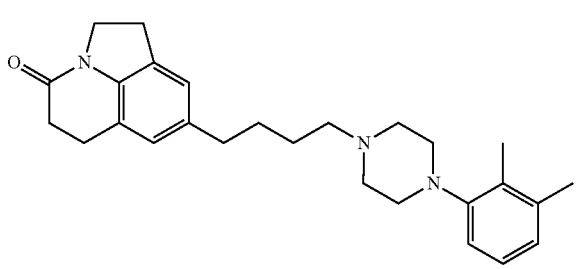

54

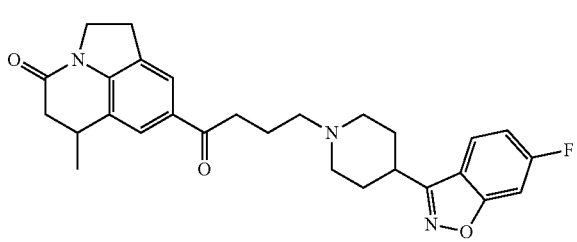

55

In a second aspect, also provided is a pharmaceutical composition, which comprises a compound or a pharmaceutically acceptable salt or prodrug thereof according to the invention, and optionally further comprises pharmaceutically acceptable excipient, carrier, adjuvant, solvent or the combination thereof.

In a third aspect of the invention, provided is a compound or a pharmaceutically acceptable salt or a prodrug thereof according to the invention or a pharmaceutical composition according to the invention for use in the prevention or treatment of psychiatric disease.

Provided is also a method for the prevention or treatment of psychiatric disease, comprising administrating a subject in need thereof a compound or a pharmaceutically acceptable salt or a prodrug thereof according to the invention or a pharmaceutical composition according to the invention in an effective amount.

Provided is also use of a compound or a pharmaceutically acceptable salt or a prodrug thereof according to the invention or a pharmaceutical composition according to the invention in the manufacture of a medicament for the treatment or prevention of psychiatric disease.

Preferably, the psychiatric disease is schizophrenia.

DETAILED DESCRIPTION OF THE INVENTION

Definitions and General Terms

Unless indicated otherwise, definitions used herein should be adopted as follows. For the purpose of the invention, chemical elements should be consistent with the CAS version of Periodic Table of Elements and *Handbook of Chemistry and Physics* (the 75th edition, 1994). In addtion, general principles of organic chemistry may refer to "*Organic Chemistry*", Thomas Sorrell, University Science Books, Sausalito: 1999 and "*March's Advanced Organic Chemistry*", Michael B. Smith and Jerry March, John Wiley & Sons, New York: 2007, which are incorporated herein by reference in their entirety.

The term "patient" or "subject" used in the invention refers to human (including adult and child) or other animal (including mammal). According to some examples of the invention, "patient" or "subject" refers to human.

The term "optional" or "optionally" or "optionally exist" means the event described subsequent thereto may, but not necessarily happen, and the description includes the cases wherein the said event or circumstance happens or does not happen. For example, "a bond optionally exists" refers to a bond which may exist or not exist, and the description includes single bond, double bond or triple bond.

The term "comprise" is an open-ended expression manner, i.e. including the content indicated in the invention without excluding content of other aspects. It is understood that, the term "comprise" may encompass the interpretation of the close-ended manner, i.e. "consist of".

The term "unsaturation" or "unsaturated" refers to a molecule which partially contains one or more unsaturation.

As described in the invention, the compound of the invention, like compound of the above-mentioned general formula or the embodiments and subtypes in the examples, may be optionally substituted by one or more substituents. It should be understood that the term "optionally substituted" can be exchangeably used with the term "substituted or unsubstituted". Generally, the term "substituted" means that one or more hydrogen atoms in the given structure are substituted by a given substituent. Unless stated in other aspects, the optionally substituted group can be substituted at each substitutable site on the group. When more than one site in the given structure can be substituted by one or more substituents selected from the group consisting of given groups, each site can be substituted by the same or different substituents.

It should be noted that, unless otherwise indicated clearly, the description "each independently" used herein should be understood in a broad sense. It may mean that the specific options denoted by the same symbol in different groups have no influence upon each other, or may also mean that the specific options denoted by the same symbol in the same group have no influence upon each other.

In the sections of the description, substituents of the compound of the invention are disclosed according to the types and scopes of the groups. It should be particularly indicated that, every independent subordinated combination of the types and scope of these groups are encompassed by invention. For example, the term "$C_{1-5}$ alkyl" particularly means independently disclosed methyl, ethyl, $C_3$ alkyl, $C_4$ alkyl and $C_5$ alkyl. Examples of the alkyl groups include but are not limited to methyl (Me, —$CH_3$), ethyl (Et, —$CH_2CH_3$), n-propyl (n-Pr, —$CH_2CH_2CH_3$), iso-propyl (i-Pr, —$CH(CH_3)_2$), n-butyl (n-Bu, —$CH_2CH_2CH_2CH_3$), iso-butyl (i-Bu, —$CH_2CH(CH_3)_2$), secondary butyl (s-Bu, —$CH(CH_3)CH_2CH_3$), tertiary butyl (t-Bu, —$C(CH_3)_3$), n-pentyl (—$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), n-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), n-heptyl, n-octyl, etc.

The term "carbonyl", either used alone or in combination with other terms, for example "amino carbonyl" or "acyloxy", refers to —(C=O)—. It is understood by a person skilled in the art that, substitution by a carbonyl group may also mean hydrogen atoms on an carbon atom (for example two hydrogen atoms on a carbon atom) which are substituted with oxygen group (=O) to form a carbonyl.

The ranges described herein (like numerical ranges) may include every value within the range, and every subrange formed by each value. Therefore, the phrase "m is an integer of 2~5" includes for example an integer of 2~4, an integer of 3~5, etc., e.g., 2, 3, 4 or 5.

The phrase "one or more" can mean 1, 2, 3, 4, 5, 6 or more.

The term "hydrogen (H)" refers to a single hydrogen atom. Such radical can be attached with other groups, for example attached with oxygen atom to form hydroxy group.

The term "halogen" refers to fluorine (F), chlorine (Cl), bromine (Br) or iodine (I).

The term "alkoxyl" refers to an alkyl group attached to the rest of the molecule through oxygen atom, wherein the alkyl group has the meaning defined in the invention. Unless specifically indicated otherwise, the alkoxyl group may contain 1 to 12 carbon atoms. According to an embodiment of the invention, alkoxyl group may contain 1 to 6 carbon atoms. According to another embodiment of the invention, alkoxyl group may contain 1 to 5 or 1 to 4 carbon atoms. According to another embodiment of the invention, alkoxyl group may contain 1 to 3 carbon atoms. The alkoxyl group is optionally substituted by one or more substituents described in the invention.

Examples of alkoxyl group include, but are not limited to, methoxyl (MeO, —$OCH_3$), ethyoxyl (EtO, —$OCH_2CH_3$), 1-propoxy (n-PrO, n-propoxy, —$OCH_2CH_2CH_3$), 2-propoxy (i-PrO, i-propoxy, —$OCH(CH_3)_2$), 1-butoxy (n-BuO, n-butoxy, —$OCH_2CH_2CH_2CH_3$), 2-methyl-1-propoxy (i-BuO, i-butoxy, —$OCH_2CH(CH_3)_2$), 2-butoxy (s-BuO, s-butoxy, —$OCH(CH_3)CH_2CH_3$), 2-methyl-2-propoxy (t-BuO, t-butoxy, —$OC(CH_3)_3$), 1-pentyloxy (n-pentyloxy, —$OCH_2CH_2CH_2CH_2CH_3$), 2-pentyloxy (—$OCH(CH_3)CH_2CH_2CH_3$), 3-pentyloxy (—$OCH(CH_2CH_3)_2$), 2-methyl-2-butoxy (—$OC(CH_3)_2CH_2CH_3$), 3-methyl-2-butoxy (—$OCH(CH_3)CH(CH_3)_2$), 3-methyl-1-butoxy (—$OCH_2CH_2CH(CH_3)_2$), 2-methyl-1-butoxy (—$OCH_2CH(CH_3)CH_2CH_3$), etc.

The term "cycle" includes carbon cycle, heterocycle, aromatic ring, heteroaromatic ring, etc., wherein the carbon cycle, heterocycle, aromatic ring, heteroaromatic ring group have the meaning defined herein.

The term "cycloalkyl" refers to a saturated monocyclic, bicyclic or tricyclic system, which is monovalent or multivalent, and contains 3 to 12 carbon atoms. The bicyclic or tricyclic system may include fused ring, bridged ring and spiro ring. According to an embodiment of the invention, cycloalkyl may comprise 3 to 10 carbon atoms. According to another embodiment of the invention, cycloalkyl may comprise 3 to 8 carbon atoms. According to another embodiment of the invention, cycloalkyl may comprise 3 to 6 carbon atoms. Examples of cycloalkyl group include, but are not limited to, cyclopropyl, cyclobutyl, cyclopentyl, cyclohexyl, etc. The cycloalkyl group is optionally substituted by one or more substituents described in the invention.

The term "aryl" refers to a monocyclic, bicyclic or tricyclic carbocycle system, containing 6 to 14 ring atoms, or 6 to 12 ring atoms, or 6 to 10 ring atoms, wherein at least one cycle is aromatic. The aryl group is connected with the parent molecular, generally but not necessarily through the aromatic cycle of aryl group. Examples of aryl group can include phenyl, naphthyl and anthracene. The aryl group is optionally substituted by one or more substituents described in the invention.

The term "prodrug" used in the invention refers to a compound that can be transformed in vivo into the compound of Formula (I). Such transformation is affected by hydrolysis of the drug precursor in blood or the enzymic transformation of the drug precursor in blood or tissue to the parent molecule. The following literature may be the reference for a detailed discussion of the drug precursor: Higuchi et al., *Pro-drugs as Novel Delivery Systems*, Vol. 14, A.C.S. Symposium Series; Roche et al., ed., *Bioreversible Carriers in Drug Design*, American Pharmaceutical Association and Pergamon Press, 1987; Rautio et al., *Prodrugs: Design and Clinical Applications*, Nature Reviews Drug Discovery, 2008, 7, 255-270, and Hecker et al, *Prodrugs of Phosphates and Phosphonates*, J. Med. Chem., 2008, 51, 2328-2345. The disclosure of each literature is incorporated herein by reference in its entirety.

The term "metabolite" used herein refers to the product obtained in vivo by metabolism of a specific compound or the salt thereof. A metabolite of a compound can be identified using technologies in the common knowledge of the art, the activity thereof can be characterized using experimental methods described in the invention. Such product may be obtained from the administered compound by methods like oxidation, reduction, hydrolysis, amidation, de-amidation, esterification, de-esterification, enzyme cleavage, etc. Accordingly, the metabolite of the compound of the invention is encompassed by the invention, for example the metabolite produced by sufficiently contacting the compound of the invention with a mammal for a period of time. It is understood that, the stereoisomer, tautomer, nitrogen oxide, solvate (e.g. hydrate), metabolite, and the like, of the compound of the invention or the salt thereof, is also encompassed by the invention. These forms are preferably pharmaceutically acceptable.

"Pharmaceutically acceptable salt" used herein refers to an organic salt and an inorganic salt of the compound of the invention. The pharmaceutically acceptable salt is known to a person skilled in the art, like those recited in the literature: S. M. Berge et al., J. Pharmaceutical Sciences, 66: 1-19, 1977. Pharmaceutically acceptable salts formed by non-toxic acids include, but are not limited to, a salt formed by reaction with an inorganic acid, e.g. hydrochloride, hydrobromate, phosphate, sulfate, perchlorate; and a salt formed by reaction with an organic acid, e.g. acetate, oxalate, maleate, tartrate, citrate, succinate, malonate, or a salt obtained through other methods recited in the literatures, like ion exchange. Other pharmaceutically acceptable salts include but are not limited to adipate, alginate, ascorbate, aspartate, benzenesulphonate, benzoate, bisulphate, borate, butyrate, camphorate, camphorsulfonate, cyclic pentyl propionate, digluconate, dodecyl sulfates, ethanesulfonate, formate, fumarate, glucoheptonate, glycerin phosphate, glyconate, hemisulphate, heptylate, hexanoate, hydriodate, 2-hydroxy-ethanesulfonate, lactobionate, lactate, laurate, lauryl sulfate, malate, malonate, methanesulfonate, 2-naphthalenesulfonate, nicotinate, nitrate, oleate, palmitate, pamoate, pectate, persulphate, 3-phenylpropionate, picrate, pivalate, propionate, stearate, thiocyanate, p-methylbenzenesulphonate, undecylate, valerate, etc. Salts obtained from suitable bases include but are not limited to salts of alkali metal, alkali-earth metal, ammonium and $N^+(C_{1-4}\text{ alkyl})_4$. Quaternary ammonium salt formed by any nitrogen-containing compound is also encompassed by the invention. Water-soluble or oil-soluble or dispersion product may be obtained by quaternization. The alkali metal or alkali-earth metal salts include sodium, lithium, potassium, calcium, magnesium salt, etc. The pharmaceutically acceptable salt further include ammonium cation formed by suitable non-toxic ammonium, quaternary ammonium salt and counterion, like halide, hydroxide, carboxylate, sulfate, phosphate, nitrate, $C_{1-8}$ sulfonate and aromatic sulfonate.

Beneficial Effect

The compound according to the invention has high affinities for $D_2$, $D_3$, $5HT_{1A}$ and/or $5HT_{2A}$, thereby has potential effect on improving the positive symptoms of schizophrenia, as well as the negative symptoms and cognitive disorders. Meanwhile, the compound according to the invention has low affinities for $5HT_{2C}$, $H_1$ and/or $\alpha_1$, and thus has the advantages of reduced bodyweight gain. Animal experiment shows that the compound of the invention has less extrapyramidal system side effects.

General Synthetic Scheme

The general synthetic method for the compound according to the invention may include: firstly, synthesizing the tricyclic fused core; secondly, reacting it with a linear chloro-acyl chloride; and thirdly, reacting it with the nitrogen terminal. For example:

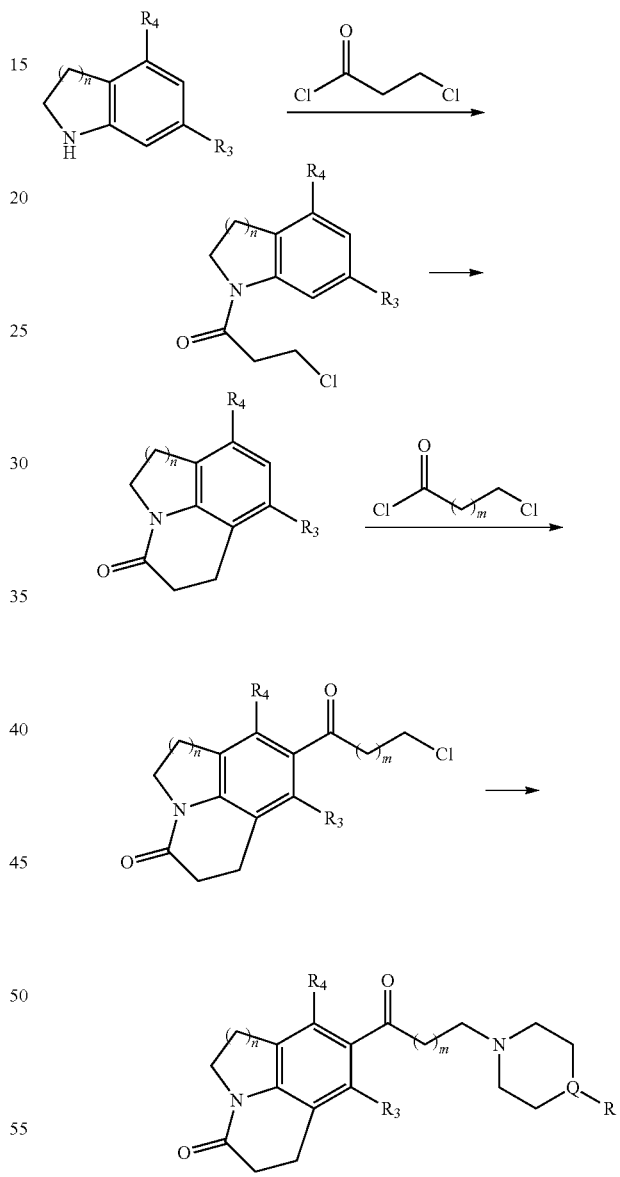

EXAMPLES

The specific examples of the invention are described below. The examples described below are exemplary, provided for the purpose of illustration to the invention only rather than limitation thereto. Unless defined otherwise, proportion and percentage are calculated based on weight herein.

SYNTHETIC EXAMPLES

Example 1

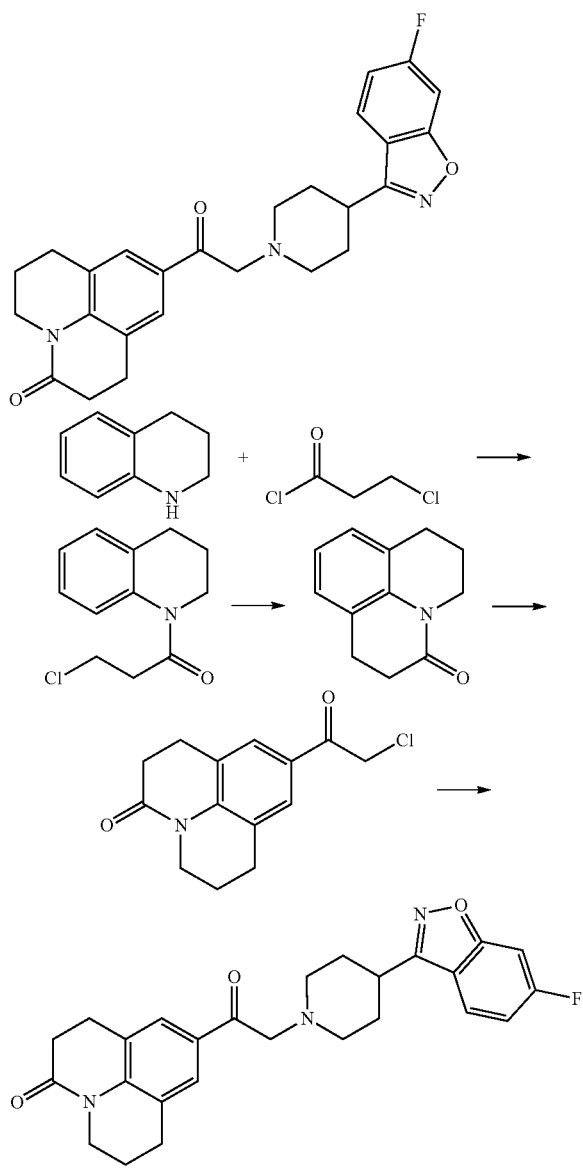

1) To 1,2,3,4-tetrahydroquinoline (5.0 g) was added acetone (50 ml), and then 3-chloropropionyl chloride (5.1 g) was added slowly. The reaction was heated to reflux with stirring. The reaction was completed after 4 hours. The reaction mixture was cooled to room temperature, and the reaction solution was concentrated. The residue was dissolved in ethyl acetate, washed with water, dried with anhydrous magnesium sulfate, filtered off with suction and concentrated to give 8.0 g of oil. Yield: 96.4%.

2) To the product (8 g) from the first step was added anhydrous aluminium trichloride (7.2 g). The mixture was heated with stirring and reacted for 3 hours. The reaction mixture was cooled to room temperature and ice water was added to quench the system. The reaction mixture was filtered, extracted with ethyl acetate, washed with water, dried with anhydrous magnesium sulfate, filtered off with suction and concentrated to give 6.05 g of solid. Yield: 90.3%.

3) To the product (5.0 g) from the second step was added 2-chloroacetyl chloride (2.30 mL) and 1,2-dichloroethane (25 mL). The system was cooled to about 0° C. in ice water bath. Anhydrous aluminium trichloride (7.2 g) was added in portions with the inner temperature kept at about 0° C. The temperature was kept for another 30 min after addition, then the ice water bath was removed and the reaction was performed at room temperature for 2 hours. Ice water was added to quench the system. The reaction mixture was filtered, extracted with ethyl acetate, washed with water, dried with anhydrous magnesium sulfate, filtered off with suction and concentrated. Column chromatography (PE:EA=6:1) was performed to give 6.75 g of solid. Yield: 80.0%.

4) To the product (0.66 g) from the third step was added 6-fluoro-3-(4-piperidyl)-1,2-benzisoxazole hydrochloride (0.52 g), anhydrous potassium carbonate (1 g), potassium iodide (0.2 g) and acetonitrile (25 ml). The mixture was heated under reflux and reacted for 12 hours. After cooling the reaction mixture to room temperature, the solvent was evaporated. An appropriate amount of dichloromethane was added to the system. Water washing was performed, and then the water layer was separated and discarded. The organic layer was dried with anhydrous magnesium sulfate. The solvent was evaporated to dryness to give light yellow oil. Column chromatography was performed to give 0.65 g of white solid.

1H NMR (600 MHz, CDCl3) δ 7.81 (s, 1H), 7.77 (s, 1H), 7.72 (dd, J=8.7, 5.1 Hz, 1H), 7.25-7.22 (m, 1H), 7.05 (ddd, J=9.0, 7.9, 2.0 Hz, 1H), 5.31 (s, 2H), 4.14 (t, J=8.5 Hz, 3H), 3.84 (s, 2H), 3.24 (t, J=8.5 Hz, 2H), 3.16 (d, J=11.5 Hz, 2H), 3.04 (t, J=7.8 Hz, 2H), 2.73 (t, J=7.8 Hz, 2H), 2.45-2.38 (m, 2H), 2.24-2.15 (m, 2H), 2.09 (d, J=12.6 Hz, 2H). MS (ESI) m/z 448.6 ([M+H]$^+$)

Example 2

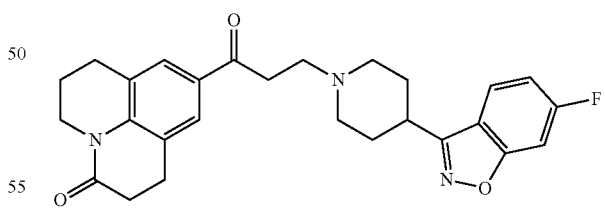

The target compound was prepared according to the method of Example 1, using 3-chloropropionyl chloride instead of 2-chloroacetyl chloride.

1H NMR (600 MHz, CDCl3) δ 7.76 (s, 1H), 7.72 (s, 1H), 7.21-7.11 (m, 2H), 7.03-6.86 (m, 1H), 3.93 (dt, J=12.9, 6.4 Hz, 4H), 3.42 (t, J=6.8 Hz, 2H), 3.20 (t, J=7.3 Hz, 2H), 3.11 (s, 4H), 3.05-2.89 (m, 2H), 2.87 (d, J=6.2 Hz, 2H), 2.79-2.65 (m, 2H), 2.05-1.92 (m, 3H).

MS (ESI) m/z 462.5 ([M+H]$^+$)

Example 3

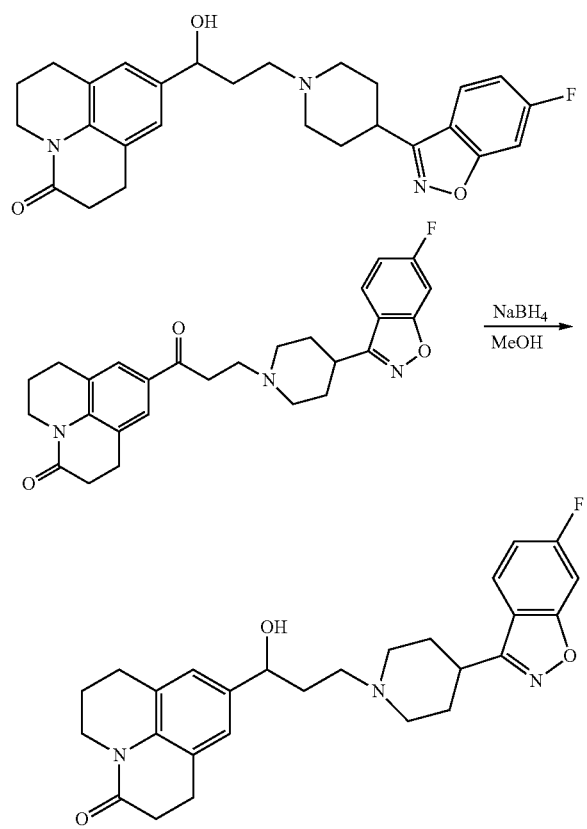

The target compound of Example 2 (0.5 g) was dissolved in anhydrous methanol (20 mL). The reaction mixture was cooled to 0° C. in ice water bath, and sodium borohydride (0.08 g) was added. Then the reaction was stirred for another 1 h. The reaction was quenched by adding 10 mL of water. The solvent was evaporated to dryness and an appropriate amount of dichloromethane was added. Water washing was performed, and then the water layer was separated and discarded. The organic layer was dried with anhydrous magnesium sulfate. The solvent was evaporated to dryness to give light yellow oil. Column chromatography was performed to give 0.40 g of white solid.

1H NMR (600 MHz, CDCl3) δ 7.71 (dt, J=11.6, 5.8 Hz, 1H), 7.68 (s, 1H), 7.66 (s, 1H), 7.26 (dd, J=8.5, 2.0 Hz, 1H), 7.12-7.02 (m, 1H), 3.94-3.88 (m, 2H), 3.20 (t, J=7.3 Hz, 2H), 3.10 (dd, J=15.3, 7.3 Hz, 3H), 3.00-2.95 (m, 2H), 2.92 (t, J=7.3 Hz, 2H), 2.87 (t, J=6.2 Hz, 2H), 2.73-2.69 (m, 2H), 2.30 (t, J=12.5 Hz, 2H), 2.14-2.05 (m, 4H), 1.99 (dt, J=12.1, 6.1 Hz, 2H), 1.86-1.80 (m, 2H). MS (ESI) m/z 464.7 ([M+H]$^+$)

Example 4

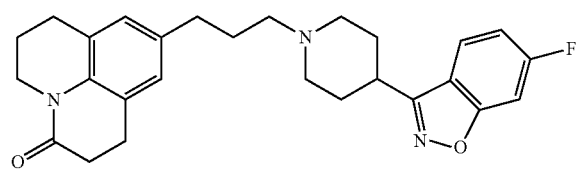

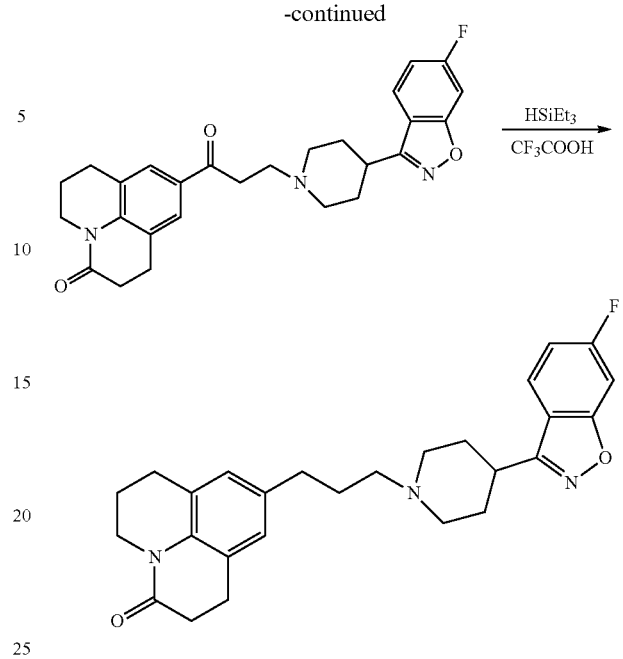

The target compound of Example 2 (0.5 g) was dissolved in trifluoroacetic acid (20 mL), and then triethyl silicane (0.10 g) was added slowly to the mixture. Agitation was performed overnight at room temperature. The solvent was evaporated to dryness and an appropriate amount of dichloromethane was added. Washing with saturated NaHCO$_3$ solution was performed. The water layer was separated and discarded. The organic layer was dried with anhydrous magnesium sulfate. The solvent was evaporated to dryness to give light yellow oil. Column chromatography was performed to give 0.35 g of transparent colorless oil.

1H NMR (600 MHz, CDCl3) δ 7.71 (dt, J=11.6, 5.8 Hz, 1H), 7.68 (s, 1H), 7.66 (s, 1H), 7.26 (dd, J=8.5, 2.0 Hz, 1H), 7.12-7.02 (m, 1H), 3.94-3.88 (m, 2H), 3.20 (t, J=7.3 Hz, 2H), 3.10 (dd, J=15.3, 7.3 Hz, 3H), 3.00-2.95 (m, 2H), 2.92 (t, J=7.3 Hz, 2H), 2.87 (t, J=6.2 Hz, 2H), 2.73-2.69 (m, 2H), 2.30 (t, J=12.5 Hz, 2H), 2.14-2.05 (m, 4H), 1.99 (dt, J=12.1, 6.1 Hz, 2H), 1.86-1.80 (m, 2H). MS (ESI) m/z 448.5 ([M+H]$^+$)

Example 5

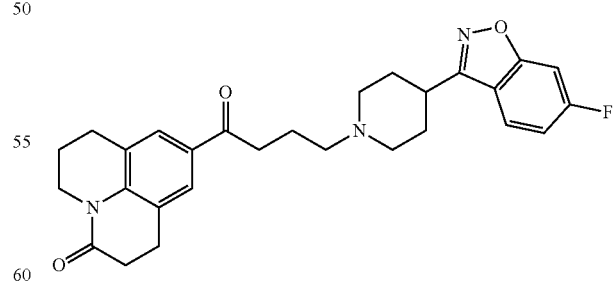

The target compound was prepared according to the method of Example 1, using 4-chlorobutyryl chloride instead of 2-chloroacetyl chloride.

1H NMR (600 MHz, CDCl3) δ 7.66 (s, 1H), 7.65 (s, 1H), 7.29 (s, 1H), 7.27 (d, J=7.9 Hz, 1H), 7.14 (tt, J=12.4, 6.2 Hz, 1H), 3.95-3.87 (m, 2H), 3.21 (t, J=6.2 Hz, 2H), 3.49-3.40

(m, 3H), 3.07-3.00 (m, 3H), 3.00-2.92 (m, 3H), 2.86 (t, J=6.1 Hz, 3H), 2.72-2.65 (m, 3H), 2.33-2.30 (m, 3H), 1.98-195 (m, 3H). MS (ESI) m/z 476.9 ([M+H]⁺)

Example 6

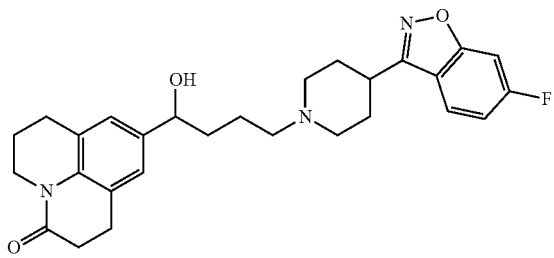 [SMILES: O=C1CCc2cc(C(O)CCCN3CCC(c4noc5cc(F)ccc45)CC3)cc3c2N1CCC3]

The target compound was prepared according to the method of Example 3, using the target compound of Example 5 instead of the target compound of Example 2.

1H NMR (600 MHz, CDCl3) δ 7.75 (dd, J=8.7, 5.1 Hz, 1H), 7.26 (dd, J=8.4, 2.0 Hz, 1H), 7.10-7.03 (m, 3H), 4.67-4.55 (m, 1H), 3.95-3.82 (m, 2H), 3.16 (dd, J=87.8, 29.3 Hz, 2H), 2.95-2.85 (m, 2H), 2.83-2.78 (m, 2H), 2.66 (dd, J=8.4, 6.5 Hz, 2H), 2.55 (t, J=5.1 Hz, 2H), 2.36 (s, 1H), 2.29-2.18 (m, 2H), 2.18-2.09 (m, 2H), 2.07-1.99 (m, 1H), 1.98-1.91 (m, 2H), 1.91-1.55 (m, 6H). MS (ESI) m/z 478.8 ([M+H]⁺)

Example 7

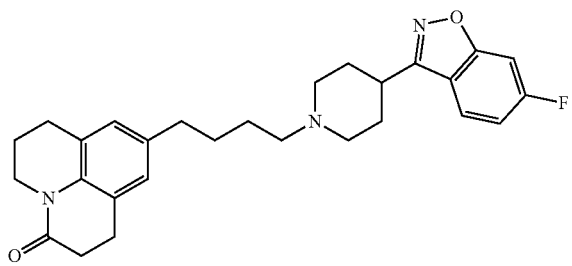 [SMILES: O=C1CCc2cc(CCCCN3CCC(c4noc5cc(F)ccc45)CC3)cc3c2N1CCC3]

The target compound was prepared according to the method of Example 4, using the target compound of Example 5 instead of the target compound of Example 2.

1H NMR (600 MHz, CDCl3) δ 7.72 (dd, J=8.5, 5.1 Hz, 1H), 7.26 (dd, J=8.4, 1.6 Hz, 1H), 7.07 (td, J=8.8, 1.7 Hz, 1H), 6.84 (d, J=1.9 Hz, 2H), 3.91-3.85 (m, 2H), 3.09 (d, J=9.2 Hz, 3H), 2.90-2.84 (m, 2H), 2.78 (t, J=6.2 Hz, 2H), 2.68-2.64 (m, 2H), 2.58 (t, J=7.4 Hz, 2H), 2.46-2.41 (m, 2H), 2.19-2.03 (m, 5H), 1.95 (dt, J=12.1, 6.2 Hz, 2H), 1.66-1.60 (m, 19.0 Hz, 5H). MS (ESI) m/z 462.7 ([M+H]⁺)

Example 8

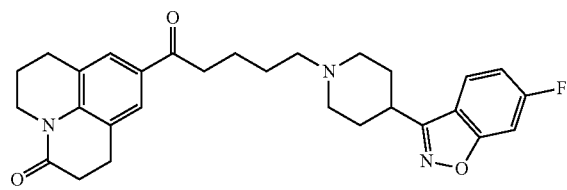 [SMILES: O=C(CCCCN1CCC(c2noc3cc(F)ccc23)CC1)c1cc2c3c(c1)CCC(=O)N3CCC2]

The target compound was prepared according to the method of Example 1, using 5-chlorovaleryl chloride instead of 2-chloroacetyl chloride.

1H NMR (600 MHz, CDCl3) δ 7.71 (dd, J=8.7, 5.1 Hz, 1H), 7.64 (s, 1H), 7.63 (s, 1H), 7.24 (dd, J=8.5, 2.1 Hz, 1H), 7.10-7.02 (m, 1H), 3.99-3.84 (m, 2H), 3.08 (d, J=10.0 Hz, 3H), 3.01-2.93 (m, 4H), 2.85 (t, J=6.2 Hz, 2H), 2.72-2.66 (m, 2H), 2.49-2.43 (m, 2H), 2.14 (dt, J=21.2, 8.7 Hz, 2H), 2.10-2.03 (m, 4H), 1.97 (dt, J=12.1, 6.1 Hz, 2H), 1.83-1.75 (m, 2H), 1.71-1.59 (m, 2H). MS (ESI) m/z 490.9 ([M+H]⁺)

Example 9

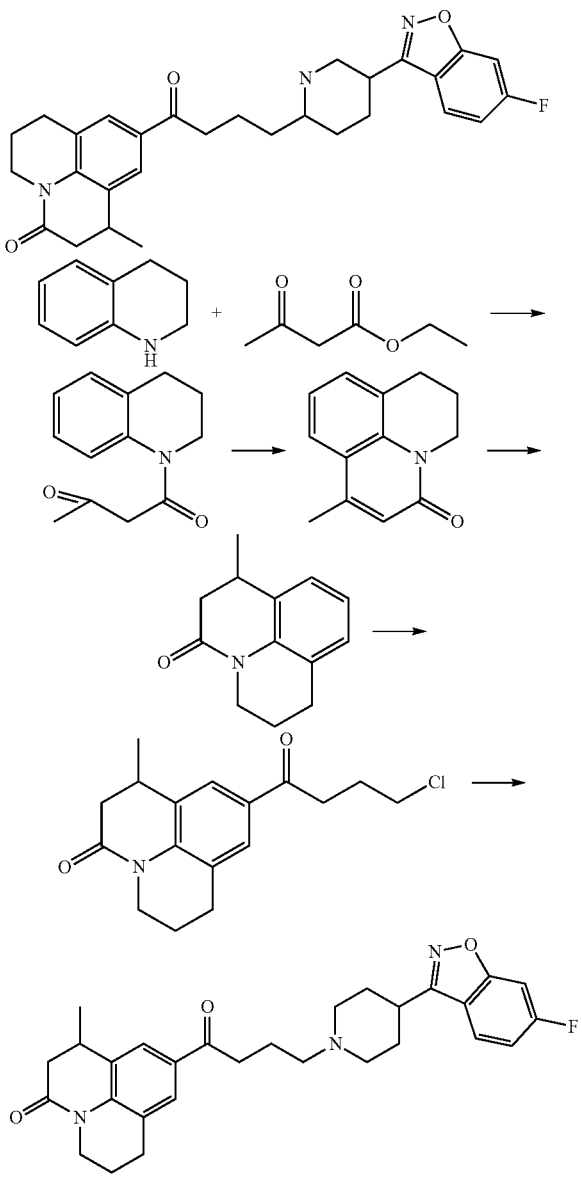

1) To 1,2,3,4-tetrahydroquinoline (10.0 g) was added ethyl acetoacetate (9.76 g), and then toluene (100 mL) was added. The mixture was refluxed overnight. After cooling down, the solvent was concentrated. The residue was dissolved in ethyl acetate, washed with 1 M hydrochloric acid subsequently, dried with anhydrous magnesium sulfate, filtered off with suction and concentrated to give 10.0 g of oil. Yield: 61.2%.

2) To the product (10 g) from the first step was added concentrated sulfuric acid (20 mL). The mixture was heated at 100° C. with stirring and reacted for 6 hours. After cooling to room temperature, ice water was added to quench the system. A solid was separated out, which was then filtered off with suction and dried to give 6.45 g of solid. Yield: 69.3%.

3) To the product (6.0 g) from the second step was added 10% Pd/C (0.12 g) and methanol (50 mL). Hydrogen gas was introduced at room temperature under atmospheric pressure, the reaction was completed after 6 hours. The mixture was filtered and the solvent was concentrated, extracted with ethyl acetate, washed with water, dried with anhydrous magnesium sulfate, filtered off with suction and concentrated. Column chromatography (PE:EA=6:1) was performed to give 5.45 g of solid. Yield: 90.0%.

4) To the product (5.0 g) from the third step was added 4-chlorobutyryl chloride (2.80 mL) and 1,2-dichloroethane (25 mL). The reaction mixture was cooled in ice water bath to about 0° C. Anhydrous aluminium trichloride (7.2 g) was added in batches, and inner temperature was kept at about 0° C. The temperature was kept for another 30 min after addition, and then the ice water bath was removed and the reaction was conducted at room temperature for 2 hours. Ice water was added to quench the system. The mixture was filtered, extracted with ethyl acetate, washed with water, dried with anhydrous magnesium sulfate, filtered off with suction and concentrated. Column chromatography (PE:EA=6:1) was performed to give 6.07 g of solid. Yield: 80.0%.

5) To the product from the fourth step (0.66 g) was added 6-fluoro-3-(4-piperidyl)-1,2-benzisoxazole hydrochloride (0.52 g), anhydrous potassium carbonate (1 g), potassium iodide (0.2 g) and acetonitrile (25 ml). The mixture was heated under reflux and reacted for 12 hours. After cooling the reaction mixture to room temperature, the solvent was evaporated to dryness and an appropriate amount of dichloromethane was added. Water washing was performed, and then the water layer was separated and discarded. The organic layer was dried with anhydrous magnesium sulfate. The solvent was evaporated to dryness to give light yellow oil. Column chromatography was performed to give 0.65 g of white solid.

1H NMR (600 MHz, CDCl3) δ 7.72 (dd, J=8.7, 5.1 Hz, 1H), 7.68 (s, 2H), 7.66 (s, 2H), 7.26 (dd, J=8.5, 2.0 Hz, 1H), 7.07 (td, J=8.8, 2.1 Hz, 1H), 3.98-3.81 (m, 2H), 3.24 (t, J=7.3 Hz, 2H), 3.15 (dd, J=13.6, 9.9 Hz, 3H), 2.96 (q, J=7.5 Hz, 4H), 2.87 (t, J=6.2 Hz, 2H), 2.70 (dd, J=8.4, 6.6 Hz, 2H), 2.35 (s, 2H), 2.20-2.11 (m, 4H), 1.99 (dt, J=12.2, 6.1 Hz, 2H). MS (ESI) m/z 490.7 ([M+H]+)

Example 10

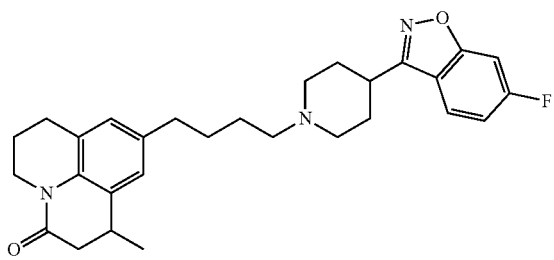 [SMILES: CC1CC(=O)N2CCCc3cc(CCCCN4CCC(c5noc6cc(F)ccc56)CC4)cc1c32]

The target compound was prepared according to the method of Example 4, using the target compound of Example 9 instead of the target compound of Example 2.

1H NMR (600 MHz, CDCl3) δ 7.74 (dd, J=8.6, 5.1 Hz, 1H), 7.26 (dd, J=8.4, 2.0 Hz, 1H), 7.08 (td, J=8.8, 2.1 Hz, 1H), 6.84 (d, J=2.4 Hz, 2H), 3.89-3.87 (m, 2H), 3.16 (d, J=10.8 Hz, 3H), 2.89-2.84 (m, 2H), 2.78 (t, J=6.2 Hz, 2H), 2.67-2.63 (m, 2H), 2.57 (dd, J=19.0, 12.1 Hz, 5H), 2.24-2.07 (m, 5H), 1.94 (dt, J=12.1, 6.1 Hz, 3H), 1.65 (s, 5H). MS (ESI) m/z 476.6 ([M+H]+)

Example 11

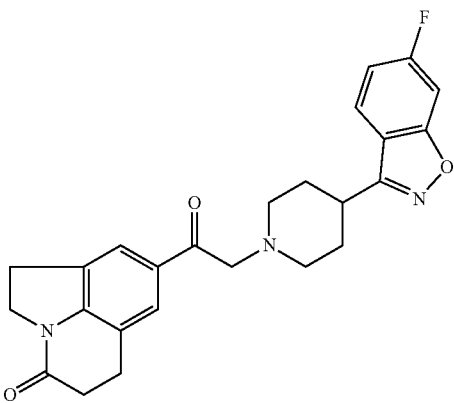 [SMILES: O=C(CN1CCC(c2noc3cc(F)ccc23)CC1)c1cc2c3c(c1)CCN3C(=O)CC2]

The target compound was prepared according to the method of Example 1, using indoline instead of 1,2,3,4-tetrahydroquinoline.

1H NMR (600 MHz, CDCl3) δ 7.74 (dd, J=8.8, 5.3 Hz, 2H), 7.70 (s, 1H), 7.26 (dd, J=8.5, 2.0 Hz, 1H), 7.07 (td, J=8.8, 2.0 Hz, 1H), 5.32 (s, 2H), 3.92-3.89 (m, 3H), 3.17 (dd, J=21.6, 7.7 Hz, 2H), 2.98-2.95 (m, 2H), 2.86 (t, J=6.1 Hz, 2H), 2.73-2.68 (m, 2H), 2.46 (t, J=11.0 Hz, 2H), 2.25-2.19 (m, 2H), 2.11 (d, J=12.0 Hz, 2H). MS (ESI) m/z 434.6 ([M+H]+)

Example 12

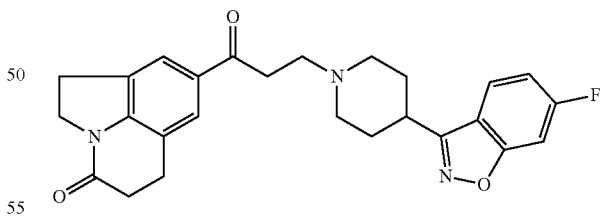

The target compound was prepared according to the method of Example 1, using indoline instead of 1,2,3,4-tetrahydroquinoline, and 3-chloropropionyl chloride instead of 2-chloroacetyl chloride.

1H NMR (600 MHz, CDCl3) δ 7.77 (s, 1H), 7.74-7.69 (m, 2H), 7.26 (dd, J=8.5, 2.0 Hz, 1H), 7.07 (td, J=8.8, 2.1 Hz, 1H), 4.16 (t, J=8.5 Hz, 2H), 3.26 (t, J=8.5 Hz, 2H), 3.20 (t, J=7.4 Hz, 2H), 3.13 (d, J=11.4 Hz, 3H), 3.05 (t, J=7.8 Hz, 2H), 2.92 (t, J=7.4 Hz, 2H), 2.74 (t, J=7.8 Hz, 2H), 2.29 (dd, J=14.0, 11.4 Hz, 2H), 2.18-2.04 (m, 4H). MS (ESI) m/z 448.6 ([M+H]+)

Example 13

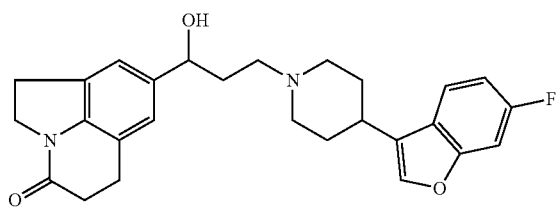 [SMILES: O=C1CCc2cc(C(O)CCN3CCC(c4coc5cc(F)ccc45)CC3)cc3c2N1CC3]

The target compound was prepared according to the method of Example 3, using the target compound of Example 12 instead of the target compound of Example 2.

1H NMR (600 MHz, CDCl3) δ 7.69 (dd, J=8.7, 5.1 Hz, 1H), 7.26 (dd, J=8.4, 2.0 Hz, 1H), 7.14 (s, 1H), 7.07 (dt, J=8.7, 3.0 Hz, 2H), 4.96-4.81 (m, 1H), 4.10 (t, J=8.4 Hz, 2H), 3.34 (s, 1H), 3.19 (dd, J=16.4, 8.0 Hz, 4H), 2.98 (t, J=7.8 Hz, 2H), 2.85-2.73 (m, 1H), 2.69 (t, J=7.7 Hz, 3H), 2.39 (s, 1H), 2.22-2.06 (m, 6H), 1.97-1.93 (m, 1H), 1.88-1.84 (m, 1H). MS (ESI) m/z 450.9 ([M+H]+)

Example 14

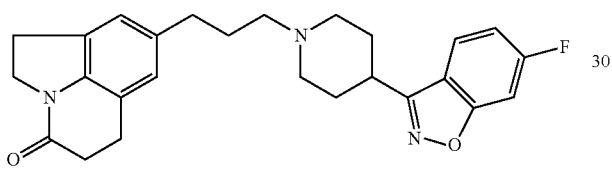

The target compound was prepared according to the method of Example 4, using the target compound of Example 12 instead of the target compound of Example 2.

1H NMR (600 MHz, CDCl3) δ 7.76 (s, 1H), 7.72 (s, 1H), 7.71-7.68 (m, 1H), 7.26-(dt, J=8.5, 2.0 Hz, 1H), 7.06 (td, J=8.8, 1.9 Hz, 2H), 4.15 (t, J=8.5 Hz, 2H), 3.25 (t, J=8.5 Hz, 2H), 3.18 (dt, J=13.1, 7.8 Hz, 3H), 3.09 (dt, J=22.0, 9.4 Hz, 4H), 3.04 (t, J=7.8 Hz, 2H), 2.91 (t, J=7.4 Hz, 2H), 2.74 (t, J=7.8 Hz, 2H), 2.30-2.26 (m, 2H), 2.15-2.06 (m, 4H). MS (ESI) m/z 434.7 ([M+H]+)

Example 15

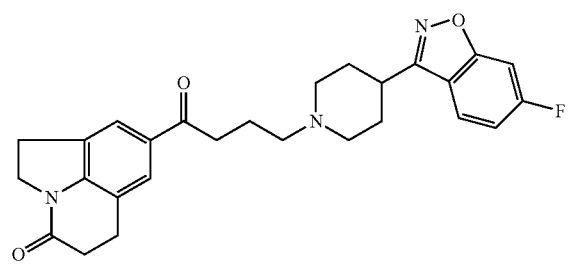 [SMILES: O=C(CCCN1CCC(c2noc3cc(F)ccc23)CC1)c1cc2c3c(c1)CCN3C(=O)CC2]

The target compound was prepared according to the method of Example 1, using indoline instead of 1,2,3,4-tetrahydroquinoline, and 4-chlorobutyryl chloride instead of 2-chloroacetyl chloride.

1H NMR (600 MHz, CDCl3) δ 7.70 (d, J=17.1 Hz, 1H), 7.67 (s, 1H), 7.62 (dt, J=9.3, 4.7 Hz, 1H), 7.17 (dt, J=8.3, 4.1 Hz, 1H), 7.00 (ddd, J=8.6, 6.4, 1.8 Hz, 1H), 4.08 (t, J=8.2 Hz, 2H), 3.19 (t, J=8.0 Hz, 2H), 3.05-2.90 (m, 7H), 2.67 (t, J=7.5 Hz, 2H), 2.44 (t, J=6.5 Hz, 2H), 2.12 (t, J=10.3 Hz, 2H), 2.04-1.89 (m, 6H). MS (ESI) m/z 462.8 ([M+H]+)

Example 16

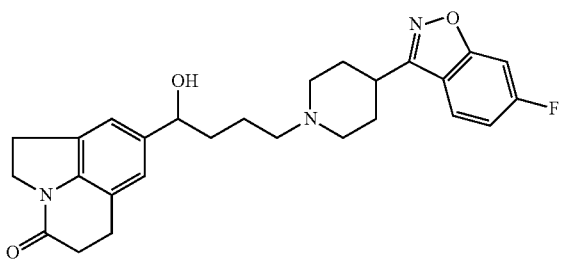 [SMILES: O=C1CCc2cc(C(O)CCCN3CCC(c4noc5cc(F)ccc45)CC3)cc3c2N1CC3]

The target compound was prepared according to the method of Example 3, using the target compound of Example 15 instead of the target compound of Example 2.

1H NMR (600 MHz, CDCl3) δ 7.76-7.74 (m, 1H), 7.2-7.24 (m, 1H), 7.14 (s, 1H), 7.08-7.04 (m, 2H), 4.66-4.63 (m, 1H), 4.08 (t, J=8.4 Hz, 2H), 3.18 (t, J=8.4 Hz, 4H), 2.97 (t, J=7.7 Hz, 4H), 2.68 (t, J=7.8 Hz, 2H), 2.59 (d, J=5.0 Hz, 2H), 2.29-2.18 (m, 2H), 2.21-2.09 (m, 4H), 2.03-1.91 (m, 2H), 1.87-1.72 (m, 2H). MS (ESI) m/z 464.7 ([M+H]+)

Example 17

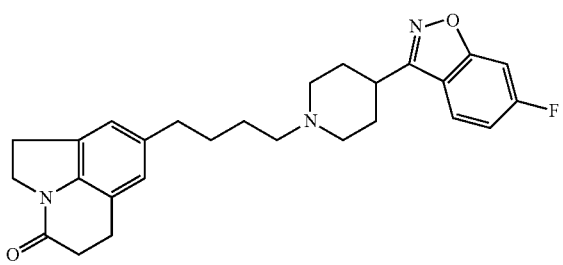 [SMILES: O=C1CCc2cc(CCCCN3CCC(c4noc5cc(F)ccc45)CC3)cc3c2N1CC3]

The target compound was prepared according to the method of Example 4, using the target compound of Example 15 instead of the target compound of Example 2.

1H NMR (600 MHz, CDCl3) δ 7.83 (d, J=7.2 Hz, 1H), 7.26 (dd, J=8.4, 1.9 Hz, 1H), 7.10 (td, J=8.8, 2.0 Hz, 1H), 6.92 (s, 1H), 6.83 (s, 1H), 4.08 (t, J=8.4 Hz, 2H), 3.42-3.23 (m, 3H), 3.18 (t, J=8.4 Hz, 2H), 2.96 (t, J=7.7 Hz, 2H), 2.68 (t, J=7.7 Hz, 4H), 2.62 (t, J=7.5 Hz, 4H), 2.33 (s, 4H), 1.76 (s, 2H), 1.71-1.57 (m, 2H). MS (ESI) m/z 448.5 ([M+H]+)

Example 18

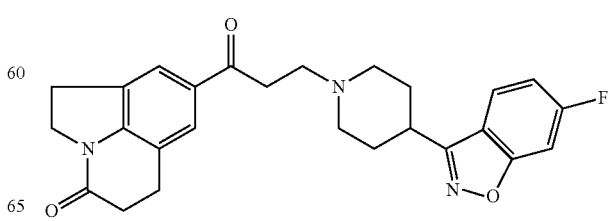

The target compound was prepared according to the method of Example 1, using indoline instead of 1,2,3,4-tetrahydroquinoline, and 5-chlorovaleryl chloride instead of 2-chloroacetyl chloride.

1H NMR (600 MHz, CDCl3) δ 7.68 (dd, J=8.7, 5.1 Hz, 1H), 7.66 (s, 1H), 7.64 (s, 1H), 7.16 (dd, J=8.5, 2.0 Hz, 1H), 7.02-6.96 (m, 1H), 3.87-3.80 (m, 5H), 3.16-3.07 (m, 3H), 2.88 (dd, J=17.1, 9.1 Hz, 3H), 2.79 (t, J=5.2 Hz, 2H), 2.62 (dd, J=13.5, 6.3 Hz, 3H), 2.44-2.37 (m, 2H), 2.20-2.10 (m, 2H), 2.04 (d, J=11.5 Hz, 2H), 1.91 (dd, J=11.9, 5.9 Hz, 3H). MS (ESI) m/z 476.9 ([M+H]$^+$)

Example 19

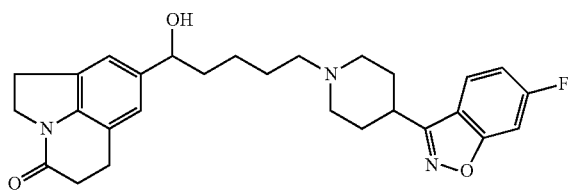 [SMILES: O=C1CCc2cc(C(O)CCCCN3CCC(c4noc5cc(F)ccc45)CC3)cc3c2N1CC3]

The target compound was prepared according to the method of Example 3, using the target compound of Example 18 instead of the target compound of Example 2.

1H NMR (600 MHz, CDCl3) δ 7.79-7.74 (m, 1H), 7.26 (dd, J=8.5, 2.0 Hz, 1H), 7.12 (s, 1H), 7.06 (td, J=8.8, 2.1 Hz, 1H), 7.03 (s, 1H), 4.66 (dd, J=7.9, 5.4 Hz, 1H), 4.11 (t, J=8.4 Hz, 3H), 3.26-3.18 (m, 2H), 3.16-3.06 (m, 2H), 3.04-2.94 (m, 2H), 2.70 (t, J=7.8 Hz, 2H), 2.47-2.39 (m, 2H), 2.28-1.97 (m, 6H), 1.90-1.72 (m, 3H), 1.57-1.49 (m, 3H), 1.46-1.38 (m, 2H). MS (ESI) m/z 478.6 ([M+H]+)

Example 20

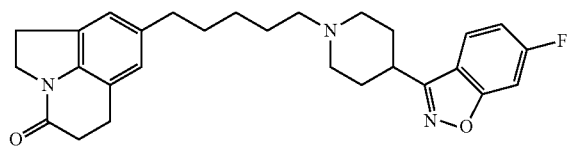 [SMILES: O=C1CCc2cc(CCCCCN3CCC(c4noc5cc(F)ccc45)CC3)cc3c2N1CC3]

The target compound was prepared according to the method of Example 4, using the target compound of Example 18 instead of the target compound of Example 2.

1H NMR (600 MHz, CDCl3) δ 7.74 (dd, J=8.6, 5.1 Hz, 1H), 7.26 (dd, J=8.4, 2.0 Hz, 1H), 7.15-7.00 (m, 1H), 6.92 (s, 1H), 6.83 (s, 1H), 4.09 (t, J=8.4 Hz, 2H), 3.29-3.09 (m, 5H), 2.96 (t, J=7.8 Hz, 2H), 2.69 (t, J=7.7 Hz, 2H), 2.64-2.54 (m, 2H), 2.49 (s, 2H), 2.19 (dd, J=43.3, 32.1 Hz, 6H), 1.64 (dt, J=15.2, 7.7 Hz, 4H), 1.39 (dt, J=15.3, 7.7 Hz, 2H). MS (ESI) m/z 462.9 ([M+H]$^+$)

Example 21

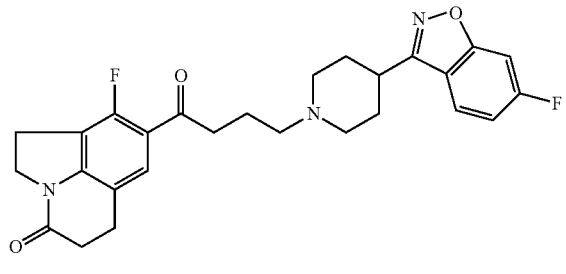 [SMILES: O=C(CCCN1CCC(c2noc3cc(F)ccc23)CC1)c1cc2c3c(c1F)CCN3C(=O)CC2]

The target compound was prepared according to the method of Example 1, using 4-fluoroindoline instead of 1,2,3,4-tetrahydroquinoline, and 4-chlorobutyryl chloride instead of 2-chloroacetyl chloride.

1H NMR (600 MHz, CDCl3) δ 7.72 (s, 1H), 7.62 (dt, J=9.3, 4.7 Hz, 1H), 7.17 (dt, J=8.3, 4.1 Hz, 1H), 7.00 (ddd, J=8.6, 6.4, 1.8 Hz, 1H), 4.08 (t, J=8.2 Hz, 2H), 3.19 (t, J=8.0 Hz, 2H), 3.05-2.90 (m, 7H), 2.67 (t, J=7.5 Hz, 2H), 2.44 (t, J=6.5 Hz, 2H), 2.12 (t, J=10.3 Hz, 2H), 2.04-1.89 (m, 6H). MS (ESI) m/z 480.2 ([M+H]$^+$)

Example 22

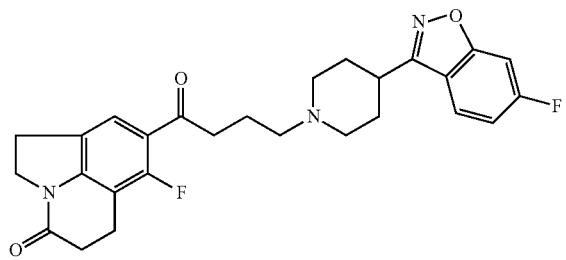 [SMILES: O=C(CCCN1CCC(c2noc3cc(F)ccc23)CC1)c1cc2c3c(c1F)CCC(=O)N3CC2]

The target compound was prepared according to the method of Example 1, using 6-fluoroindoline instead of 1,2,3,4-tetrahydroquinoline, and 4-chlorobutyryl chloride instead of 2-chloroacetyl chloride.

1H NMR (600 MHz, CDCl3) δ 7.65 (s, 1H), 7.62 (dt, J=9.3, 4.7 Hz, 1H), 7.17 (dt, J=8.3, 4.1 Hz, 1H), 7.00 (ddd, J=8.6, 6.4, 1.8 Hz, 1H), 4.08 (t, J=8.2 Hz, 2H), 3.19 (t, J=8.0 Hz, 2H), 3.05-2.90 (m, 7H), 2.67 (t, J=7.5 Hz, 2H), 2.44 (t, J=6.5 Hz, 2H), 2.12 (t, J=10.3 Hz, 2H), 2.04-1.89 (m, 6H). MS (ESI) m/z 480.2 ([M+H]$^+$)

Example 23

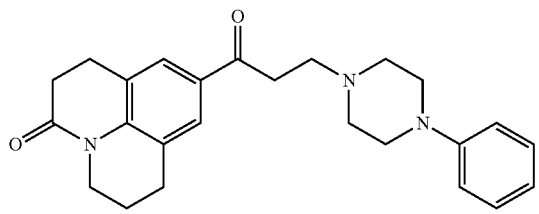 [SMILES: O=C(CCN1CCN(c2ccccn2)CC1)c1cc2c3c(c1)CCC(=O)N3CCC2]

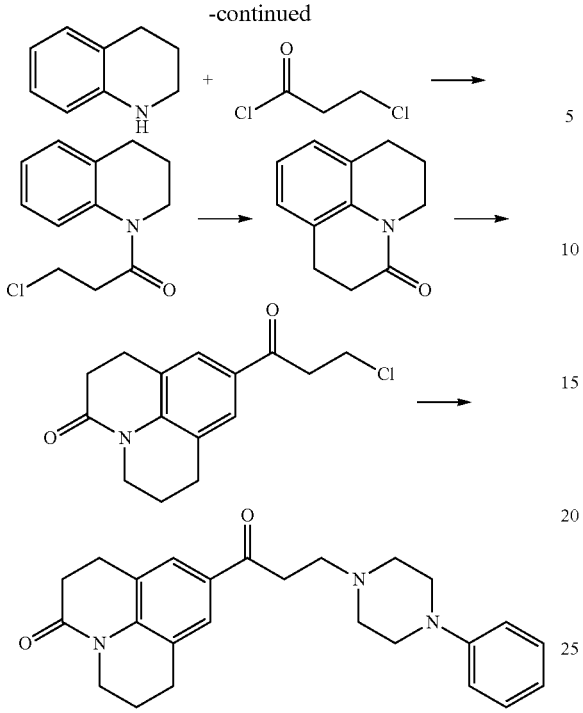

1) To 1,2,3,4-tetrahydroquinoline (5.0 g) was added acetone (50 ml), and then 3-chloropropionyl chloride (5.1 g) was added slowly. The mixture was heated to reflux with stirring. The reaction was completed after 4 hours. The reaction mixture was cooled to room temperature, and the reaction solution was concentrated. The residue was dissolved in ethyl acetate, washed with water, dried with anhydrous magnesium sulfate, filtered off with suction and concentrated to give 8.0 g of oil. Yield: 96.4%.

2) To the product (8 g) from the first step was added anhydrous aluminium trichloride (7.2 g). The mixture was heated with stirring and reacted for 3 hours. After cooling to room temperature, ice water was added to quench the system. The reaction mixture was filtered, extracted with ethyl acetate, washed with water, dried with anhydrous magnesium sulfate, filtered off with suction and concentrated to give 6.05 g of solid. Yield: 90.3%.

3) To the product (5.0 g) from the second step was added 3-chloropropionyl chloride (2.50 mL) and 1,2-dichloroethane (25 mL). The reaction mixture was cooled in ice water bath to about 0° C., anhydrous aluminium trichloride (7.2 g) was added in portions subsequently with the inner temperature kept at about 0° C. The temperature was kept for another 30 min after addition, and then the ice water bath was removed and the mixture was reacted at room temperature for 2 hours. Ice water was added to quench the system. The mixture was filtered, extracted with ethyl acetate, washed with water, dried with anhydrous magnesium sulfate, filtered off with suction and concentrated. Column chromatography (PE:EA=6:1) was performed to give 5.95 g of solid. Yield: 80.0%.

4) To the product from the third step (0.83 g) was added 1-phenylpiperazine (0.48 g), anhydrous potassium carbonate (1 g), potassium iodide (0.2 g) and acetonitrile (25 ml). The reaction mixture was heated under reflux for 12 hours. After cooling to room temperature, the solvent was evaporated to dryness and an appropriate amount of dichloromethane was added. Water washing was performed, and then the water layer was separated and discarded. The organic layer was dried with anhydrous magnesium sulfate. The solvent was evaporated to dryness to give light yellow oil. Column chromatography was performed to give 0.96 g of colorless oil.

1H NMR (600 MHz, CDCl3) δ 7.67 (s, 1H), 7.66 (s, 1H), 7.33-7.26 (m, 2H), 6.96 (d, J=7.9 Hz, 2H), 6.88 (t, J=7.3 Hz, 1H), 3.95-3.88 (m, 2H), 3.26-3.22 (m, 4H), 3.20 (dd, J=9.4, 5.4 Hz, 2H), 2.99-2.95 (m, 2H), 2.92 (t, J=7.4 Hz, 2H), 2.87 (t, J=6.2 Hz, 2H), 2.76-2.64 (m, 6H), 1.99 (dt, J=12.2, 6.1 Hz, 2H). MS (ESI) m/z 404.7 ([M+H]+)

Example 24

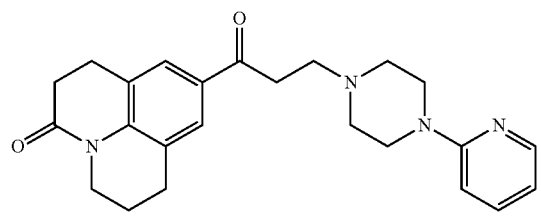

The target compound was prepared according to the method of Example 23, using 1-(pyridin-2-yl)piperazine instead of 1-phenylpiperazine.

1H NMR (600 MHz, CDCl3) δ 8.23 (d, J=4.0 Hz, 1H), 7.73 (s, 1H), 7.71 (s, 1H), 7.58 (t, J=7.8 Hz, 1H), 6.79 (dd, J=6.8, 5.2 Hz, 1H), 6.71 (d, J=8.5 Hz, 1H), 4.26-3.99 (m, 4H), 3.95-3.84 (m, 4H), 3.57 (t, J=6.4 Hz, 2H), 3.46-3.26 (m, 4H), 3.05-2.94 (m, 2H), 2.87 (t, J=6.0 Hz, 2H), 2.75-2.65 (m, 2H), 2.03-1.93 (m, 2H). MS (ESI) m/z 405.6 ([M+H]+)

Example 25

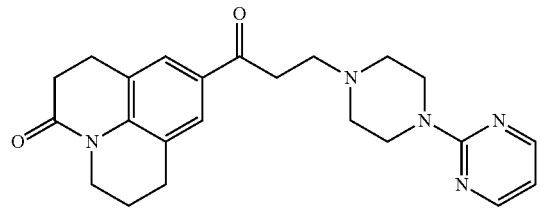

The target compound was prepared according to the method of Example 23, using 1-(pyrimidin-2-yl)piperazine instead of 1-phenylpiperazine.

1H NMR (600 MHz, CDCl3) δ 8.32 (d, J=4.7 Hz, 2H), 7.66 (s, 1H), 7.65 (s, 1H), 6.51 (t, J=4.7 Hz, 1H), 4.08-3.78 (m, 6H), 3.23 (t, J=7.3 Hz, 2H), 2.97-2.92 (m, 4H), 2.86 (t, J=6.2 Hz, 2H), 2.73-2.67 (m, 2H), 2.66-2.62 (m, 4H), 2.00-1.96 (m, 2H). MS (ESI) m/z 406.4 ([M+H]+)

Example 26

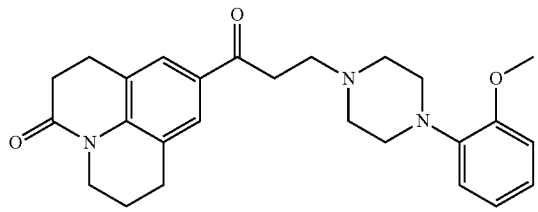 [SMILES: COc1ccccc1N1CCN(CCC(=O)c2cc3c4c(c2)CCC(=O)N4CCC3)CC1]

The target compound was prepared according to the method of Example 23, using 1-(2-methoxyl phenyl)piperazine instead of 1-phenylpiperazine.

1H NMR (600 MHz, CDCl3) δ 7.67 (s, 1H), 7.66 (s, 1H), 7.33-7.26 (m, 2H), 6.96 (d, J=7.9 Hz, 2H), 6.88 (t, J=7.3 Hz, 1H), 3.95-3.88 (m, 2H), 3.26-3.22 (m, 4H), 3.20 (dd, J=9.4, 5.4 Hz, 2H), 2.99-2.95 (m, 2H), 2.92 (t, J=7.4 Hz, 2H), 2.87 (t, J=6.2 Hz, 2H), 2.76-2.64 (m, 6H), 1.99 (dt, J=12.2, 6.1 Hz, 2H). MS (ESI) m/z 434.5 ([M+H]$^+$)

Example 27

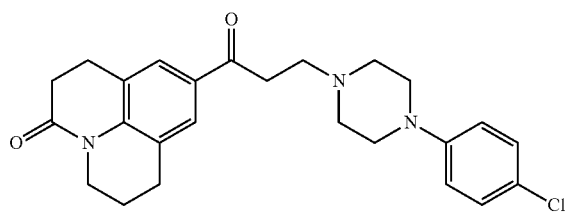 [SMILES: O=C(CCN1CCN(c2ccc(Cl)cc2)CC1)c1cc2c3c(c1)CCC(=O)N3CCC2]

The target compound was prepared according to the method of Example 23, using 1-(4-chlorophenyl)piperazine instead of 1-phenylpiperazine.

1H NMR (600 MHz, CDCl3) δ 7.66 (s, 1H), 7.65 (s, 1H), 7.21 (d, J=9.0 Hz, 2H), 6.91-6.81 (d, J=9.0 Hz, 2H), 3.95-3.85 (m, 2H), 3.19 (dd, J=8.9, 4.2 Hz, 6H), 2.98-2.94 (m, 2H), 2.92 (t, J=7.4 Hz, 2H), 2.86 (t, J=6.2 Hz, 2H), 2.75-2.66 (m, 6H), 1.98 (m, 2H). MS (ESI) m/z 438.9 [M+H]$^+$)

Example 28

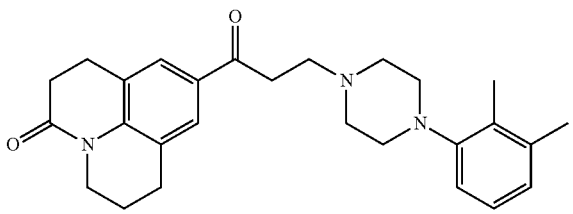 [SMILES: Cc1cccc(N2CCN(CCC(=O)c3cc4c5c(c3)CCC(=O)N5CCC4)CC2)c1C]

The target compound was prepared according to the method of Example 23, using 1-(2,3-dimethylphenyl)piperazine hydrochloride instead of 1-phenylpiperazine.

1H NMR (600 MHz, CDCl3) δ 7.68 (s, 1H), 7.67 (s, 1H), 7.10 (t, J=7.7 Hz, 1H), 6.97-6.91 (m, 2H), 3.95-3.89 (m, 2H), 3.23 (t, J=7.4 Hz, 2H), 3.02-2.91 (m, 8H), 2.87 (t, J=6.2 Hz, 2H), 2.80-2.67 (m, 5H), 2.29 (s, 3H), 2.24 (s, 3H), 1.99 (dt, J=12.1, 6.1 Hz, 3H). MS (ESI) m/z 432.4 ([M+H]$^+$)

Example 29

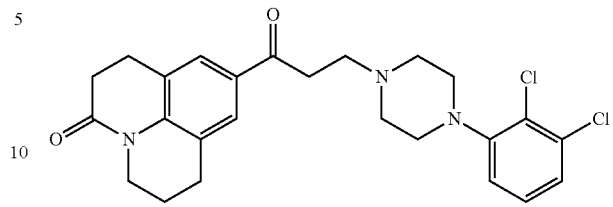

The target compound was prepared according to the method of Example 23, using 1-(2,3-dichlorophenyl)piperazine hydrochloride instead of 1-phenylpiperazine.

1H NMR (600 MHz, CDCl3) δ 7.67 (s, 1H), 7.65 (s, 1H), 7.21-7.10 (m, 2H), 6.98 (dd, J=7.3, 2.3 Hz, 1H), 4.01-3.83 (m, 2H), 3.20 (t, J=7.4 Hz, 2H), 3.11 (s, 4H), 2.96 (dt, J=10.5, 7.2 Hz, 4H), 2.87 (t, J=6.2 Hz, 2H), 2.79-2.66 (m, 6H), 1.99 (dt, J=12.2, 6.1 Hz, 2H). MS (ESI) m/z 472.6 ([M+H]$^+$)

Example 30

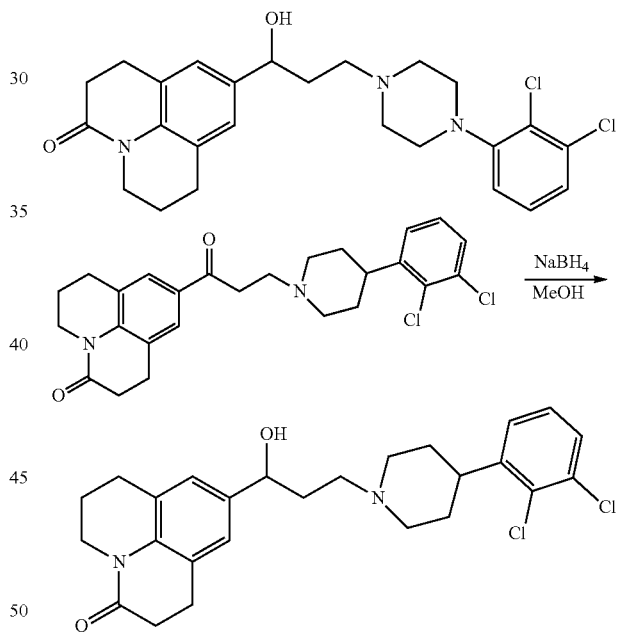

The target compound of Example 29 (0.5 g) was dissolved in anhydrous methanol (20 mL). The reaction mixture was cooled to 0° C. in ice water bath, sodium borohydride (0.08 g) was added to the mixture, and the reaction was continued with stirring for another 1 h. The reaction was quenched by adding 10 mL of water. The solvent was evaporated to dryness and an appropriate amount of dichloromethane was added. Water washing was performed, and then the water layer was separated and discarded. The organic layer was dried with anhydrous magnesium sulfate. The solvent was evaporated to dryness to give light yellow oil. Column chromatography was performed to give 0.40 g of white solid.

1H NMR (600 MHz, CDCl3) δ 7.29 (s, 1H), 7.21-7.15 (m, 1H), 7.04 (s, 2H), 6.97 (dd, J=7.4, 2.1 Hz, 1H), 4.89 (dd,

J=9.0, 2.5 Hz, 1H), 3.88 (td, J=5.0, 2.0 Hz, 3H), 3.14 (s, 4H), 2.96-2.55 (m, 12H), 1.98-1.79 (n, 4H). MS (ESI) m/z 474.6 ([M+H]⁺)

Example 31

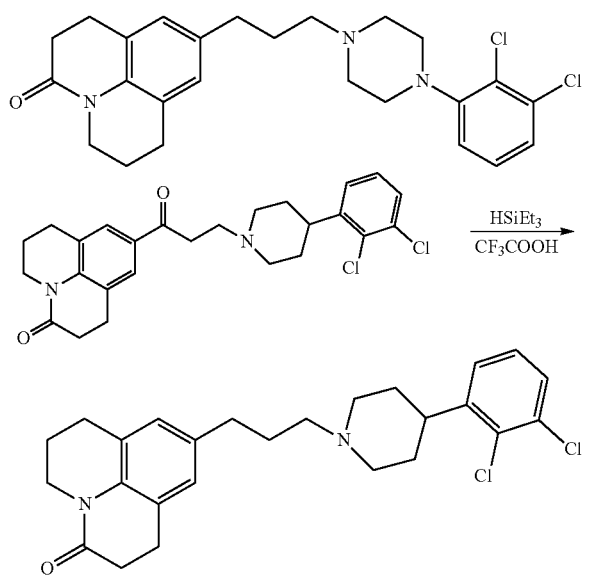

The target compound of Example 29 (0.5 g) was dissolved in trifluoroacetic acid (20 mL), and then triethylsilane (0.10 g) was added slowly. The mixture was stirred overnight at room temperature. The solvent was evaporated to dryness and an appropriate amount of dichloromethane was added. Washing with saturated NaHCO₃ solution was performed. The water layer was separated and discarded. The organic layer was dried with anhydrous magnesium sulfate. The solvent was evaporated to dryness to give light yellow oil. Column chromatography was performed to give 0.35 g of colorless transparent oil.

1H NMR (600 MHz, CDCl3) δ 7.65 (s, 1H), 7.63 (s, 1H), 7.18-7.11 (m, 2H), 6.98-6.93 (m, 1H), 3.93-3.87 (m, 2H), 3.26-3.17 (m, 2H), 3.10 (s, 2H), 2.99-2.91 (m, 4H), 2.83 (dd, J=16.6, 10.0 Hz, 4H), 2.76 (dd, J=13.5, 7.0 Hz, 4H), 2.67 (dd, J=15.4, 8.1 Hz, 2H), 1.99-1.86 (m, 4H). MS (ESI) m/z 458.8 ([M+H]⁺)

Example 32

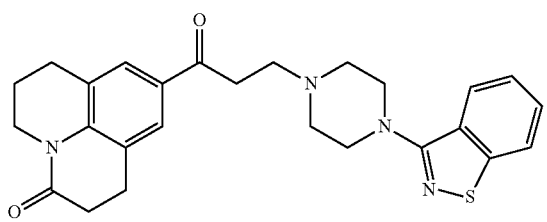 [SMILES: O=C(CCN1CCN(c2nsc3ccccc23)CC1)c1cc2c3c(c1)CCC(=O)N3CCC2]

The target compound was prepared according to the method of Example 23, using 1-(4-(benzo[d]isothiazol-3-yl) piperazine instead of 1-phenylpiperazine.

1H NMR (600 MHz, CDCl3) δ 7.91 (d, J=8.2 Hz, 1H), 7.81 (d, J=8.1 Hz, 1H), 7.66 (d, J=9.5 Hz, 2H), 7.49-7.45 (m, 1H), 7.38-7.32 (m, 1H), 3.93-3.87 (m, 2H), 3.63-3.53 (m, 4H), 3.21 (t, J=7.4 Hz, 2H), 2.95 (q, J=7.1 Hz, 4H), 2.85 (t, J=6.2 Hz, 2H), 2.79-2.75 (m, 4H), 2.72-2.65 (m, 2H), 1.97 (dt, J=12.2, 6.1 Hz, 2H). MS (ESI) m/z 461.5 ([M+H]⁺)

Example 33

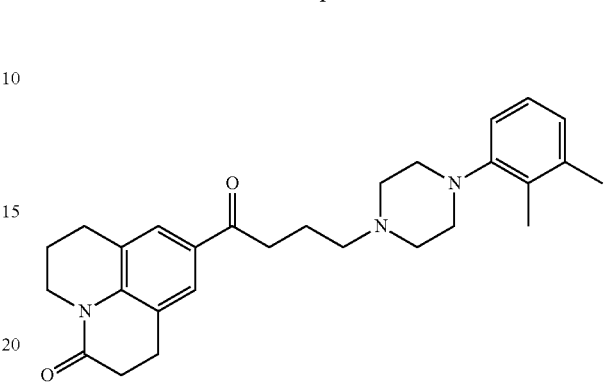

The target compound was prepared according to the method of Example 23, using 4-chlorobutyryl chloride instead of 3-chloropropionyl chloride, and 1-(2,3-dimethylphenyl)piperazine hydrochloride instead of 1-phenylpiperazine.

1H NMR (600 MHz, CDCl3) δ 7.68 (s, 1H), 7.67 (s, 1H), 7.09 (t, J=7.7 Hz, 1H), 6.92 (d, J=7.7 Hz, 2H), 3.95-3.88 (m, 2H), 3.01 (t, J=7.2 Hz, 2H), 2.98-2.95 (m, 2H), 2.91 (s, 2H), 2.87 (t, J=6.2 Hz, 2H), 2.69 (dd, J=17.7, 10.5 Hz, 4H), 2.53 (t, J=7.2 Hz, 2H), 2.28 (s, 3H), 2.23 (s, 3H), 2.06-1.95 (m, 6H). MS (ESI) m/z 446.7 ([M+H]⁺)

Example 34

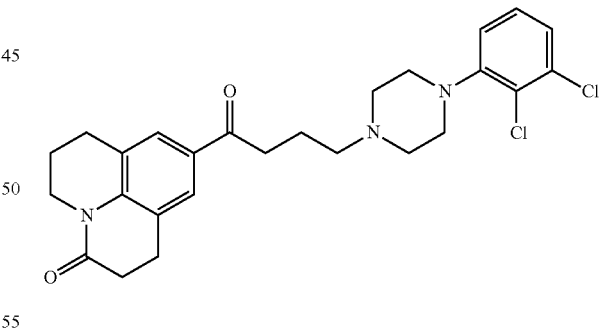

The target compound was prepared according to the method of Example 33, using 1-(2,3-dichlorophenyl)piperazine hydrochloride instead of 1-(2,3-dimethylphenyl)piperazine hydrochloride.

1H NMR (600 MHz, CDCl3) δ 7.67 (s, 1H), 7.65 (s, 1H), 7.20-7.13 (m, 2H), 6.95 (dd, J=7.1, 2.4 Hz, 1H), 3.95-3.88 (m, 2H), 3.03 (d, J=27.0 Hz, 4H), 3.00 (t, J=7.2 Hz, 2H), 2.98-2.94 (m, 2H), 2.86 (t, J=6.2 Hz, 2H), 2.69 (dd, J=15.4, 8.2 Hz, 6H), 2.52 (t, J=7.2 Hz, 2H), 2.07-1.89 (m, 4H). MS (ESI) m/z 486.5 ([M+H]⁺)

Example 35

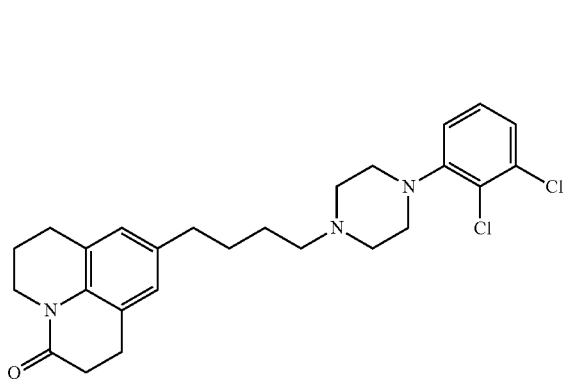 [SMILES: O=C1CCc2cc(CCCCN3CCN(c4cccc(Cl)c4Cl)CC3)cc3c2N1CCC3]

The target compound was prepared according to the method of Example 31, using the target compound of example 34 instead of the target compound of Example 29.

1H NMR (600 MHz, CDCl3) δ 7.21-7.12 (m, 2H), 7.02-6.95 (m, 1H), 6.84 (d, J=2.3 Hz, 2H), 3.93-3.83 (m, 2H), 3.18-3.07 (m, 4H), 2.92-2.85 (m, 2H), 2.78 (t, J=6.2 Hz, 2H), 2.66 (dd, J=8.4, 6.5 Hz, 6H), 2.58 (t, J=7.4 Hz, 2H), 2.50-2.45 (m, 2H), 1.97-1.93 (m, 2H), 1.69-1.56 (m, 4H). MS (ESI) m/z 472.4 ([M+H]+)

Example 36

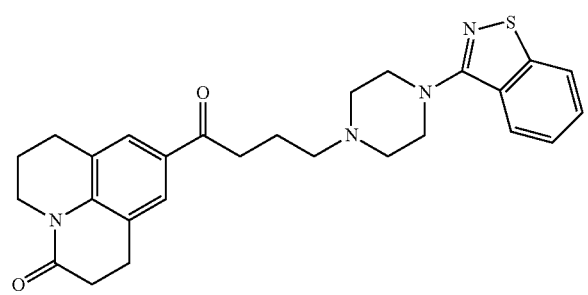 [SMILES: O=C(CCCN1CCN(c2nsc3ccccc23)CC1)c1cc2c3c(c1)CCC(=O)N3CCC2]

The target compound was prepared according to the method of Example 33, using 1-(4-(benzo[d]isothiazol-3-yl)piperazine hydrochloride instead of 1-(2,3-dimethylphenyl)piperazine hydrochloride.

1H NMR (600 MHz, CDCl3) δ 7.92 (d, J=8.2 Hz, 1H), 7.83 (d, J=8.1 Hz, 1H), 7.67 (s, 1H), 7.66 (s, 1H), 7.51-7.46 (m, 1H), 7.41-7.34 (m, 1H), 3.95-3.87 (m, 2H), 3.56 (d, J=4.0 Hz, 4H), 3.02 (t, J=7.1 Hz, 2H), 2.98-2.94 (m, 2H), 2.86 (t, J=6.2 Hz, 2H), 2.75-2.68 (m, 6H), 2.55 (t, J=7.1 Hz, 2H), 2.08-1.95 (m, 4H). MS (ESI) m/z 475.4 ([M+H]+)

Example 37

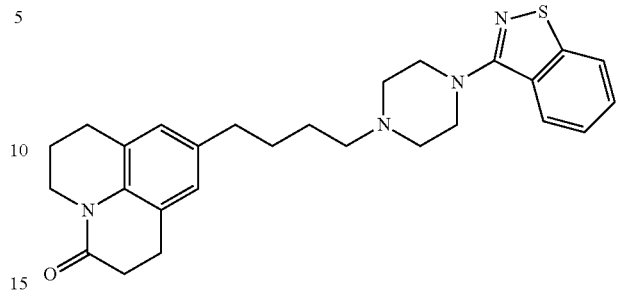

The target compound was prepared according to the method of Example 31, using the target compound of Example 36 instead of the target compound of Example 29.

1H NMR (600 MHz, CDCl3) δ 7.93 (d, J=8.2 Hz, 1H), 7.83 (d, J=8.1 Hz, 1H), 7.53-7.45 (m, 1H), 7.41-7.34 (m, 1H), 6.85 (d, J=2.6 Hz, 2H), 3.94-3.82 (m, 2H), 3.69-3.54 (m, 4H), 2.91-2.83 (m, 2H), 2.79 (t, J=6.2 Hz, 2H), 2.73-2.68 (m, 4H), 2.66 (dd, J=8.4, 6.5 Hz, 2H), 2.59 (t, J=7.5 Hz, 2H), 2.51-2.46 (m, 2H), 1.95 (dt, J=12.2, 6.1 Hz, 2H), 1.71-1.57 (m, 4H). MS (ESI) m/z 461.5 ([M+H]+)

Example 38

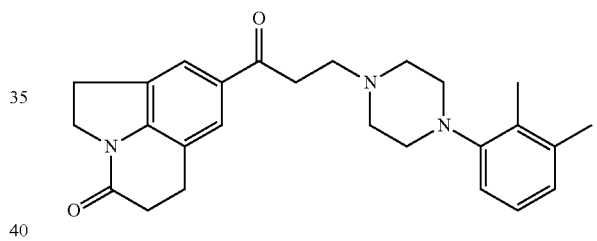

The target compound was prepared according to the method of Example 23, using indoline instead of 1,2,3,4-tetrahydroquinoline, and 1-(2,3-dimethylphenyl)piperazine instead of 1-phenylpiperazine.

1H NMR (600 MHz, CDCl3) δ 7.09 (t, J=7.7 Hz, 1H), 6.93 (dd, J=10.1, 8.1 Hz, 2H), 4.15 (t, J=8.5 Hz, 2H), 3.25 (t, J=8.5 Hz, 2H), 3.21 (t, J=7.4 Hz, 2H), 3.05 (t, J=7.8 Hz, 2H), 3.00-2.90 (m, 6H), 2.74 (t, J=7.8 Hz, 4H), 2.28 (s, 3H), 2.24 (s, 3H). MS (ESI) m/z 418.8 ([M+H]+)

Example 39

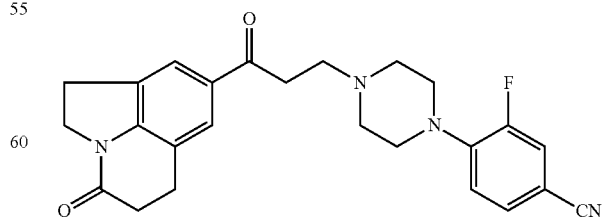

The target compound was prepared according to the method of Example 38, using 3-fluoro-4-(piperazin-1-yl)benzonitrile instead of 1-(2,3-dimethylphenyl)piperazine.

1H NMR (600 MHz, CDCl3) δ 7.75 (s, 1H), 7.71 (s, 1H), 7.39-7.35 (m, J=8.4, 1.4 Hz, 1H), 7.32-7.25 (m, 1H), 6.93 (t, J=8.5 Hz, 1H), 4.15 (t, J=8.4 Hz, 2H), 3.25 (dd, J=9.3, 5.5 Hz, 6H), 3.17 (t, J=7.3 Hz, 2H), 3.04 (t, J=7.8 Hz, 2H), 2.92 (t, J=7.3 Hz, 2H), 2.74 (t, J=7.8 Hz, 2H), 2.72-2.70 (m, 4H). MS (ESI) m/z 433.6 ([M+H]+)

Example 40

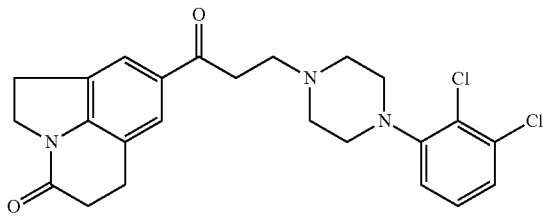 [SMILES: O=C(CCN1CCN(c2cccc(Cl)c2Cl)CC1)c1cc2c3c(c1)CCN3C(=O)CC2]

The target compound was prepared according to the method of Example 38, using 1-(2,3-dichlorophenyl)piperazine instead of 1-(2,3-dimethylphenyl)piperazine.

1H NMR (600 MHz, CDCl3) δ 7.76 (s, 1H), 7.71 (s, 1H), 7.21-7.14 (m, 2H), 7.02-6.95 (m, 1H), 4.15 (t, J=8.5 Hz, 2H), 3.27-3.20 (m, 4H), 3.12 (s, 2H), 3.04 (t, J=7.8 Hz, 2H), 2.99 (t, J=7.3 Hz, 2H), 2.77 (d, J=21.4 Hz, 4H), 2.74 (t, J=7.8 Hz, 4H). MS (ESI) m/z 458.4 ([M+H]+)

Example 41

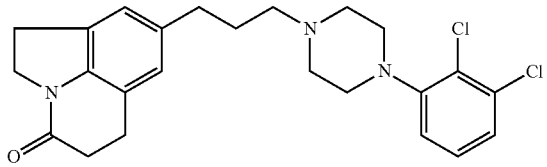 [SMILES: O=C1CCc2cc(CCCN3CCN(c4cccc(Cl)c4Cl)CC3)cc3c2N1CC3]

The target compound was prepared according to the method of Example 31, using the target compound of Example 40 instead of the target compound of Example 29.

1H NMR (600 MHz, CDCl3) δ 7.76 (s, 1H), 7.71 (s, 1H), 7.21-7.14 (m, 2H), 7.02-6.95 (m, 1H), 4.15 (t, J=8.5 Hz, 2H), 3.27-3.20 (m, 4H), 3.12 (s, 4H), 3.04 (t, J=7.8 Hz, 2H), 2.99 (t, J=7.3 Hz, 2H), 2.77 (d, J=21.4 Hz, 4H), 2.74 (t, J=7.8 Hz, 4H). MS (ESI) m/z 444.6 ([M+H]+)

Example 42

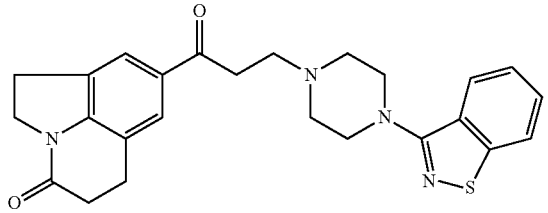 [SMILES: O=C(CCN1CCN(c2nsc3ccccc23)CC1)c1cc2c3c(c1)CCN3C(=O)CC2]

The target compound was prepared according to the method of Example 38, using 1-(benzo[d]isothiazol-3-yl)piperazine instead of 1-(2,3-dimethylphenyl)piperazine.

1H NMR (600 MHz, CDCl3) δ 7.92 (d, J=8.2 Hz, 1H), 7.82 (d, J=8.1 Hz, 1H), 7.77 (s, 1H), 7.72 (s, 1H), 7.48 (t, J=7.5 Hz, 1H), 7.37 (t, J=7.5 Hz, 1H), 4.15 (t, J=8.5 Hz, 2H), 3.63-3.55 (m, 4H), 3.25 (t, J=8.5 Hz, 2H), 3.21 (t, J=7.4 Hz, 2H), 3.04 (t, J=7.8 Hz, 2H), 2.95 (t, J=7.4 Hz, 2H), 2.79-2.76 (m, 4H), 2.74 (t, J=7.8 Hz, 2H). MS (ESI) m/z 447.5 ([M+H]+)

Example 43

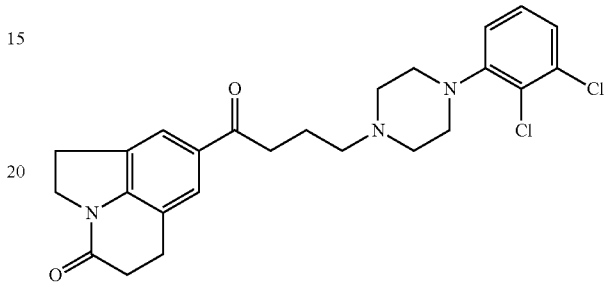

The target compound was prepared according to the method of Example 23, using 4-chlorobutyryl chloride instead of 3-chloropropionyl chloride, and 1-(2,3-dichlorophenyl)piperazine instead of 1-phenylpiperazine.

1H NMR (600 MHz, CDCl3) δ 7.77 (s, 1H), 7.71 (d, J=12.1 Hz, 1H), 7.22-7.12 (m, 2H), 7.01-6.91 (m, 1H), 4.51 (t, J=8.5 Hz, 2H), 4.15 (t, J=8.5 Hz, 2H), 3.78 (t, J=8.5 Hz, 2H), 3.25 (t, J=8.5 Hz, 2H), 3.13-3.06 (m, 4H), 3.03 (m, 4H), 2.75 (t, J=8.5 Hz, 4H), 2.10-1.95 (m, 2H). MS (ESI) m/z 472.8 ([M+H]+)

Example 44

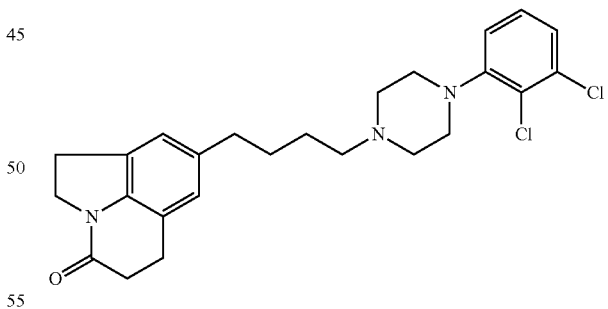

The target compound was prepared according to the method of Example 31, using the target compound of Example 43 instead of the target compound of Example 29.

1H NMR (600 MHz, CDCl3) δ 7.26 (dd, J=8.0, 1.3 Hz, 1H), 7.21 (t, J=8.0 Hz, 1H), 7.03 (dd, J=8.0, 1.3 Hz, 1H), 6.92 (s, 1H), 6.83 (s, 1H), 4.09 (t, J=8.4 Hz, 2H), 3.48 (d, J=36.7 Hz, 4H), 3.27 (s, 2H), 3.18 (t, J=8.4 Hz, 4H), 2.97 (dd, J=15.4, 7.7 Hz, 4H), 2.69 (t, J=7.8 Hz, 2H), 2.64 (t, J=7.5 Hz, 2H), 2.00-1.93 (m, 2H), 1.74-1.65 (m, 2H).

MS (ESI) m/z 458.8 ([M+H]+)

Example 45

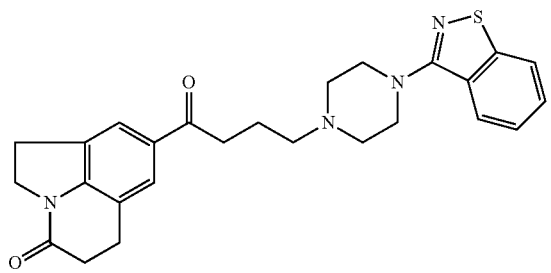 [SMILES: O=C(CCCN1CCN(c2nsc3ccccc23)CC1)c1cc2c3c(c1)CCN3C(=O)CC2]

The target compound was prepared according to the method of Example 23, using 4-chlorobutyryl chloride instead of 3-chloropropionyl chloride, indoline instead of 1,2,3,4-tetrahydroquinoline, and 1-(benzo[d]isothiazol-3-yl)piperazine instead of 1-phenylpiperazine.

1H NMR (600 MHz, CDCl3) δ 7.87 (d, J=8.2 Hz, 1H), 7.84 (d, J=8.1 Hz, 1H), 7.75 (s, 1H), 7.71 (s, 1H), 7.51 (t, J=7.4 Hz, 1H), 7.39 (t, J=7.5 Hz, 1H), 4.14 (td, J=8.5, 3.8 Hz, 2H), 3.89 (d, J=12.5 Hz, 2H), 3.75 (dd, J=10.8, 4.8 Hz, 2H), 3.47 (t, J=6.1 Hz, 2H), 3.23 (dt, J=23.0, 11.6 Hz, 2H), 3.13 (t, J=7.0 Hz, 2H), 3.03 (dd, J=14.7, 7.5 Hz, 4H), 2.73 (td, J=7.8, 3.5 Hz, 2H), 2.23 (dt, J=13.2, 6.7 Hz, 2H), 2.06-1.98 (m, 2H).

MS (ESI) m/z 461.9 ([M+H]$^+$)

Example 46

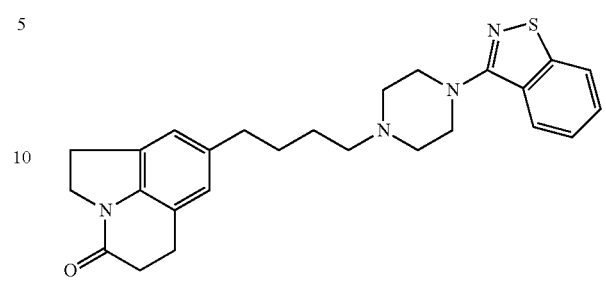

The target compound was prepared according to the method of Example 31, using the target compound of Example 45 instead of the target compound of Example 29.

1H NMR (600 MHz, CDCl3) δ 7.94 (t, J=14.2 Hz, 1H), 7.83 (d, J=8.1 Hz, 1H), 7.53-7.45 (m, 1H), 7.38 (t, J=7.6 Hz, 1H), 6.93 (s, 1H), 6.84 (s, 1H), 4.09 (t, J=8.4 Hz, 2H), 3.61 (s, 4H), 3.18 (t, J=8.4 Hz, 2H), 2.96 (t, J=7.7 Hz, 2H), 2.70 (dd, J=14.1, 6.3 Hz, 6H), 2.62 (t, J=7.3 Hz, 2H), 2.54-2.43 (m, 2H), 1.65 (ddd, J=20.7, 10.8, 6.3 Hz, 4H).

MS (ESI) m/z 447.6 ([M+H]$^+$)

TABLE 1

Numbers and structures of the preferable compounds prepared in the Examples

| No. | Structure |
|---|---|
| 1 | 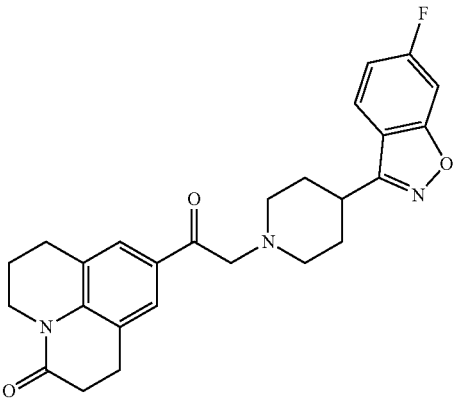 [SMILES: O=C(CN1CCC(c2noc3cc(F)ccc23)CC1)c1cc2c3c(c1)CCC(=O)N3CCC2] |
| 2 | 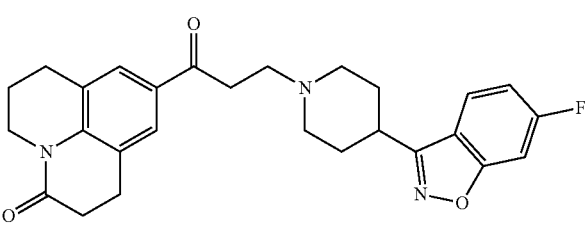 [SMILES: O=C(CCN1CCC(c2noc3cc(F)ccc23)CC1)c1cc2c3c(c1)CCC(=O)N3CCC2] |

TABLE 1-continued
Numbers and structures of the preferable compounds prepared in the Examples
| No. | Structure |
|---|---|
| 3 | 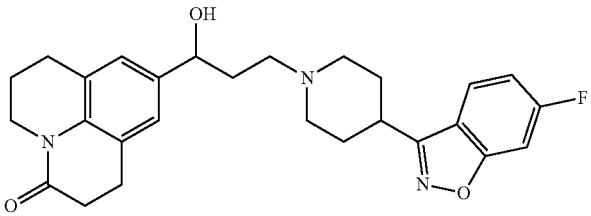 [SMILES: O=C1CCc2cc(C(O)CCN3CCC(c4noc5cc(F)ccc45)CC3)cc3c2N1CCC3] |
| 4 | 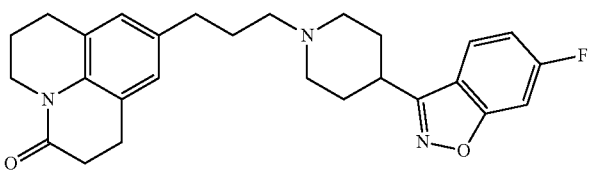 [SMILES: O=C1CCc2cc(CCCN3CCC(c4noc5cc(F)ccc45)CC3)cc3c2N1CCC3] |
| 5 | 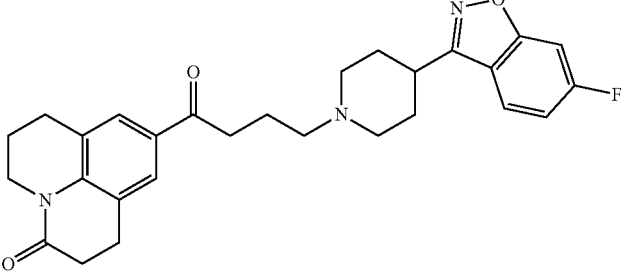 |
| 6 | 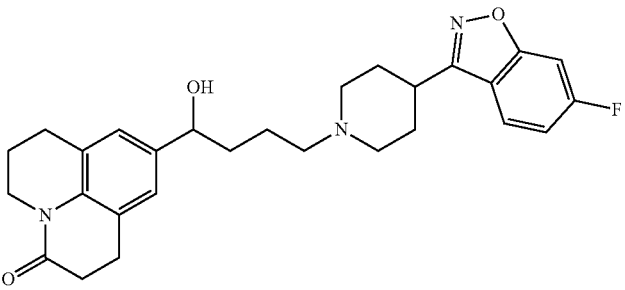 [SMILES: O=C1CCc2cc(C(O)CCCN3CCC(c4noc5cc(F)ccc45)CC3)cc3c2N1CCC3] |
| 7 | 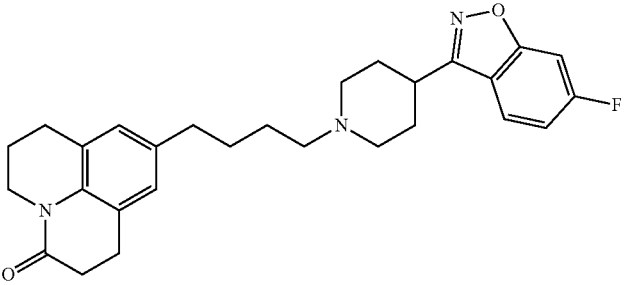 [SMILES: O=C1CCc2cc(CCCCN3CCC(c4noc5cc(F)ccc45)CC3)cc3c2N1CCC3] |
| 8 | 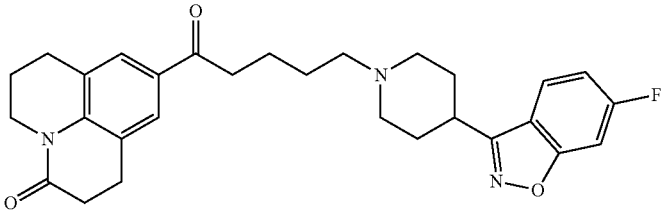 [SMILES: O=C(CCCCN1CCC(c2noc3cc(F)ccc23)CC1)c1cc2c3c(c1)CCC(=O)N3CCC2] |

TABLE 1-continued
Numbers and structures of the preferable compounds prepared in the Examples
| No. | Structure |
|---|---|
| 9 | 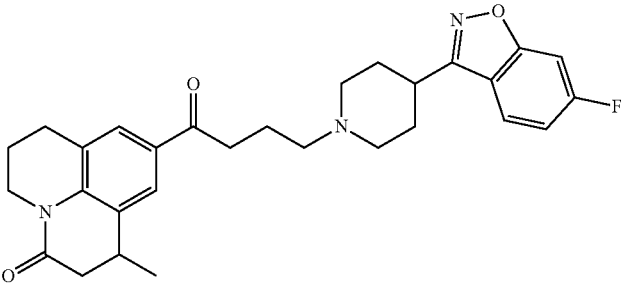 [SMILES: CC1CC(=O)N2CCCc3cc(C(=O)CCCN4CCC(c5noc6cc(F)ccc56)CC4)cc1c32] |
| 10 | 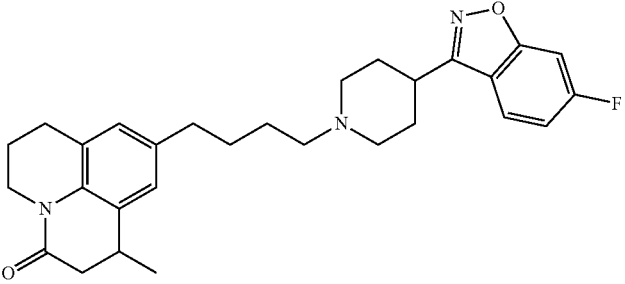 [SMILES: CC1CC(=O)N2CCCc3cc(CCCCN4CCC(c5noc6cc(F)ccc56)CC4)cc1c32] |
| 11 | 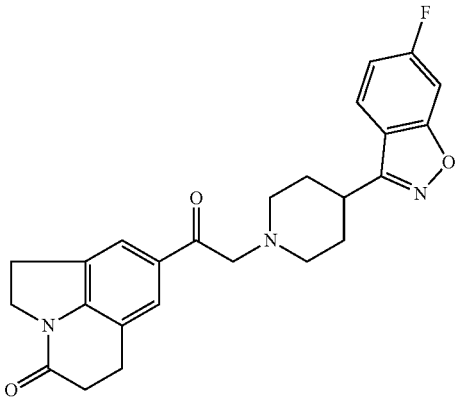 [SMILES: O=C(CN1CCC(c2noc3cc(F)ccc23)CC1)c1cc2c3c(c1)CCN3C(=O)CC2] |
| 12 | 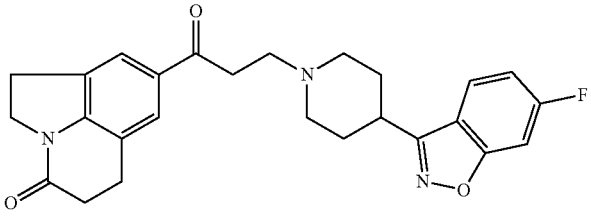 [SMILES: O=C(CCN1CCC(c2noc3cc(F)ccc23)CC1)c1cc2c3c(c1)CCN3C(=O)CC2] |
| 13 | 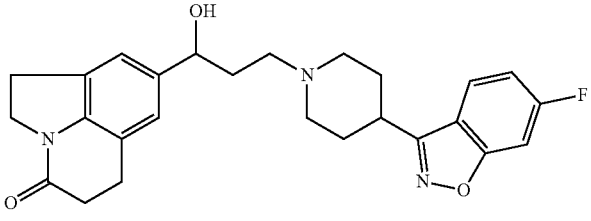 |

TABLE 1-continued
Numbers and structures of the preferable compounds prepared in the Examples
| No. | Structure |
|---|---|
| 14 | 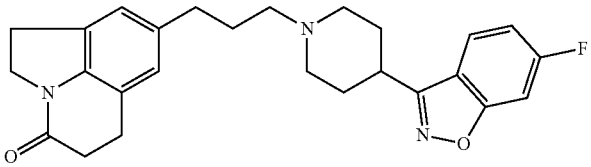 [SMILES: O=C1CCc2cc(CCCN3CCC(c4noc5cc(F)ccc45)CC3)cc3c2N1CC3] |
| 15 | 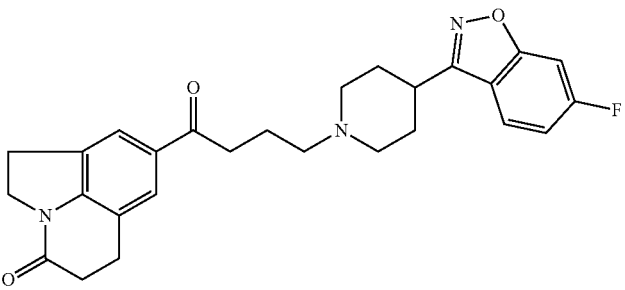 [SMILES: O=C(CCCN1CCC(c2noc3cc(F)ccc23)CC1)c1cc2c3c(c1)CCN3C(=O)CC2] |
| 16 | 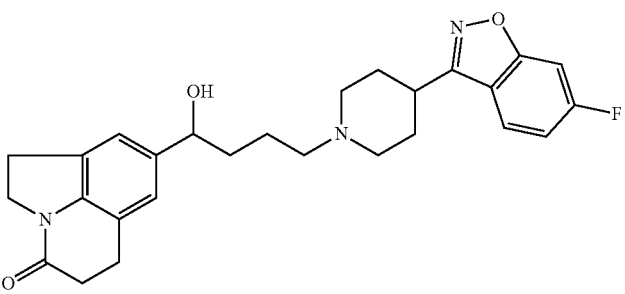 [SMILES: O=C1CCc2cc(C(O)CCCN3CCC(c4noc5cc(F)ccc45)CC3)cc3c2N1CC3] |
| 17 | 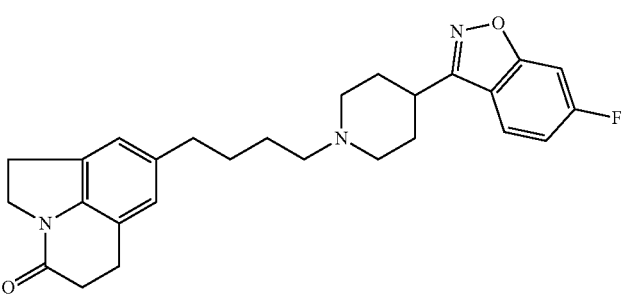 [SMILES: O=C1CCc2cc(CCCCN3CCC(c4noc5cc(F)ccc45)CC3)cc3c2N1CC3] |
| 18 | 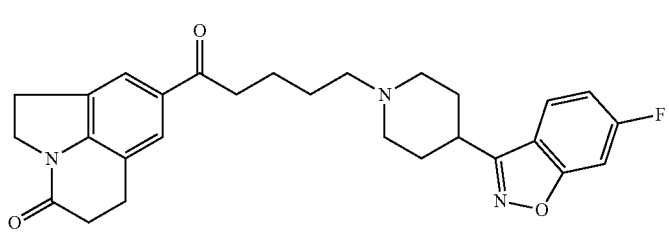 [SMILES: O=C(CCCCN1CCC(c2noc3cc(F)ccc23)CC1)c1cc2c3c(c1)CCN3C(=O)CC2] |
| 19 | 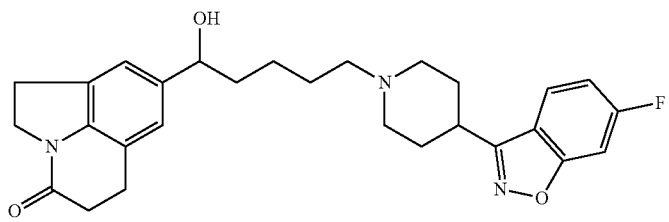 [SMILES: O=C1CCc2cc(C(O)CCCCN3CCC(c4noc5cc(F)ccc45)CC3)cc3c2N1CC3] |

TABLE 1-continued

Numbers and structures of the preferable compounds prepared in the Examples

| No. | Structure |
|---|---|
| 20 | 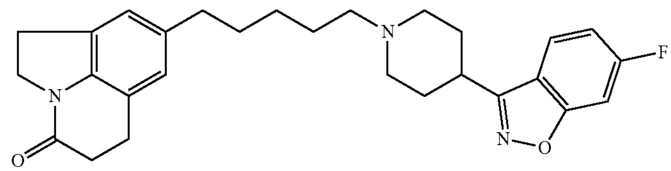 [SMILES: O=C1CCc2cc(CCCCCN3CCC(c4noc5cc(F)ccc45)CC3)cc3c2N1CC3] |
| 21 | 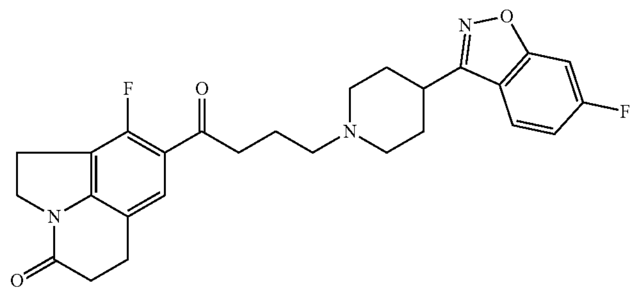 [SMILES: O=C(CCCN1CCC(c2noc3cc(F)ccc23)CC1)c1cc2c3c(c1F)CCN3C(=O)CC2] |
| 22 | 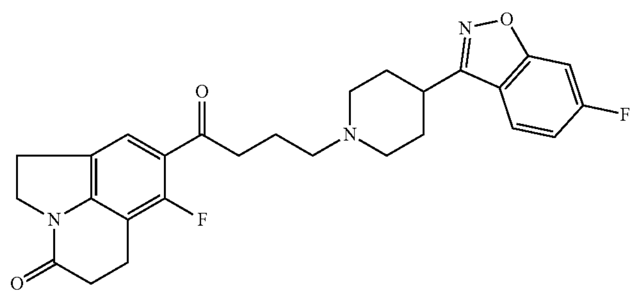 [SMILES: O=C(CCCN1CCC(c2noc3cc(F)ccc23)CC1)c1cc2c3c(c1F)CCC(=O)N3CC2] |
| 23 | 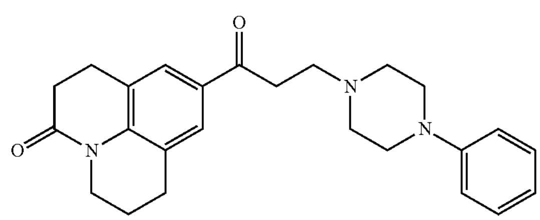 [SMILES: O=C(CCN1CCN(c2ccccc2)CC1)c1cc2c3c(c1)CCC(=O)N3CCC2] |
| 24 | 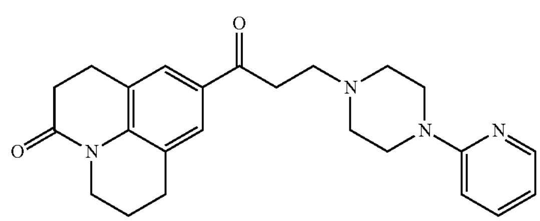 |
| 25 | 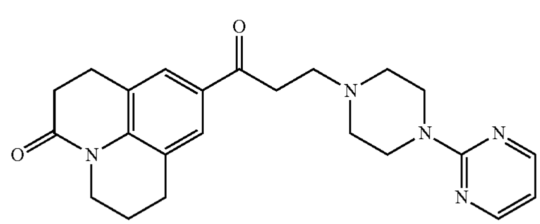 |

TABLE 1-continued

Numbers and structures of the preferable compounds prepared in the Examples

| No. | Structure |
|---|---|
| 26 | 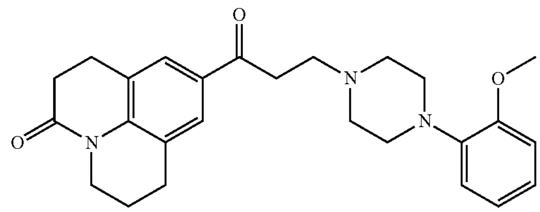 [SMILES: COc1ccccc1N1CCN(CCC(=O)c2cc3c4c(c2)CCC(=O)N4CCC3)CC1] |
| 27 | 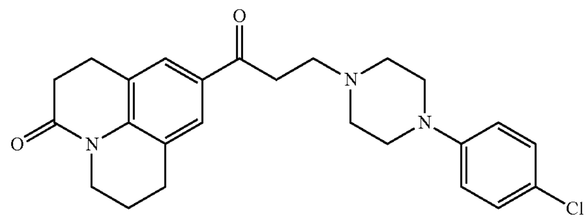 [SMILES: O=C(CCN1CCN(c2ccc(Cl)cc2)CC1)c1cc2c3c(c1)CCC(=O)N3CCC2] |
| 28 | 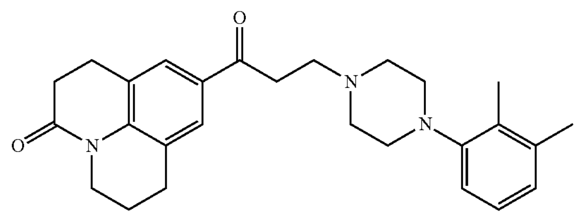 [SMILES: Cc1cccc(N2CCN(CCC(=O)c3cc4c5c(c3)CCC(=O)N5CCC4)CC2)c1C] |
| 29 | 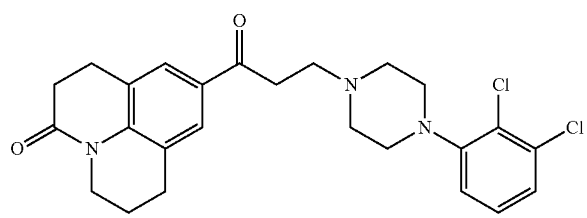 [SMILES: O=C(CCN1CCN(c2cccc(Cl)c2Cl)CC1)c1cc2c3c(c1)CCC(=O)N3CCC2] |
| 30 | 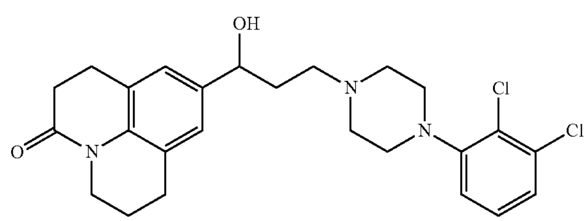 [SMILES: O=C1CCc2cc(C(O)CCN3CCN(c4cccc(Cl)c4Cl)CC3)cc3c2N1CCC3] |
| 31 | 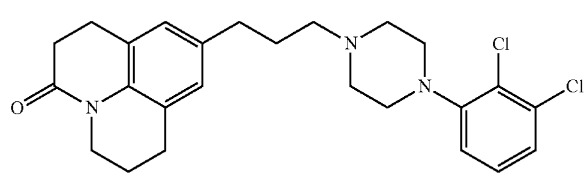 [SMILES: O=C1CCc2cc(CCCN3CCN(c4cccc(Cl)c4Cl)CC3)cc3c2N1CCC3] |
| 32 | 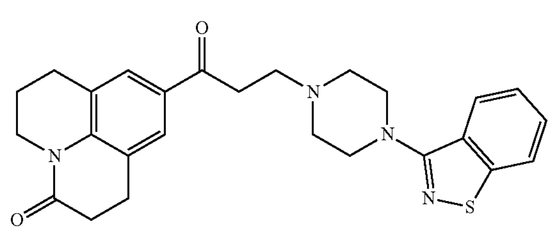 [SMILES: O=C(CCN1CCN(c2nsc3ccccc23)CC1)c1cc2c3c(c1)CCC(=O)N3CCC2] |

TABLE 1-continued

Numbers and structures of the preferable compounds prepared in the Examples

| No. | Structure |
|---|---|
| 33 | 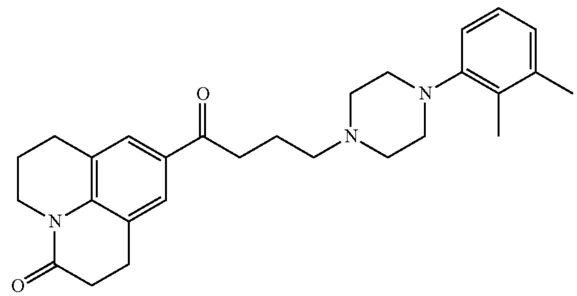 [SMILES: Cc1cccc(N2CCN(CCCC(=O)c3cc4c5c(c3)CCC(=O)N5CCC4)CC2)c1C] |
| 34 | 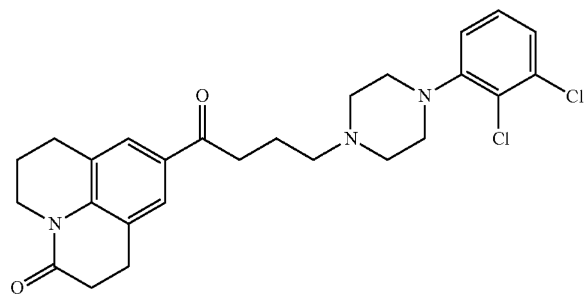 [SMILES: O=C(CCCN1CCN(c2cccc(Cl)c2Cl)CC1)c1cc2c3c(c1)CCC(=O)N3CCC2] |
| 35 | 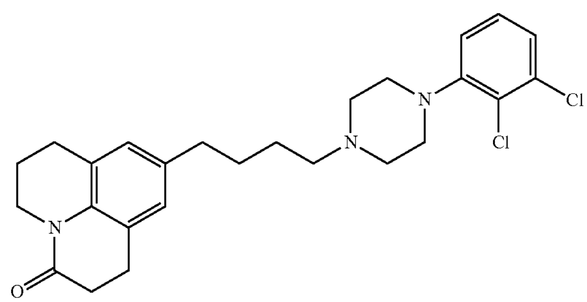 [SMILES: O=C1CCc2cc(CCCCN3CCN(c4cccc(Cl)c4Cl)CC3)cc3c2N1CCC3] |
| 36 | 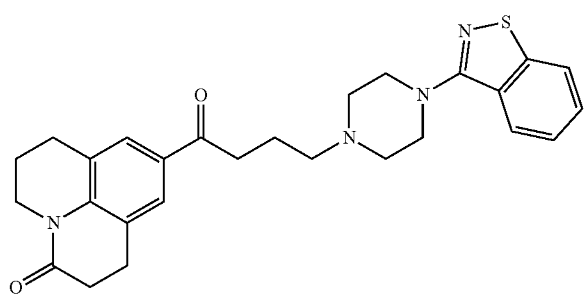 [SMILES: O=C(CCCN1CCN(c2nsc3ccccc23)CC1)c1cc2c3c(c1)CCC(=O)N3CCC2] |
| 37 | 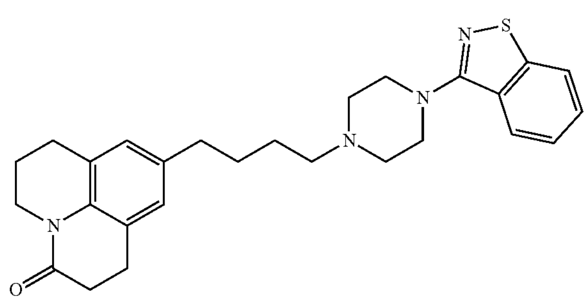 [SMILES: O=C1CCc2cc(CCCCN3CCN(c4nsc5ccccc45)CC3)cc3c2N1CCC3] |

TABLE 1-continued

Numbers and structures of the preferable compounds prepared in the Examples

| No. | Structure |
|---|---|
| 38 | 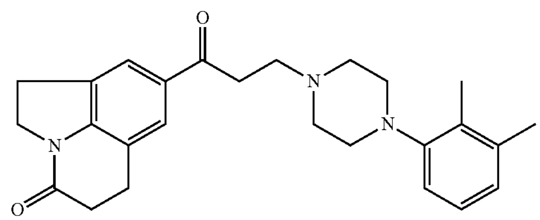 [SMILES: Cc1cccc(N2CCN(CCC(=O)c3cc4c5c(c3)CCN5C(=O)CC4)CC2)c1C] |
| 39 | 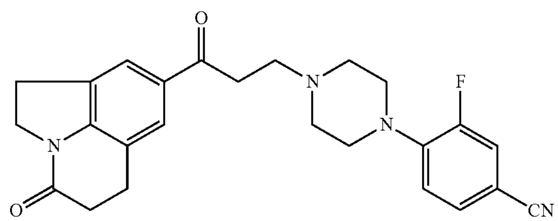 [SMILES: N#Cc1ccc(N2CCN(CCC(=O)c3cc4c5c(c3)CCN5C(=O)CC4)CC2)c(F)c1] |
| 40 | 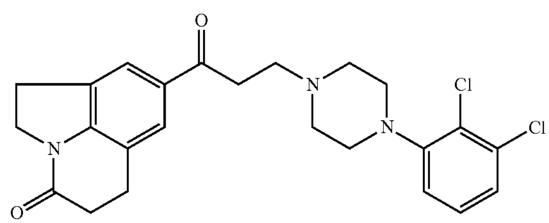 [SMILES: O=C(CCN1CCN(c2cccc(Cl)c2Cl)CC1)c1cc2c3c(c1)CCN3C(=O)CC2] |
| 41 | 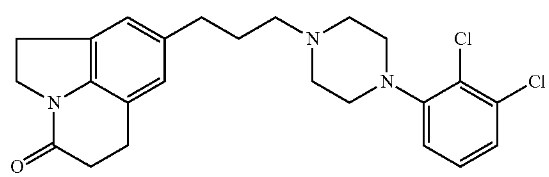 [SMILES: O=C1CCc2cc(CCCN3CCN(c4cccc(Cl)c4Cl)CC3)cc3c2N1CC3] |
| 42 | 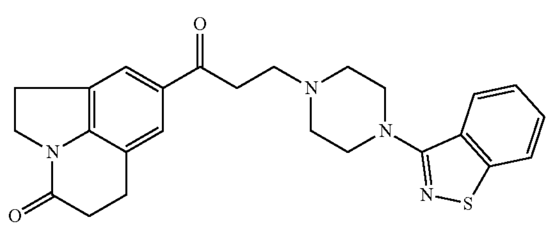 [SMILES: O=C(CCN1CCN(c2nsc3ccccc23)CC1)c1cc2c3c(c1)CCN3C(=O)CC2] |
| 43 | 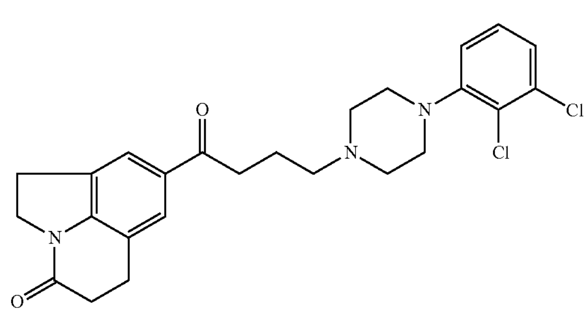 [SMILES: O=C(CCCN1CCN(c2cccc(Cl)c2Cl)CC1)c1cc2c3c(c1)CCN3C(=O)CC2] |

TABLE 1-continued

Numbers and structures of the preferable compounds prepared in the Examples

| No. | Structure |
|---|---|
| 44 | 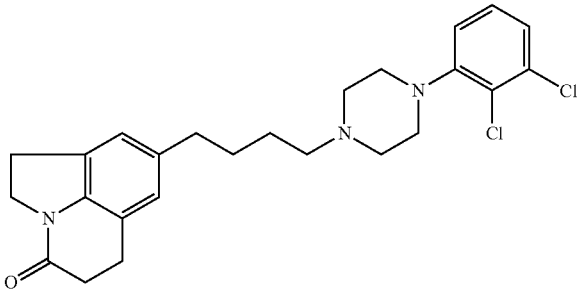 [SMILES: O=C1CCc2cc(CCCCN3CCN(c4cccc(Cl)c4Cl)CC3)cc3c2N1CC3] |
| 45 | 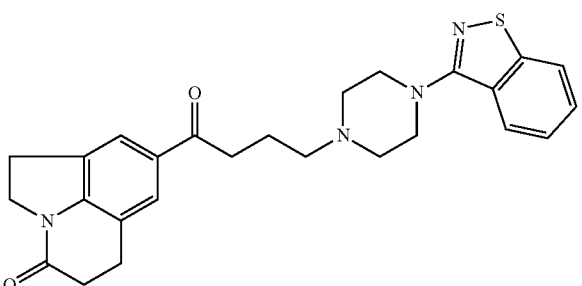 |
| 46 | 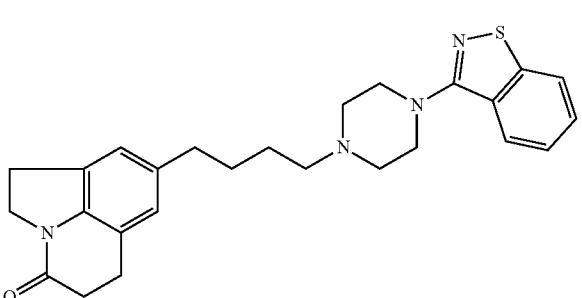 |

PHARMACOLOGICAL EXAMPLES

Homogenates used in the following examples, including homogenate A, homogenate B, homogenate C, homogenate E and homogenate F, are prepared respectively using methods as follows:

Homogenate A contains Tris-HCl buffer (final concentration 0.01M) and sucrose solution (final concentration 0.32M), pH 7.4.

Homogenate B is 0.01 M Tris-HCl buffer, pH 7.4.

Homogenate C is 50 mM Tris-HCl buffer, pH 7.4.

Homogenate E is 0.05 M Tris-HCl buffer, containing 5 mM EDTA, pH 7.4.

Homogenate F: potassium dihydrogen phosphate 1.36 g, 0.1 mol/L sodium hydroxide 79 ml, metered to 200 ml with double-distilled water, PH=7.4.

Example 47

Preparation of $5HT_{1A}$ Membrane

Rats were decapitated on ice. Striatum of brain was rapidly taken, and 2 striatums were combined into a centrifuge tube, to which 3 ml of buffer (0.05M Tris-HCl buffer, containing 0.1% ascorbic acid, 10 μm pargyline and 4 mM $CaCl_2$) was added. Homogenization was conducted for 3-4 s at level 4 for four times, and then 5 ml of buffer (0.05 M Tris-HCl buffer, containing 0.1% ascorbic acid, 10 μm pargyline and 4 mM $CaCl_2$) was added. Incubation at 37° C. was conducted for 10 min. The weight of the tubes were adjusted using a balance after incubation. Centrifugation was conducted at 12000 rpm, 4° C. for 20 min. The supernatant was discarded, and 3 ml of homogenate B was added, vortex mixer was used for blending, and then 5 ml of homogenate C was added. Centrifugation was conducted and repeated 3 times. After the centrifugation, the supernatant was discarded, and the pellets were stored at −80° C. for future use.

Materials for the Receptor Binding Assay

Isotope ligand $^3$H-8-OH-DPAT (67.0 Ci/mmol) was purchased from PerkinElmer Company; 5-HT was purchased from RBI Company; GF/C glass fiber filter paper was purchased from Whatman Company; Tris was imported and divided into aliquots; PPO, POPOP were purchased from Shanghai No. 1 Reagent Factory; liposoluble scintillation cocktail was purchased from Shanghai Reagent Factory; Beckman LS-6500 Multi-function Liquid Scintillation Counter was used.

Procedures (1) The prepared membrane was first applied with appropriate amount of homogenate A, and homogenizer was used for evenly dispersing. 15 tubes were mixed into a 100 ml container, and appropriate amount of homogenate A was added to give 50 ml of membrane suspension, which was reserved for future use.

(2) 100 μL of membrane preparation and 100 μL of homogenate A were added into each reaction tube.

(3) 100 μL of homogenate A was added into the total binding tube (TB), 100 μL of 5-HT (final concentration $10^{-5}$ M) was added into the nonspecific binding tube (NB), and 100 μL of the test compound (final concentration $10^{-5}$ M) was added into the specific binding tube (SB) of each test compound.

(4) 10 μL of radioactive ligand $^3$H-8-OH-DPAT was respectively added into each reaction tube (2 parallel tubes were used for each reaction tube, and each of them was placed on ice when adding sample).

(5) Each reaction tube was incubated at 37° C. for 10 min; after the reaction was completed, the bound ligands were rapidly filtered under reduced pressure, and sufficiently washed with ice-chilled assay buffer. The filter was taken out and put into a 3 ml scintillation vial, and 2 ml of toluene scintillation cocktail was added and blended.

(6) The scintillation vials were put into Liquid Scintillation Counter for counting.

Inhibition rate (I %)=(Total binding tube cpm−compound cpm)/(Total binding tube cpm−nonspecific binding tube cpm)×100%

Each assay for the compounds was conducted in duplicate for two individual tests.

The results are listed in Table 2.

Example 48

Preparation of 5HT$_{2A}$ Membrane

Rats were decapitated on ice. Striatum of brain was rapidly taken, and 2 striatums were combined into a centrifuge tube, to which 3 ml of buffer (0.05 M Tris-HCl buffer: 6.05 g of Tris was dissolved in 1000 ml of double-distilled water, and concentrated HCl was used to adjust to pH 7.5) was added, homogenization was conducted for 3-4 s at level 4 for four times, and then 5 ml of buffer was added. Incubation was conducted at 37° C. for 10 min, the weight of the tubes were adjusted using a balance after incubation. Centrifugation was conducted, the supernatant was discarded, and 3 ml of homogenate A was added. Vortex mixer was used for blending, and then 5 ml of buffer was added. Centrifugation was conducted. After the centrifugation, the supernatant was discarded, and the pellets were stored at −80° C. for future use.

Materials for the Receptor Binding Assay

Isotope ligand [$^3$H]-Ketanserin (67.0 Ci/mmol) was purchased from PerkinElmer Company; Methysergide was purchased from RBI Company; GF/C glass fiber filter paper was purchased from Whatman Company; Tris was imported and divided into aliquots; PPO and POPOP were purchased from Shanghai No. 1 Reagent Factory; liposoluble scintillation cocktail was purchased from Shanghai Reagent Factory; Beckman LS-6500 Multi-function Liquid Scintillation Counter was used.

Procedures (1) The prepared membrane was first applied with homogenate A, and homogenizer was used for evenly dispersing. 15 tubes were mixed into a 100 ml container, and appropriate amount of homogenate A was added to give 50 ml of membrane suspension, which was reserved for future use.

(2) 100 μL of membrane preparation and 100 μL of buffer were added into each reaction tube.

(3) 100 μL of homogenate A was added into the total binding tube (TB), 100 μL of Methysergide (final concentration $10^{-5}$ M) was added into the nonspecific binding tube (NB), and 100 μL of the test compound (final concentration $10^{-5}$ M) was added into the specific binding tube (SB) of each compound.

(4) 10 μL of radioactive ligand $^3$H-Ketanserin was respectively added into each reaction tube (2 parallel tubes were used for each reaction tube, and each of them was placed on ice when adding sample).

(5) Each of the reaction tubes was incubated at 37° C. for 15 min. After the reaction was completed, the bound ligands were rapidly filtered under reduced pressure, and sufficiently washed with ice-chilled assay buffer. The filter was taken out and put into a 3 ml scintillation vial, and 2 ml of toluene scintillation cocktail was added and blended.

(6) The scintillation vials were put into Liquid Scintillation Counter for counting.

Inhibition rate (I %)=(Total binding tube cpm−compound cpm)/(Total binding tube cpm−nonspecific binding tube cpm)×100%

Each assay for the compounds was conducted in duplicate for two individual tests.

The results are listed in Table 2.

Example 49

Preparation of D$_2$ Membrane

Rats were decapitated on ice. Striatum of brain was rapidly taken, and 2 striatums were combined into a centrifuge tube, to which 3 ml of buffer (0.05 M Tris-HCl buffer, containing NaCl 120 mM, KCl 5 mM, MgCl$_2$ 1 mM, CaCl$_2$ 1 mM) was added, homogenization was conducted for 3-4 s at level 4 for four times, and then 5 ml of buffer was then added. The weight of the homogenized tubes were adjusted using a balance, and centrifugation was conducted. The supernatant was discarded, and 3 ml of homogenate B was added. Vortex mixer was used for blending, and then 5 ml of homogenate B was added. Centrifugation was conducted. The supernatant was discarded, and the pellets were stored at −80° C. for future use.

Materials for the Receptor Binding Assay

Isotope ligand $^3$H-Spiperone (67.0 Ci/mmol) was purchased from PerkinElmer Company; Butaclamol was purchased from RBI Company; GF/C glass fiber filter paper was purchased from Whatman Company; Tris was imported and divided into aliquots; PPO and POPOP were purchased from Shanghai No. 1 Reagent Factory; liposoluble scintillation cocktail was purchased from Shanghai Reagent Factory; Beckman LS-6500 Multi-function Liquid Scintillation Counter was used.

Procedures (1) The prepared membrane was first applied with appropriate amount of homogenate A, and homogenizer was used for evenly dispersing. 15 tubes were mixed into a 100 ml container, and appropriate amount of homogenate B was added to give 50 ml of membrane suspension, which was reserved for future use.

(2) 100 μL of membrane preparation and 100 μL of buffer were added into each reaction tube.

(3) 100 μL of homogenate A was added into the total binding tube (TB), 100 μL of Butaclamol (final concentration $10^{-5}$ M) was added into the nonspecific binding tube (NB), and 100 μL of the test compound (final concentration 10⁻⁵ M) was added into the specific binding tube (SB) of each compound.

(4) 10 μL of radioactive ligand ³H-Spiperone was respectively added into each reaction tube (2 parallel tubes were used for each reaction tube, and each of them was placed on ice when adding sample).

(5) Each of the reaction tubes was incubated at 37° C. for 20 min. After the reaction was completed, the bound ligands were rapidly filtered under reduced pressure, and sufficiently washed with ice-chilled assay buffer. The filter was taken out and put into a 3 ml scintillation vial, and 2 ml of toluene scintillation cocktail was added and blended.

(6) The scintillation vials were put into Liquid Scintillation Counter for counting.

Inhibition rate ($I$ %)=(Total binding tube cpm−compound cpm)/(Total binding tube cpm−nonspecific binding tube cpm)×100%

Each assay for the compounds was conducted in duplicate for two individual tests.

The results are listed in Table 2.

Example 50: $D_3$ Receptor Assay

Cells

In HEK-293 cells, receptor proteins were expressed on membrane in large amount after 48-72 hours. Then the cells were centrifuged at 1000 rpm for 5 min, the supernatant was discarded, and the cell pellets was collected and stored in a −20° C. fridge for reservation. It was re-suspended with Tris-Cl (pH 7.4) when the assay was performed.

Materials for the Assay $D_3$ receptor isotope ligand [³H]-Spiperone was purchased from Amersham Company; (+) Butaclamol was purchased from RBI Company; GF/C glass fiber filter paper was purchased from Whatman Company; liposoluble scintillation cocktail was purchased from Shanghai Reagent Factory; Beckman LS-6500 Multi-function Liquid Scintillation Counter was used. Tris was divided into aliquots by Genetimes Technology Inc.

Procedures

Competitive binding test for receptors: 20 μl of each of the test compounds and 20 μl of the radioactive ligand together with 160 μl of the receptor proteins were added into the reaction tubes, and the final concentrations of the test compound and the positive drug were all 10 μmol/L. After 50 min of incubation in 30° C. water bath, the tubes were immediately moved to ice bath to terminate the reactions. GF/C glass fiber filter papers were used for rapid sucking filtration on a Millipore cell sample collector, 3 ml of elution buffer (50 mM Tris-HCl, PH 7.4) was applied for 3 times, and microwave was applied for 4-5 min for drying. The filter paper was moved into 0.5 ml centrifuge tube, and 500 μl of liposoluble scintillation cocktail was added. The tubes were allowed to stand still for over 30 min in dark, and the intensities of radioactivity were measured by a counter. The percentage of inhibition rates of each compound against the binding of isotope ligands were calculated according to the following formula:

Inhibition rate ($I$ %)=(Total binding tube cpm−compound cpm)/(Total binding tube cpm−nonspecific binding tube cpm)×100%

The results are listed in Table 2.

Example 51

Preparation of $5HT_{2C}$ Membrane

Rats were decapitated on ice. Striatum of brain was rapidly taken, and 2 striatums were combined into a centrifuge tube, to which 3 ml of buffer (0.05 M Tris-HCl buffer: 6.05 g of Tris was dissolved in 1000 ml of double-distilled water, and concentrated HCl was used to adjust to pH 7.5) was added, homogenization was conducted for 3-4 s at level 4 for four times, and then 5 ml of buffer was added. Incubation was conducted at 37° C. for 10 min, the weight of the tubes were adjusted using a balance after the incubation. Centrifugation was conducted at 12000 r, 4° C. for 20 min, the supernatant was discarded, and 3 ml of homogenate A was added. Vortex mixer was used for blending, and then 5 ml of buffer was added. Centrifugation was conducted. After the centrifugations, the supernatant was discarded, and the pellets were stored at −80° C. for future use.

Materials for the Receptor Binding Assay

Isotope ligand [³H]-mesulergine (67.0 Ci/mmol) was purchased from PerkinElmer Company; mianserin was purchased from RBI Company; GF/C glass fiber filter paper was purchased from Whatman Company; Tris was imported and divided into aliquots; PPO and POPOP were purchased from Shanghai No. 1 Reagent Factory; liposoluble scintillation cocktail was purchased from Shanghai Reagent Factory. Beckman LS-6500 Multi-function Liquid Scintillation Counter was used.

Procedures (1) The prepared membrane was first applied with appropriate amount of homogenate A, and homogenizer was used for evenly dispersing. 15 tubes were mixed into a 100 ml container, and appropriate amount of homogenate A was added to give 50 ml of membrane suspension, which was reserved for future use.

(2) 100 μL of membrane preparation and 100 μL of buffer were added into each reaction tube.

(3) 100 μL of homogenate A was added into the total binding tube (TB), 100 μL of mianserin (final concentration 10⁻⁵ M) was added into the nonspecific binding tube (NB), and 100 μL of the test compound (final concentration 10⁻⁵ M) was added into the specific binding tube (SB) of each compound.

(4) 10 μL of radioactive ligand [³H]-mesulergine was respectively added into each reaction tube (2 parallel tubes were used for each reaction tube, and each of them was placed on ice when adding sample).

(5) Each of the reaction tubes was incubated at 37° C. for 15 min. After the reaction was completed, the bound ligands were rapidly filtered under reduced pressure, and the ice-chilled assay buffer was used for adequate washing. The filter was taken out and put into a 3 ml scintillation vial, and 2 ml of toluene scintillation cocktail was added and blended.

(6) The scintillation vials were put into Liquid Scintillation Counter for counting.

Inhibition rate ($I$ %)=(Total binding tube cpm−compound cpm)/(Total binding tube cpm−nonspecific binding tube cpm)×100%

Each assay for the compounds was conducted in duplicate for two individual tests.

Example 52

Preparation of Histamine $H_1$ Receptor Membrane

Rats were decapitated on ice. Cerebellum of the rat was rapidly taken and homogenate F was added. Vortex mixer was used for blending. Centrifugation was conducted at 4° C.

The supernatant was discarded to give pellets, and homogenate F was added again to the pellets for washing. Centrifugation was conducted and repeated 3 times. After the centrifugations, the supernatant was discarded, and the pellets were stored at −80° C. for future use.

$H_1$ Receptor Binding Assay (1) The prepared membrane was first applied with appropriate amount of homogenate F, and homogenizer was used for evenly dispersing. 15 tubes were mixed into a 100 ml container, and appropriate amount of homogenate F was added to give 50 ml of membrane suspension, which was reserved for future use.

(2) 100 μL of membrane preparation was added into each reaction tube.

(3) 100 μL of homogenate F was added into the total binding tube (TB), 100 μL of promethazine (purchased from RBI company, final concentration $10^{-5}$ M) was added into the nonspecific binding tube (NB), and 100 μL of the test compound (final concentration $10^{-5}$ M) was added into the specific binding tube (SB) of each compound.

(4) 10 μL of radioactive ligand $^3$H-pyrilamine (purchased from PerkinElmer Company) was respectively added into each reaction tube (2 parallel tubes were used for each reaction tube, and each of them was placed on ice when adding sample).

(5) Each of the reaction tubes was incubated at 30° C. for 60 min. After the reaction was completed, the bound ligands were rapidly filtered under reduced pressure, and the ice-chilled assay buffer was used for adequate washing. The filter was taken out and put into a 3 ml scintillation vial, and 2 ml of toluene scintillation solution was added and blended.

(6) The scintillation vials were put into Liquid Scintillation Counter for counting.

Inhibition rate (I %)=(Total binding tube cpm−compound cpm)/(Total binding tube cpm−nonspecific binding tube cpm)×100%

Each assay for the compounds was conducted in duplicate for two individual tests.

Example 53

Preparation of Receptor Membrane of Norepinephrine

Rats were decapitated on ice. Cortex of brain was rapidly taken, and homogenate E was added. Vortex mixer was used for blending. Centrifugation was conducted at 48000 g, 4° C. for 15 min. The supernatant was discarded to give pellets, and 0.05 M Tris-HCl buffer (PH7.7) was added again to the pellets for washing, and then centrifugation was conducted and repeated 3 times. After the centrifugations, the supernatant was discarded, and the pellets were stored at −80° C. for future use.

$\alpha_1$ Norepinephrine Receptor Binding Assay (1) The prepared membrane was first applied with appropriate amount of homogenate E, and homogenizer was used for evenly dispersing. 15 tubes were mixed into a 100 ml container, and appropriate amount of homogenate E was added to give 50 ml of membrane suspension, which was reserved for future use.

(2) 100 μL of membrane preparation and 100 μL of homogenate E were added into each reaction tube.

(3) 100 μL of homogenate E was added into the total binding tube (TB), 100 μL of prazosin (purchased from PerkinElmer company, final concentration $10^{-5}$ M) was added into the nonspecific binding tube (NB), and 100 μL of the test compound (final concentration $10^{-5}$ M) was added into the specific binding tube (SB) of each compound.

(4) 10 μL of radioactive ligand $^3$H-prazosin (purchased from PerkinElmer Company) was respectively added into each reaction tube (2 parallel tubes were used for each reaction tube, and each of them was placed on ice when adding sample).

(5) Each of the reaction tubes was incubated at 25° C. for 60 min. After the reaction was completed, the bound ligands were rapidly filtered under reduced pressure, and the ice-chilled assay buffer was used for adequate washing. The filter was taken out and put into a 3 ml scintillation vial, and 2 ml of toluene scintillation solution was added and blended.

(6) The scintillation vials were put into Liquid Scintillation Counter for counting.

Inhibition rate (I %)=(Total binding tube cpm−compound cpm)/(Total binding tube cpm−nonspecific binding tube cpm)×100%

Each assay for the compounds was conducted in duplicate for two individual tests.

The results are listed in Table 2.

The results of in vitro assay indicated that, the compounds of the invention (especially compounds 5, 6, 12, 13, 14, 16 and 17) have high affinities with four receptors ($D_2$, $D_3$, $5HT_{1A}$, $5HT_{2A}$), and low affinities with $5HT_{2C}$, $H_1$ and $\alpha_1$.

Example 54: MK-801 Induced High Activity—the In Vivo Anti-Schizophrenia Activity of the Compounds Animals and Reagents Healthy mice of Kunming breed (with half male and half female, (20±2) g) were provided by Qinglongshan Animal Cultivation Center, Nanjing.

Ascorbic acid was provided by Sinopharm Chemical Reagent Co. Ltd.

MK-801 was produced by Sigma Company, USA; the formulation method: 0.1% vitamin C was used to formulate a 1 mg/ml solution.

Test positive drugs: haloperidol, clozapine, risperidone, olanzapine, aripiprazole, ziprasidone, quetiapine.

Tween 80, with the concentration of 10%.

Procedures

Mice with qualified body weight were selected, and randomly divided into blank group, model group, positive control group (risperidone group) and drug group. 10% Tween was administered intragastrically to the blank group and the model group at 0.1 ml/10 g; risperidone was administered intragastrically to the positive control group at 0.1 mg/kg; and corresponding amounts of drugs were administered intragastrically to the drug groups, respectively. 1 h after the administration, 0.1% concentration of ascorbic acid was intraperitoneally injected to the blank group at 0.1 ml/10 g; and the model group, the positive control group (30 min) and the drug group were intraperitoneally injected the MK-801 solution at 0.1 mg/kg. Subsequently, the spontaneous activities of the mice of each group in 90 min were measured. The results are listed in Table 3.

Example 55: Apomorphine Induced Clambering Assay of Mice

Animals

Healthy mice of Kunming breed (KM) (male, with body weight of 18-22 g) were provided by Qinglongshan Animal Cultivation Center, Nanjing.

Main Reagents

Test positive drugs: haloperidol, clozapine, risperidone, olanzapine, aripiprazole, ziprasidone, quetiapine.

Apomorphine provided by Sigma Company was dissolved in 0.9% NaCl (containing 0.1% vitamin C) before use, and was freshly formulated before use.

Vitamin C, F20061113, was provided by Sinopharm Chemical Reagent Co. Ltd.

Sodium chloride injection, H32026305, was provided by Xuzhou No. 5 Pharmaceutical Factory Co. Ltd.

Instruments: self-made clambering cage, chronograph.

Procedures: apomorphine induced clambering assay of mice

KM mice (male, with body weight of 18-22 g) were randomly divided into negative control group, model group, positive drug groups of each dosage (risperidone, aripiprazole, ziprasidone, quetiapine, olanzapine, haloperidol, clozapine), and compound groups of each dosage (the specific dosages are listed in the following Table), with 10 mice of each group. Corresponding solvent double-distilled water was administered intragastrically to the negative control group and the model group, corresponding positive drugs were administered intragastrically to the positive drug groups (a small amount of acetic acid was first added and then double-distilled water was added when dissolving), and corresponding dosages of compounds were administered intragastrically to the compound groups of each dosage, with the volume for intragastric administration as 0.1 ml/10 g. 1 hour after the intragastric administration, apomorphine was subcutaneously injected (1 mg/kg), with the volume as 0.1 ml/10 g. After the injection of apomorphine, the mice were immediately put into the clambering cages. After 5 min of adaptation, the behavior of the mice at 10-11, 20-21, and 30-31 min after the injection of apomorphine were observed and scored. Scoring criteria: the behavior of 4 paws on the floor was scored as 0; the behavior of 2 forepaws on the cage was scored as 1; and the behavior of 4 paws on the cage was scored as 2.

The results are listed in table 3.

Example 56: Catalepsy Assay

Animals

Healthy mice of Kunming breed (with half male and half female, (22±2) g) were provided by Qinglongshan Animal Cultivation Center, Nanjing.

Main reagents: the test drugs, haloperidol, clozapine, risperidone, olanzapine, aripiprazole, ziprasidone.

Instruments: self-made bar-grabbing apparatus: stainless steel bar in mice box, which was 0.3 cm in diameter and 5 cm above the bench.

Procedures

KM mice (half male and half female, with body weight of 20-24 g) were randomly divided into negative control group, model group, positive drug groups of each dosage (risperidone, aripiprazole, ziprasidone, quetiapine, olanzapine, haloperidol, clozapine), and compound groups of each dosage, with 10 mice in each group. Corresponding solvent double-distilled water was administered intragastrically to the negative control group and the model group, corresponding positive drugs were administered intragastrically to the positive drug groups (a small amount of acetic acid was first added and then double-distilled water was added when dissolving), and corresponding dosages of compounds were administered intragastrically to the compound groups for each dosage, with the volume for intragastric administration as 0.1 ml/10 g. At 30 min, 60 min, 90 min after the intragastric administration, the two forepaws of the mice were gently placed on the bars (which were 20 cm in length, 0.3 cm in diameter, and 5.5 cm above the bench), and the hindpaws of the animals were placed on the bottom of the box. The durations of the mice to maintain the posture with the two forepaws on the bars were recorded, and 30 s of spasticity without moving was considered as the positive response. In the case the forepaws of the mice were not put down persistently, the observation was terminated at 60 s. The numbers of animals with positive response in each of the compound dosage groups were counted.

The results are listed in Table 3.

The results indicated that, when compared with the model group, risperidone and the compound of the invention can not only significantly improve the MK-801 induced high activity, but also effectively improve the apomorphine induced clambering symptoms, and they did not cause EPS at effective dosage, indicating that they have notable anti-schizophrenia effects.

Example 57: Acute Toxicity Study

Limit test of sequential assay: KM mice (half male and half female) were randomly divided into several groups (with 2-5 mice in each group), which were respectively the 2000 mg/kg groups for each compound, and the solvent group. 0.2 ml/10 g were administered intragastrically. The deaths of the animals in 3 days were observed. In the case 3 or more animals survived in 3 days without notable abnormity in their life states, the observation was continued until the assay was completed in 7 days. In the case 3 or more animals died in 3 days, the method of median lethal dose was used to determine the $LD_{50}$.

Pre-assay for the method of the median lethal dose: KM mice (half male and half female) were randomly divided into several groups (with 4 mice in each group), which were respectively the 1500 mg/kg, 1000 mg/kg, 500 mg/kg groups for each compound, and the solvent group. 0.2 ml/10 g were administered intragastrically, and the deaths of the animals in 1-3 days were observed.

Results: The $LD_{50}$ of single intragastric administration in mice of the compound of the invention was greater than 2000 mg/kg, which was comparable to ziprasidone (>2000 mg/kg), and was far greater than risperidone (82.1 mg/kg) and aripiprazole (93 mg/kg), indicating a relatively low acute toxicity.

TABLE 2

The inhibition rate of the compounds for each receptor

| No. | $D_2$ Inhibition rate (%) | $5HT_{1A}$ Inhibition rate (%) | $5HT_{2A}$ Inhibition rate (%) | $D_3$ Inhibition rate (%) | $5HT_{2C}$ Inhibition rate (%) | $H_1$ Inhibition rate (%) | $\alpha_1$ Inhibition rate (%) |
|---|---|---|---|---|---|---|---|
| 1 | 45.89 | 54.62 | 84.93 | 60.90 | 84.62 | 84.93 | 68.75 |
| 2 | 94.33 | 93.94 | 97.86 | 74.93 | 63.94 | 47.86 | 68.75 |
| 3 | 97.67 | 91.62 | 92.54 | 93.86 | 61.62 | 42.54 | 51.42 |
| 4 | 94.22 | 88.00 | 93.99 | 92.54 | 60.00 | 43.99 | 60.91 |
| 5 | 99.40 | 99.76 | 99.48 | 97.99 | 66.76 | 44.48 | 43.75 |
| 6 | 98.48 | 99.62 | 99.10 | 98.48 | 61.62 | 49.10 | 60.91 |
| 7 | 94.32 | 99.16 | 99.36 | 98.10 | 62.16 | 46.36 | 63.69 |
| 8 | 90.17 | 89.46 | 93.00 | 72.36 | 59.46 | 45.46 | 41.19 |
| 9 | 91.76 | 84.03 | 90.23 | 86.00 | 54.03 | 46.03 | 66.62 |
| 10 | 85.88 | 82.94 | 83.45 | 80.23 | 55.94 | 43.94 | 46.48 |
| 11 | 55.89 | 58.62 | 74.93 | 83.45 | 84.62 | 84.93 | 52.42 |
| 12 | 97.75 | 96.49 | 94.36 | 94.93 | 56.49 | 41.36 | 58.91 |
| 13 | 96.83 | 93.58 | 96.86 | 94.36 | 53.58 | 46.86 | 53.75 |
| 14 | 94.65 | 87.03 | 93.92 | 96.86 | 57.03 | 43.92 | 50.91 |
| 15 | 103.83 | 102.70 | 103.99 | 99.92 | 52.70 | 33.99 | 43.69 |
| 16 | 98.34 | 99.41 | 98.79 | 98.34 | 55.41 | 38.79 | 51.19 |
| 17 | 99.17 | 99.08 | 99.37 | 96.17 | 51.08 | 35.37 | 46.62 |
| 18 | 88.10 | 84.32 | 87.79 | 98.10 | 54.32 | 37.79 | 56.48 |
| 19 | 81.45 | 87.10 | 81.08 | 91.45 | 57.10 | 41.08 | 52.47 |
| 20 | 83.23 | 83.02 | 80.31 | 93.23 | 53.02 | 49.31 | 68.86 |
| 21 | 92.01 | 93.30 | 91.12 | 90.10 | 67.89 | 54.34 | 46.78 |
| 22 | 93.12 | 91.23 | 90.23 | 91.24 | 76.34 | 45.23 | 53.46 |
| risperidone | 101.54 | 85.22 | 100.18 | 101.54 | 105.22 | 56.01 | 96.10 |

TABLE 3

Results of the in vivo animal model assay of the preferable compounds

| Compound No. | $LD_{50}$ (po, mg/kg) | MK-801 induced high activity ($ED_{50}$, po, mg/kg) | Apomorphine induced clambering ($ED_{50}$, po, mg/kg) | Catalepsy ($ED_{50}$, po, mg/kg) | Catalepsy/ MK-801 induced high activity | Catalepsy/ Apomorphine induced clambering |
|---|---|---|---|---|---|---|
| 2 | >2000 | 0.20 | 0.11 | 3.8 | 19 | 37 |
| 5 | >2000 | 2.20 | 1.31 | >200 | 90.90 | 152 |
| 7 | >2000 | 0.92 | 0.44 | 24.07 | 26 | 54 |
| 12 | >2000 | 0.06 | 0.076 | 8.45 | 140 | 111 |
| 15 | >2000 | 0.21 | 0.12 | 50 | 238 | 416 |
| haloperidol | 20 | 7.42 | 0.10 | 0.44 | 4.40 | 4.89 |
| clozapine | 150 | 2.28 | 17.92 | >50 | >21.93 | >5.58 |
| risperidone | 82.1 | 0.01 | 0.015 | 0.92 | 92.00 | 61.33 |
| olanzapine | 177 | 0.10 | 0.11 | 2.23 | 22.30 | 20.27 |
| aripiprazole | 93 | 0.12 | 0.66 | 2.40 | 20.00 | 11.43 |
| ziprasidone | >2000 | 0.56 | 0.37 | 30.40 | 54.29 | 82.16 |
| quetiapine | 800 | 10.1 | 2.02 | 800.00 | 79.21 | 396.04 |

Formulation Example

Example 58

Taking the dosage form of tablet as an example, the pharmaceutical composition of the invention was prepared according to the following formulations, using compounds prepared in Examples 1-46 as the active ingredient, respectively:

| | |
|---|---|
| Active Ingredient (the compound according to the invention) | 100 mg |
| microcrystalline cellulose | 50 mg |
| lactose | 100 mg |
| Povidone K30 | 9 mg |
| carboxymethyl starch sodium | 12 mg |
| silica | 2.5 mg |
| magnesium stearate | 1.5 mg |

The raw excipients were sieved with 80 mesh for use. The prescription doses of active ingredient, microcrystalline cellulose, lactose, Povidone K30 were weighed and introduced into a high speed mixing granulator, whereby they were mixed uniformly at low speed. An appropriate amount of purified water was added, the stirring was performed at low speed, and high speed shear granulation was carried out. The wet granules were dried at 60° C. for 3 hours, and sieved with 24 mesh. The prescription doses of carboxymethyl starch sodium, silica and magnesium stearate were added for mixing totally. The compression was performed in a rotary tablet press to give the tablet dosage form of the pharmaceutical composition.

In the present specification, the term "an embodiment", "some embodiments", "example", "specific example", or "some examples" and the like, mean that the specific feature, structure, material or characteristic described in conjunction with the embodiment or example is included in at least one embodiment or example of the invention. In the present specification, indicative descriptions for the terms mentioned above are not necessarily directed to the same embodiment or example. Furthermore, the specific feature, structure, material or characteristic as described can be combined in suitable ways in one or more embodiments or examples. In addition, unless contradicted to the contrary, combinations and bindings can be done among different embodiments or examples, and the features of different embodiments or examples of the specification by a person skilled in the art.

Although examples of the invention are already presented and described as above, it will be understood that, the examples as above are exemplary, and can not be interpreted as limitation to the invention. Alterations, modifications, replacements and variants can be done by a person skilled in the art within the scope of the invention.

The invention claimed is:

1. A compound of Formula (I), or a pharmaceutically acceptable salt or thereof,

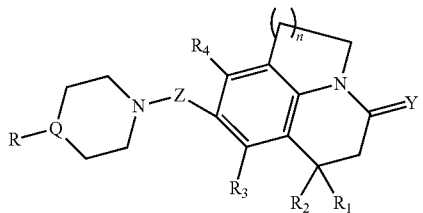

(I)

wherein:

Z is —(CH$_2$)$_m$—, which is unsubstituted or substituted by one or more substituents selected from the group consisting of hydroxy, oxo and C$_{1-5}$ alkyl, m is an integer of 2~5;

Y is O or S;

Q is N or CH;

n=1, 2 or 3;

R$_1$, R$_2$, R$_3$ or R$_4$ is each independently hydrogen, halogen, C$_{1-5}$ alkyl, wherein the C$_{1-5}$ alkyl is unsubstituted or substituted by one or more substituents selected from the group consisting of halogen, amino and hydroxy;

R is phenyl, or a group of Formula (II), Formula (III) or Formula (IV), wherein the above groups are unsubstituted or substituted by one or more substituents selected from the group consisting of halogen, cyano, C$_{1-5}$ alkyl, C$_{1-5}$ alkoxyl and hydroxy;

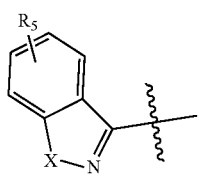

(II)

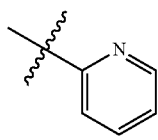

(III)

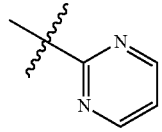

(IV)

wherein, X in Formula (II) is O, R$_5$ is H or halogen.

2. The compound according to claim 1 or the pharmaceutically acceptable salt or thereof, wherein Z is —(CH$_2$)$_m$—, which is unsubstituted or substituted by one or more substituents selected from the group consisting of hydroxy, oxo and methyl, m is an integer of 2~5.

3. The compound according to claim 1 or the pharmaceutically acceptable salt or thereof, wherein the halogen is fluorine, chlorine, bromine or iodine.

4. The compound according to claim 1 or the pharmaceutically acceptable salt or thereof, wherein R is a group of Formula (II), wherein, R$_5$ is selected from the group consisting of fluorine, chlorine, bromine and iodine; or R is phenyl, which is substituted by one or more substituents selected from the group consisting of methoxyl, methyl, ethyl, fluorine, chlorine, bromine, iodine and cyano.

5. The compound according to claim 1 or the pharmaceutically acceptable salt or thereof, wherein R$_1$, R$_2$, R$_3$ or R$_4$ is each independently hydrogen, phenyl, halogenated phenyl, C$_{1-5}$ alkyl, halogenated C$_{1-5}$ alkyl or C$_{1-5}$ hydroxyalkyl.

6. The compound according to claim 1 or the pharmaceutically acceptable salt or thereof, wherein Z is —(CH$_2$)$_m$—, which is unsubstituted or substituted by one or more substituents selected from the group consisting of hydroxy and oxo, m is an integer of 2~5;

Y is O or S;

Q is N or CH;

n=1, 2 or 3;

R$_1$, R$_2$, R$_3$ or R$_4$ is each independently hydrogen, fluorine, phenyl, methyl, ethyl or propyl;

R is unsubstituted phenyl, a group of Formula (III) or a group of Formula (IV); or R is a group of Formula (II), wherein, R$_5$ is selected from the group consisting of fluorine and chlorine; or R is phenyl, which is substituted by one or more substituents selected from the group consisting of methoxyl, methyl, ethyl, fluorine, chlorine, bromine and cyano.

7. The compound according to claim 1 or the pharmaceutically acceptable salt or thereof, wherein the compound is selected from:

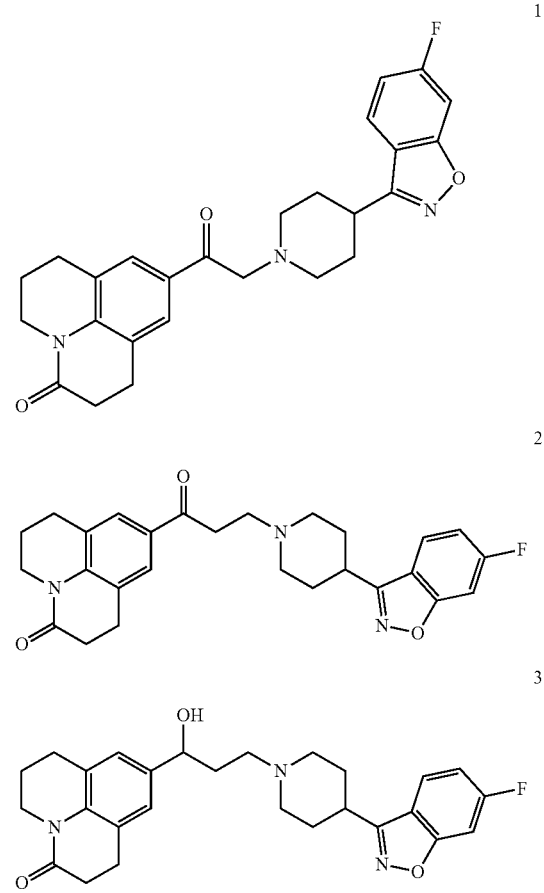

-continued
12
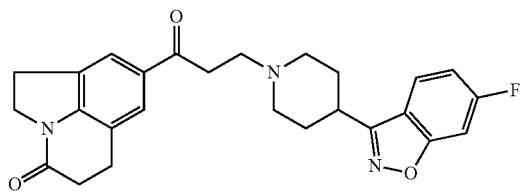
13
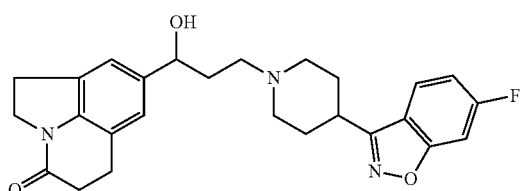
14
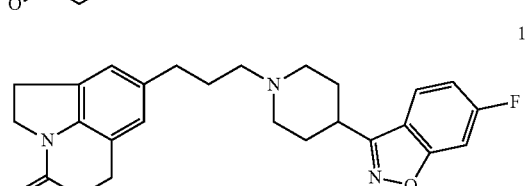
15
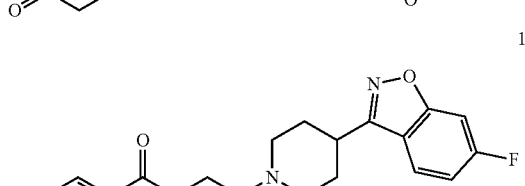
16
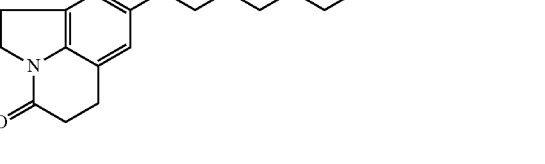
17
-continued
18
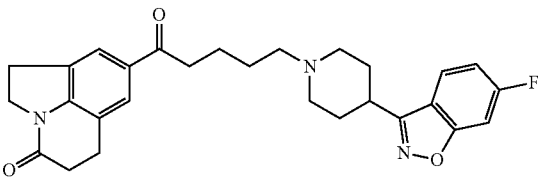
19
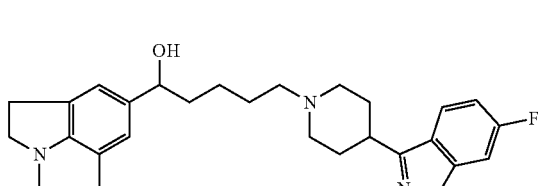
20
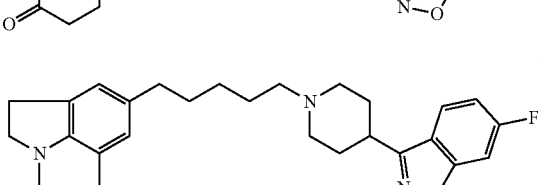
21
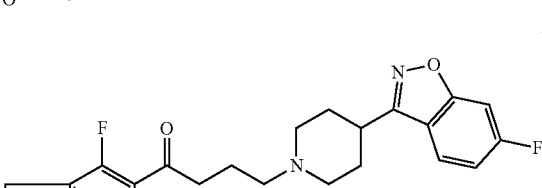
22
23
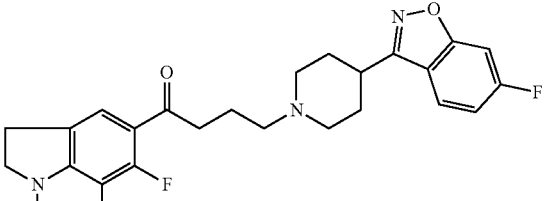
24
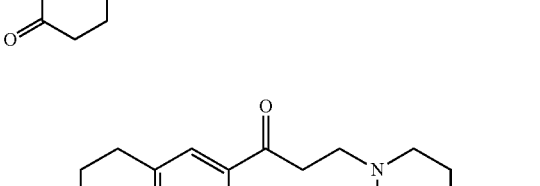

25
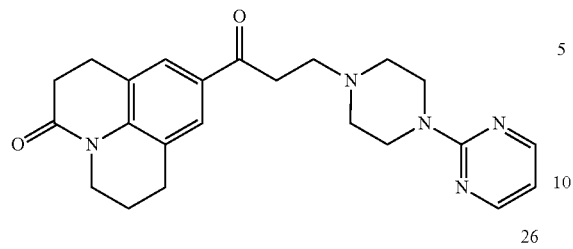
26
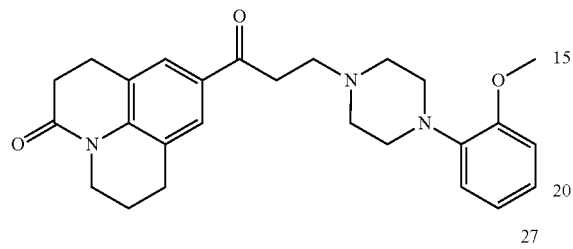
27
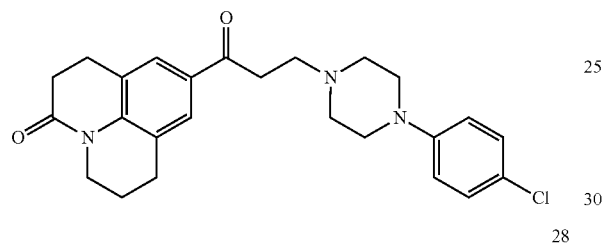
28
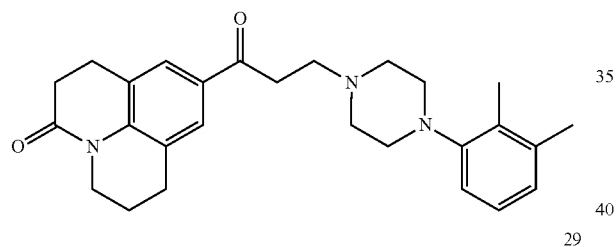
29
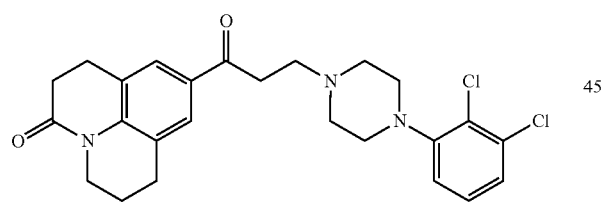
30
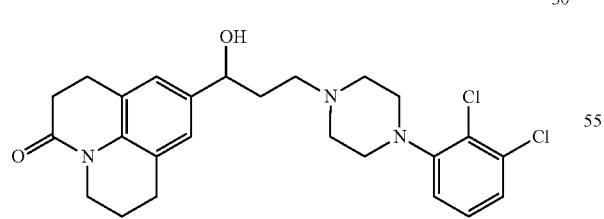
31
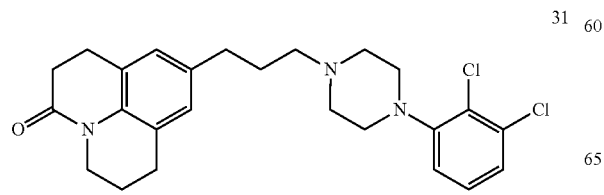
33
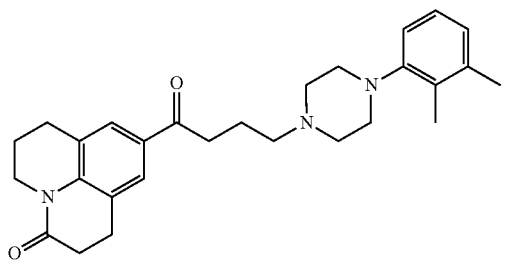
34
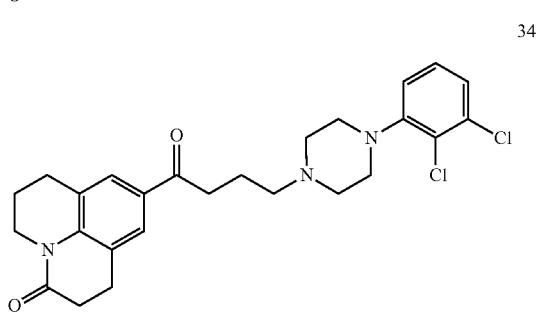
35
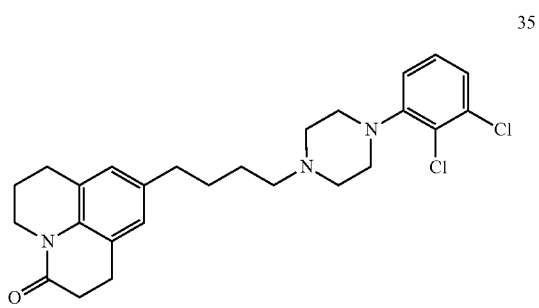
38
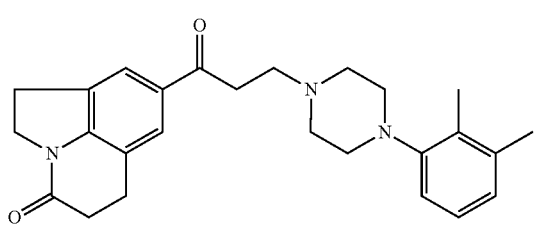
39
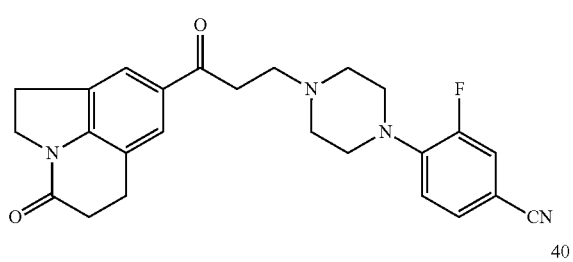
40
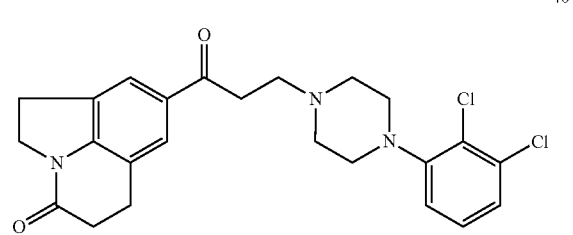

41
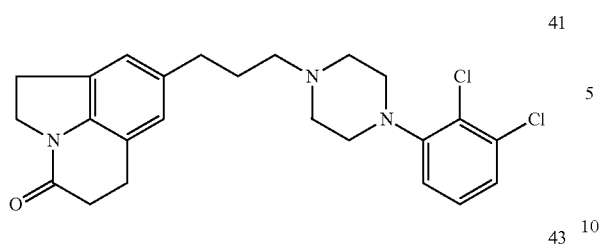
43
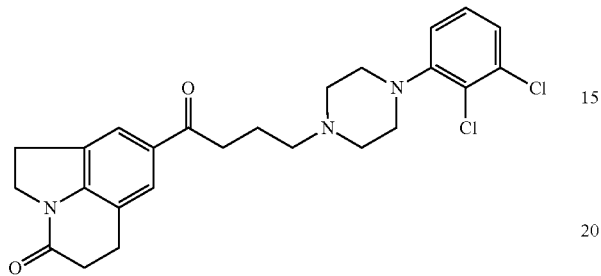
44
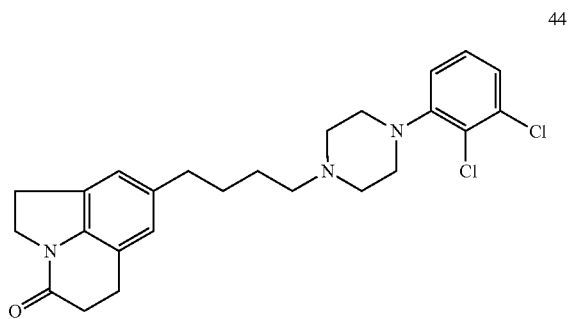
47
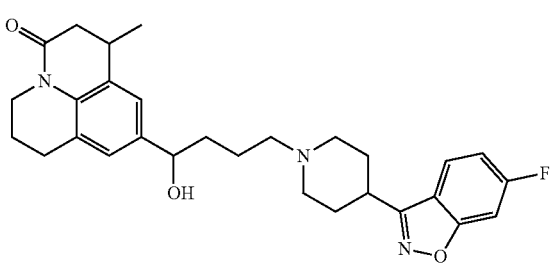
48
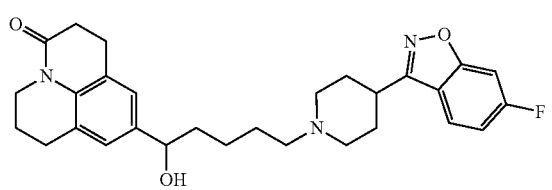
49
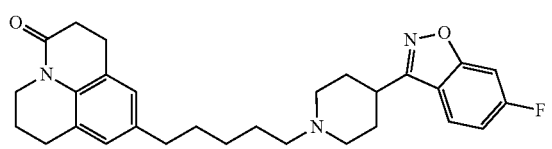
50
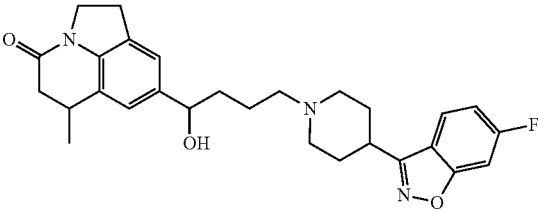
52
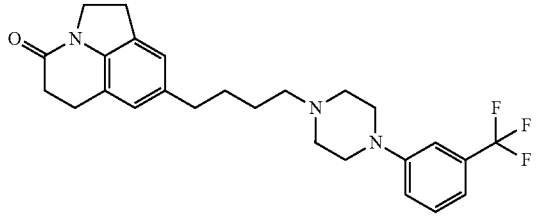
53
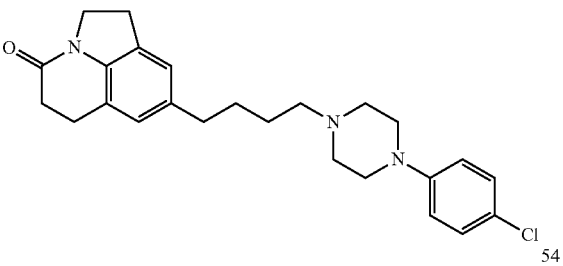
54
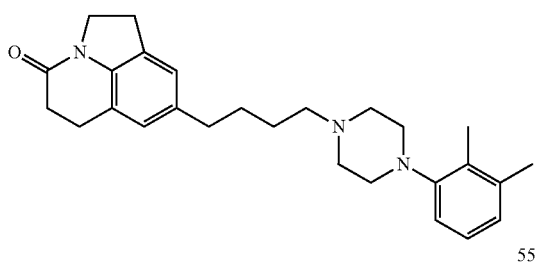
55
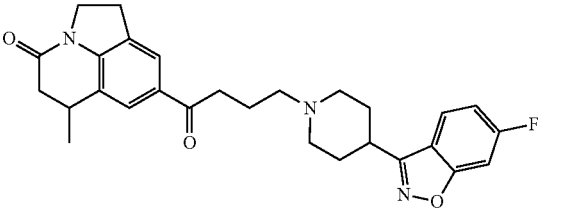
56
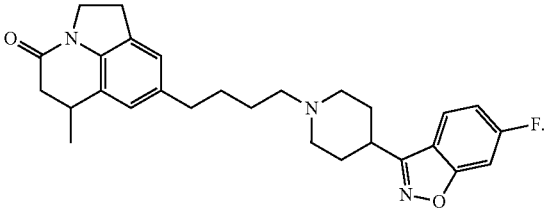
8. A pharmaceutical composition comprising the compound according to claim 1 or the pharmaceutically acceptable salt or thereof, and further comprising pharmaceutically acceptable excipient, carrier, adjuvant, solvent or the combination thereof.

9. A method for the treatment of schizophrenia, comprising administering to a subject in need thereof a therapeutically effective amount of the compound of claim 1 or the pharmaceutically acceptable salt thereof.

10. A method for the treatment of schizophrenia, comprising administering to a subject in need thereof a therapeutically effective amount of the pharmaceutical composition of claim 8.

11. The compound according to claim 5 or the pharmaceutically acceptable salt or thereof, wherein, $R_1$, $R_2$, $R_3$ or $R_4$ is each independently hydrogen, fluorine, phenyl, methyl, ethyl, propyl, trifluoromethyl or hydroxymethyl.

* * * * *